US008772300B2

(12) United States Patent
Jaeschke et al.

(10) Patent No.: US 8,772,300 B2
(45) Date of Patent: Jul. 8, 2014

(54) PHENYL OR PYRIDINYL-ETHYNYL DERIVATIVES

(75) Inventors: Georg Jaeschke, Basel (CH); Synese Jolidon, Blauen (CH); Lothar Lindemann, Basel (CH); Antonio Ricci, Birsfelden (CH); Daniel Rueher, Raedersdorf (FR); Heinz Stadler, Basel (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/443,911

(22) Filed: Apr. 11, 2012

(65) Prior Publication Data

US 2012/0270852 A1  Oct. 25, 2012

(30) Foreign Application Priority Data

Apr. 19, 2011 (EP) .................. 11162945
Oct. 14, 2011 (EP) .................. 11185137

(51) Int. Cl.
*A01N 43/54* (2006.01)
*C07D 239/42* (2006.01)
*C07D 401/04* (2006.01)

(52) U.S. Cl.
USPC ........... 514/256; 514/335; 514/354; 544/335; 546/255; 546/323

(58) Field of Classification Search
USPC ........... 546/314, 323, 255; 544/335; 514/335, 514/354, 256
See application file for complete search history.

(56) References Cited

U.S. PATENT DOCUMENTS

2013/0123524 A1* 5/2013 Kellens et al. ............... 554/205

FOREIGN PATENT DOCUMENTS

WO  WO 9902497 A2 * 1/1999
WO  2008/151184    12/2008
WO  2011/015343     2/2011

OTHER PUBLICATIONS

A. Ritzen et al., 19 Bioorganic & Medicinal Chemistry Letters, 3275-3278 (2009).*
A.L. Rodriguez, et al., Molecular Pharmacology (2010), 78(6), 1105-1123.*
A.G. Sams et al, Bioorganic & Medicinal Chemistry Letters (2011), 21(11), 3407-3410.*
F. Gastambide et al., Neuropsychopharmacology (2012), 37(4), 1057-1066.*
M. Noetzel, et al., Molecular Pharmacology (2012), 81(2), 120-133.*
G. Gilmour et al., Neuropharmacology (2013), 64, 224-239.*
F. Gastambide et al., Neuropharmacology (2013), 64, 240-247.*
T. Kiritoshi, et al., Neuropharmacology (2013), 66, 170-178.*
Cee, V. J. et al., Journal of Medicinal Chemistry (XP002675714), 50(4):627-640 (Jan. 25, 2007).
Patani G. A. et al., Chemical Reviews (XP000652176), 96(8):3147-3176 (Jan. 1, 1996).
Yasuyoshi, I. et al., Journal of Medicinal Chemistry (XP002568493), 49(3):1080-1100 (Jan. 1, 2006).
(International Search Report PCT/UP2012/056966 Apr. 17, 2012).

* cited by examiner

*Primary Examiner* — Deepak Rao
*Assistant Examiner* — Alexander R Pagano

(57) ABSTRACT

The present invention relates to ethynyl derivatives of formula I

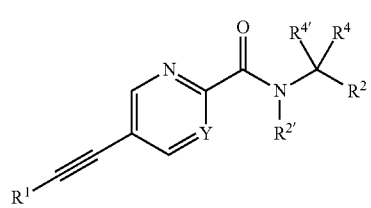

wherein
Y is N or C—$R^3$;
$R^3$ is hydrogen, methyl, halogen or nitrile;
$R^1$ is phenyl or pyridinyl, each of which is optionally substituted by halogen, lower alkyl or lower alkoxy;
$R^2/R^{2'}$ are each independently hydrogen, lower alkyl or lower alkyl substituted by halogen,
or $R^2$ and $R^{2'}$ together with the N-atom to which they are attached form a morpholine ring, a piperidine ring or an azetidine ring, each of which is unsubstituted or substituted one or more substituents selected from lower alkoxy, halogen, hydroxy and methyl;
$R^4/R^{4'}$ are each independently hydrogen or lower alkyl,
or $R^4$ and $R^{4'}$ together form a $C_{3-5}$ cycloalkyl-, tetrahydrofuran- or an oxetane-ring;
or to a pharmaceutically acceptable acid addition salt, to a racemic mixture, or to its corresponding enantiomer and/or optical isomer and/or stereoisomer thereof. Compounds of formula I are positive allosteric modulators (PAM) of the metabotropic glutamate receptor subtype 5 (mGluR5).

14 Claims, No Drawings

PHENYL OR PYRIDINYL-ETHYNYL DERIVATIVES

PRIORITY TO RELATED APPLICATION(S)

This application claims the benefit of European Patent Application No. 11162945.7, filed Apr. 19, 2011 and European Patent Application No. 11185137.4, filed Oct. 14, 2011, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

A new avenue for developing selective modulators is to identify compounds which act through allosteric mechanism, modulating the receptor by binding to site different from the highly conserved orthosteric binding site. Positive allosteric modulators of mGluR5 have emerged recently as novel pharmaceutical entities offering this attractive alternative. Positive allosteric modulators have been described, for example in WO2008/151184, WO2006/048771, WO2006/129199 and WO2005/044797 and in *Molecular Pharmacology*, 40, 333-336, 1991; *The Journal of Pharmacology and Experimental Therapeutics*, Vol 313, No. 1, 199-206, 2005;

Positive allosteric modulators are compounds that do not directly activate receptors by themselves, but markedly potentiate agonist-stimulated responses, increase potency and maximum of efficacy. The binding of these compounds increase the affinity of a glutamate-site agonist at its extracellular N-terminal binding site. Positive allosteric modulation is thus an attractive mechanism for enhancing appropriate physiological receptor activation. There is a scarcity of selective positive allosteric modulators for the mGluR5 receptor. Conventional mGluR5 receptor modulators typically lack satisfactory aqueous solubility and exhibit poor oral bioavailability. Therefore, there remains a need for compounds that overcome these deficiencies and that effectively provide selective positive allosteric modulators for the mGluR5 receptor.

SUMMARY OF THE INVENTION

The present invention provides ethynyl derivatives of formula I

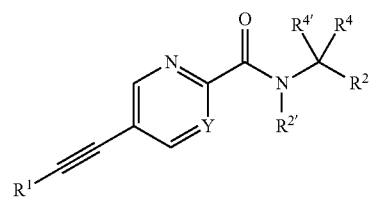

wherein
Y is N or C—$R^3$;
$R^3$ is hydrogen, methyl, halogen or nitrile;
$R^1$ is phenyl or pyridinyl, each of which is optionally substituted by halogen, lower alkyl or lower alkoxy;
$R^2/R^{2'}$ are each independently hydrogen, lower alkyl or lower alkyl substituted by halogen,
or $R^2$ and $R^{2'}$ together with the N-atom to which they are attached form a morpholine ring, a piperidine ring or an azetidine ring, each of which is unsubstituted or substituted one or more substituents selected from lower alkoxy, halogen, hydroxy and methyl;
$R^4/R^{4'}$ are each independently hydrogen or lower alkyl,
or $R^4$ and $R^{4'}$ together form a $C_{3-5}$ cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

Compounds of formula I are positive allosteric modulators (PAM) of the metabotropic glutamate receptor subtype 5 (mGluR5).

Compounds of formula I are distinguished by having valuable therapeutic properties. They can be used in the treatment or prevention of disorders, relating to positive allosteric modulators for the mGluR5 receptor.

The most preferred indications for compounds which are positive allosteric modulators are schizophrenia and cognition.

The present invention provides compounds of formula I and their pharmaceutically acceptable salts, pharmaceutical compositions containing these compounds, processes for their production, and their use in the treatment or prevention of disorders relating to positive allosteric modulators for the mGluR5 receptor, such as schizophrenia, tuberous sclerosis, and cognition.

DETAILED DESCRIPTION OF THE INVENTION

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "lower alkyl substituted by halogen" denotes an alkyl group as defined above, wherein at least one hydrogen atom is replaced by halogen. Preferred is the group $CF_3$.

The term "alkoxy" denotes a group —O—R' wherein R' is lower alkyl as defined above.

The term "halogen" denotes fluoro, chloro, bromo or iodo.

The term "$C_{3-5}$cycloalkyl" denotes a monovalent saturated monocyclic or bicyclic hydrocarbon group of 3 to 5 ring carbon atoms. Examples are cyclopropyl, cyclobutanyl, and cyclopentyl.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

One embodiment of the invention provides compounds of formula,

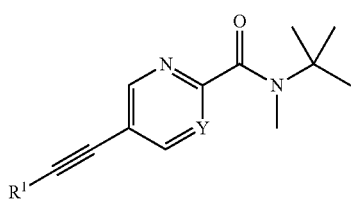

IA wherein
Y is N or C—$R^3$;
and $R^3$ is hydrogen, methyl, halogen or nitrile;
$R^1$ is phenyl or pyridinyl, each of which is optionally substituted by halogen, lower alkyl or lower alkoxy;
or a pharmaceutically acceptable acid addition salt, a racemic mixture, or its corresponding enantiomer and/or optical isomer and/or stereoisomer thereof.

The following compounds of formula IA have been prepared:

5-phenylethynyl-pyridine-2-carboxylic acid tert-butyl-methyl-amide;
5-(3-fluoro-phenylethynyl)-pyridine-2-carboxylic acid tert-butyl-methyl-amide;
5-(4-fluoro-phenylethynyl)-pyridine-2-carboxylic acid tert-butyl-methyl-amide;
5-(2,5-difluoro-phenylethynyl)-pyridine-2-carboxylic acid tert-butyl-methyl-amide;
5-pyridin-3-ylethynyl-pyridine-2-carboxylic acid tert-butyl-methyl-amide;
5-(5-chloro-pyridin-3-ylethynyl)-pyridine-2-carboxylic acid tert-butyl-methyl-amide;
5-(5-fluoro-pyridin-3-ylethynyl)-pyridine-2-carboxylic acid tert-butyl-methyl-amide;
5-(4-fluoro-phenylethynyl)-pyrimidine-2-carboxylic acid tert-butyl-methyl-amide;
5-(3-fluoro-phenylethynyl)-pyrimidine-2-carboxylic acid tert-butyl-methyl-amide;
5-(2,5-difluoro-phenylethynyl)-pyrimidine-2-carboxylic acid tert-butyl-methyl-amide;
5-(5-chloro-pyridin-3-ylethynyl)-pyrimidine-2-carboxylic acid tert-butyl-methyl-amide;
5-(3-fluoro-phenylethynyl)-3-methyl-pyridine-2-carboxylic acid tert-butyl-methyl-amide;
5-(4-fluoro-phenylethynyl)-3-methyl-pyridine-2-carboxylic acid tert-butyl-methyl-amide;
5-(2,5-difluoro-phenylethynyl)-3-methyl-pyridine-2-carboxylic acid tert-butyl-methyl-amide;
5-(5-chloro-pyridin-3-ylethynyl)-3-methyl-pyridine-2-carboxylic acid tert-butyl-methyl-amide;
3-fluoro-5-(3-fluoro-phenylethynyl)-pyridine-2-carboxylic acid tert-butyl-methyl-amide;
3-fluoro-5-(4-fluoro-phenylethynyl)-pyridine-2-carboxylic acid tert-butyl-methyl-amide;
5-(2,5-difluoro-phenylethynyl)-3-fluoro-pyridine-2-carboxylic acid tert-butyl-methyl-amide;
5-(5-chloro-pyridin-3-ylethynyl)-3-fluoro-pyridine-2-carboxylic acid tert-butyl-methyl-amide;
3-chloro-5-phenylethynyl-pyridine-2-carboxylic acid tert-butyl-methyl-amide; and
3-cyano-5-phenylethynyl-pyridine-2-carboxylic acid tert-butyl-methyl-amide.

A further embodiment of the invention provides compounds of formula I, wherein $R^1$ is phenyl, optionally substituted by halogen, for example the following compounds
5-phenylethynyl-pyridine-2-carboxylic acid tert-butylamide;
5-phenylethynyl-pyridine-2-carboxylic acid tert-butyl-methyl-amide;
5-(3-fluoro-phenylethynyl)-pyridine-2-carboxylic acid tert-butyl-methyl-amide;
5-(4-fluoro-phenylethynyl)-pyridine-2-carboxylic acid tert-butyl-methyl-amide;
5-(2,5-difluoro-phenylethynyl)-pyridine-2-carboxylic acid tert-butyl-methyl-amide;
5-(4-fluoro-phenylethynyl)-pyrimidine-2-carboxylic acid tert-butylamide;
5-(3-fluoro-phenylethynyl)-pyrimidine-2-carboxylic acid tert-butylamide;
5-(4-fluoro-phenylethynyl)-pyrimidine-2-carboxylic acid tert-butyl-methyl-amide;
5-(3-fluoro-phenylethynyl)-pyrimidine-2-carboxylic acid tert-butyl-methyl-amide;
5-m-tolylethynyl-pyrimidine-2-carboxylic acid tert-butylamide;
5-(3-chloro-phenylethynyl)-pyrimidine-2-carboxylic acid tert-butylamide;

5-(2,5-difluoro-phenylethynyl)-pyrimidine-2-carboxylic acid tert-butyl-methyl-amide;
5-(3-fluoro-phenylethynyl)-3-methyl-pyridine-2-carboxylic acid tert-butyl-methyl-amide;
5-(4-fluoro-phenylethynyl)-3-methyl-pyridine-2-carboxylic acid tert-butyl-methyl-amide;
5-(2,5-difluoro-phenylethynyl)-3-methyl-pyridine-2-carboxylic acid tert-butyl-methyl-amide;
3-fluoro-5-(3-fluoro-phenylethynyl)-pyridine-2-carboxylic acid tert-butyl-methyl-amide;
3-fluoro-5-(4-fluoro-phenylethynyl)-pyridine-2-carboxylic acid tert-butyl-methyl-amide;
5-(2,5-difluoro-phenylethynyl)-3-fluoro-pyridine-2-carboxylic acid tert-butyl-methyl-amide;
5-(3-fluoro-phenylethynyl)-pyridine-2-carboxylic acid cyclobutyl-methyl-amide;
5-(3-fluoro-phenylethynyl)-pyridine-2-carboxylic acid oxetan-3-ylamide;
5-(3-fluoro-phenylethynyl)-pyridine-2-carboxylic acid methyl-(3-methyl-oxetan-3-yl)-amide;
5-(4-fluoro-phenylethynyl)-pyridine-2-carboxylic acid methyl-(3-methyl-oxetan-3-yl)-amide;
5-(2,5-difluoro-phenylethynyl)-pyridine-2-carboxylic acid methyl-(3-methyl-oxetan-3-yl)-amide;
5-(3,4-difluoro-phenylethynyl)-pyridine-2-carboxylic acid methyl-(3-methyl-oxetan-3-yl)-amide;
5-(3-fluoro-phenylethynyl)-pyridine-2-carboxylic acid methyl-(1-methyl-cyclopropyl)-amide;
5-(4-fluoro-phenylethynyl)-pyridine-2-carboxylic acid methyl-(1-methyl-cyclopropyl)-amide;
5-(3-chloro-phenylethynyl)-pyridine-2-carboxylic acid methyl-(1-trifluoromethyl-cyclopropyl)-amide;
5-m-tolylethynyl-pyridine-2-carboxylic acid methyl-(1-trifluoromethyl-cyclopropyl)-amide;
(2,2-dimethyl-morpholin-4-yl)-[5-(3-fluoro-phenylethynyl)-pyridin-2-yl]-methanone;
[5-(2,5-difluoro-phenylethynyl)-pyridin-2-yl]-(2,2-dimethyl-morpholin-4-yl)-methanone;
[5-(3-fluoro-phenylethynyl)-pyridin-2-yl]-(4-hydroxy-4-methyl-piperidin-1-yl)-methanone;
(RS)-(4-hydroxy-2,2-dimethyl-piperidin-1-yl)-(5-phenylethynyl-pyridin-2-yl)-methanone;
(RS)-(4-hydroxy-3,3-dimethyl-piperidin-1-yl)-(5-phenylethynyl-pyridin-2-yl)-methanone;
(RS)-[5-(4-fluoro-phenylethynyl)-pyridin-2-yl]-(4-hydroxy-3,3-dimethyl-piperidin-1-yl)-methanone;
(RS)-[5-(3-fluoro-phenylethynyl)-pyridin-2-yl]-(4-hydroxy-3,3-dimethyl-piperidin-1-yl)-methanone;
3-fluoro-5-(3-fluoro-phenylethynyl)-pyridine-2-carboxylic acid methyl-(1-methyl-cyclopropyl)-amide;
3-chloro-5-phenylethynyl-pyridine-2-carboxylic acid tert-butyl-methyl-amide;
5-(3-fluoro-phenylethynyl)-pyrimidine-2-carboxylic acid methyl-(1-trifluoromethyl-cyclopropyl)-amide;
(3,3-difluoro-azetidin-1-yl)-(5-phenylethynyl-pyrimidin-2-yl)-methanone;
(3,3-dimethyl-piperidin-1-yl)-(5-phenylethynyl-pyrimidin-2-yl)-methanone;
(RS)-(4-hydroxy-2,2-dimethyl-piperidin-1-yl)-(5-phenylethynyl-pyrimidin-2-yl)-methanone;
(RS)-(4-hydroxy-3,3-dimethyl-piperidin-1-yl)-(5-phenylethynyl-pyrimidin-2-yl)-methanone;
(RS)-[5-(3-fluoro-phenylethynyl)-pyrimidin-2-yl]-(4-hydroxy-3,3-dimethyl-piperidin-1-yl)-methanone;
3-fluoro-5-phenylethynyl-pyridine-2-carboxylic acid methyl-(3-methyl-oxetan-3-yl)-amide;
(RS)-3-fluoro-5-phenylethynyl-pyridine-2-carboxylic acid methyl-(2,2,2-trifluoro-1-methyl-ethyl)-amide;
3-cyano-5-phenylethynyl-pyridine-2-carboxylic acid tert-butyl-methyl-amide;
5-(3-chloro-phenylethynyl)-pyridine-2-carboxylic acid methyl-(2,2,2-trifluoro-1,1-dimethyl-ethyl)-amide;
(RS)-5-(3-chloro-phenylethynyl)-pyridine-2-carboxylic acid (2,2,2-trifluoro-1-methyl-ethyl)-amide;
(RS)-5-(3-chloro-phenylethynyl)-pyridine-2-carboxylic acid methyl-(2,2,2-trifluoro-1-methyl-ethyl)-amide;
(RS)-[5-(3-fluoro-phenylethynyl)-pyridin-2-yl]-(4-hydroxy-2,2-dimethyl-piperidin-1-yl)-methanone;
(RS)-[5-(2,5-difluoro-phenylethynyl)-pyridin-2-yl]-(4-hydroxy-2,2-dimethyl-piperidin-1-yl)-methanone;
(RS)-[5-(3-fluoro-phenylethynyl)-pyrimidin-2-yl]-(4-hydroxy-2,2-dimethyl-piperidin-1-yl)-methanone;
(RS)-[5-(2,5-difluoro-phenylethynyl)-pyrimidin-2-yl]-(4-hydroxy-2,2-dimethyl-piperidin-1-yl)-methanone;
(RS)-[3-fluoro-5-(3-fluoro-phenylethynyl)-pyridin-2-yl]-(4-hydroxy-2,2-dimethyl-piperidin-1-yl)-methanone; and
(RS)-[5-(2,5-difluoro-phenylethynyl)-3-fluoro-pyridin-2-yl]-(4-hydroxy-2,2-dimethyl-piperidin-1-yl)-methanone.

A further embodiment of the invention provides compounds of formula I, wherein $R^1$ is pyridinyl, optionally substituted by halogen, for example the following compounds
5-pyridin-3-ylethynyl-pyridine-2-carboxylic acid tert-butyl-methyl-amide;
5-(5-chloro-pyridin-3-ylethynyl)-pyridine-2-carboxylic acid tert-butyl-methyl-amide;
5-(5-fluoro-pyridin-3-ylethynyl)-pyridine-2-carboxylic acid tert-butyl-methyl-amide;
5-(5-chloro-pyridin-3-ylethynyl)-pyrimidine-2-carboxylic acid tert-butyl-methyl-amide;
5-(5-chloro-pyridin-3-ylethynyl)-3-methyl-pyridine-2-carboxylic acid tert-butyl-methyl-amide;
5-(5-chloro-pyridin-3-ylethynyl)-3-fluoro-pyridine-2-carboxylic acid tert-butyl-methyl-amide;
5-(5-Chloro-pyridin-3-ylethynyl)-pyridine-2-carboxylic acid methyl-(1-trifluoromethyl-cyclopropyl)-amide;
5-(2-chloro-pyridin-4-ylethynyl)-pyridine-2-carboxylic acid (2,2,2-trifluoro-1,1-dimethyl-ethyl)-amide;
5-(5-chloro-pyridin-3-ylethynyl)-pyridine-2-carboxylic acid methyl-(2,2,2-trifluoro-1,1-dimethyl-ethyl)-amide;
(RS)-5-(2-chloro-pyridin-4-ylethynyl)-pyridine-2-carboxylic acid (2,2,2-trifluoro-1-methyl-ethyl)-amide;
5-(2-chloro-pyridin-4-ylethynyl)-pyrimidine-2-carboxylic acid (2,2,2-trifluoro-1,1-dimethyl-ethyl)-amide;
(R) or (S)-5-(2-chloro-pyridin-4-ylethynyl)-pyridine-2-carboxylic acid (2,2,2-trifluoro-1-methyl-ethyl)-amide; and
(S) or (R)-5-(2-chloro-pyridin-4-ylethynyl)-pyridine-2-carboxylic acid (2,2,2-trifluoro-1-methyl-ethyl)-amide.

One further embodiment of the invention provides compounds of formula I-1

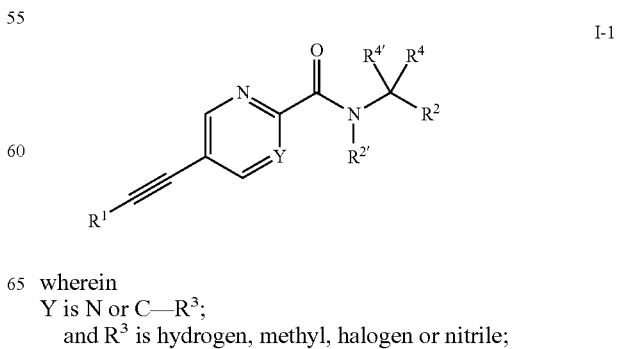

I-1 wherein
Y is N or C—$R^3$;
and $R^3$ is hydrogen, methyl, halogen or nitrile;

R¹ is phenyl or heteroaryl, which are optionally substituted by halogen, lower alkyl or lower alkoxy;

R²/R²' are each independently hydrogen, lower alkyl, lower alkyl substituted by halogen or CH₂-lower alkoxy,
or R² and R²' together with the N-atom to which they are attached form a morpholine ring, a piperidine ring or an azetidine ring, each of which is unsubstituted or substituted by lower alkoxy, halogen, hydroxy or methyl;

R⁴/R⁴' are each independently hydrogen, lower alkyl or CH₂-lower alkoxy,
or R⁴ and R⁴' together form a $C_{3-5}$ cycloalkyl-, tetrahydrofuran- or an oxetane-ring;

or a pharmaceutically acceptable acid addition salt, a racemic mixture, or its corresponding enantiomer and/or optical isomer and/or stereoisomer thereof.

Another embodiment of the invention provides compounds of formula I-2

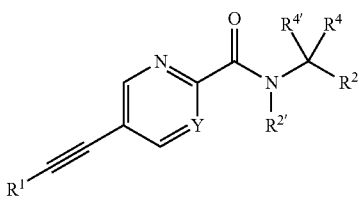

I-2 wherein
Y is N or C—R³;
and R³ is hydrogen, methyl, halogen or nitrile;
R¹ is phenyl or heteroaryl, which are optionally substituted by halogen, lower alkyl or lower alkoxy;
R²/R²' are each independently hydrogen, lower alkyl or CH₂-lower alkoxy,
or R² and R²' together with the N-atom to which they are attached form a ring with —(CH₂)₂,₃,₄—, —(CH₂)₂—NR⁵—CH₂— or —(CH₂)₂—O—CH₂—, which is unsubstituted or substituted by lower alkoxy, hydroxy or methyl;
wherein R⁵ is hydrogen or lower alkyl;
R⁴/R⁴' are each independently hydrogen, lower alkyl or CH₂-lower alkoxy,
or R⁴ and R⁴' together form a $C_{3-5}$ cycloalkyl-, tetrahydrofuran-, or an oxetane-ring;

or a pharmaceutically acceptable acid addition salt, a racemic mixture, or its corresponding enantiomer and/or optical isomer and/or stereoisomer thereof.

The preparation of compounds of formula I of the present invention can be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process variants described below, which process comprises a) reacting a compound of formula

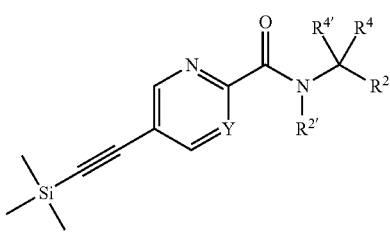

6 with a suitable compound of formula

R¹-hal 7 to form a compound of formula

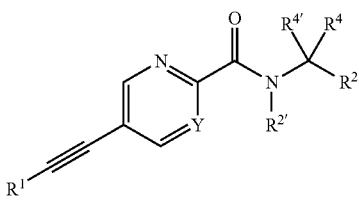

I wherein the substituents are described above or b) reacting a compound of formula

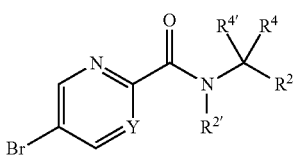

3 with a suitable compound of formula

4 to form a compound of formula

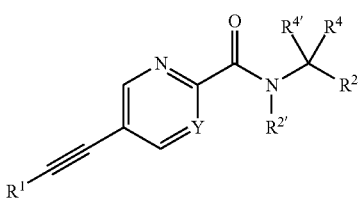

I c) reacting a compound of formula

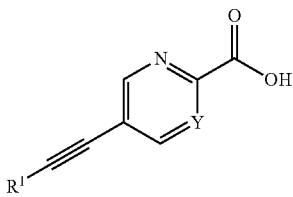

with a suitable compound of formula

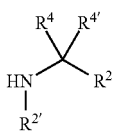

to form a compound of formula

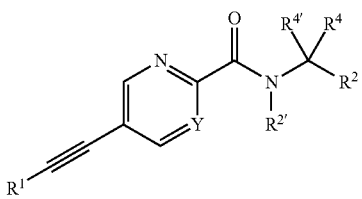

I wherein the substituents are described above or if desired, converting the compounds obtained into pharmaceutically acceptable acid addition salts.

The preparation of compounds of formula I is further described in more detail in schemes 1, 2 and 3 and in examples 1-68.

Scheme 1

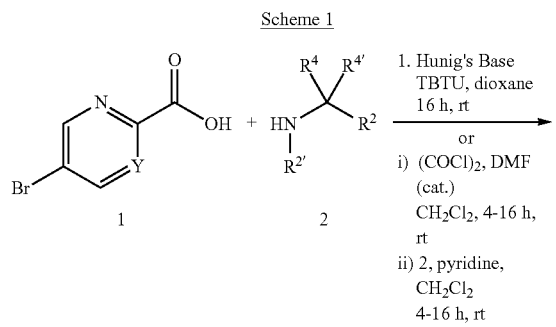

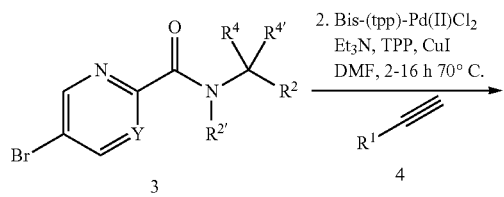

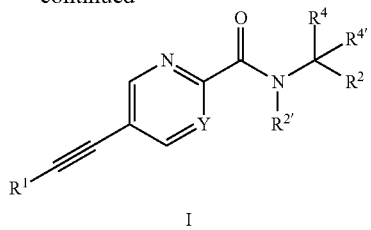

I

An ethynyl-pyridine or ethynyl-pyrimidine compound of formula I can be obtained for example by reacting a 5-bromo-pyridine-2-carboxylic acid or 5-bromo-pyrimidine-2-carboxylic acid 1 with an appropriate amine 2 in presence of a base such as Hunig's Base and a peptide coupling reagent such as TBTU in a solvent such as dioxane or by preparing in-situ the corresponding acid chloride with oxalyl chloride and DMF (cat.) in a solvent such as dichloromethane followed by reaction with the amine 2 in the presence of a base such as pyridine. Sonogashira coupling of the 5-bromo-pyridine-2-carboxylic acid amide or 5-bromo-pyrimidine-2-carboxylic acid amide 3 with an appropriately substituted arylacetylene 4 yield the desired ethynyl compounds of general formula I (scheme 1). Introduction of the $R^{2'}$ substituent can also be realized at various points in the synthetic sequence via alkylation of the corresponding intermediate where $R^{2'}$=H.

Scheme 2

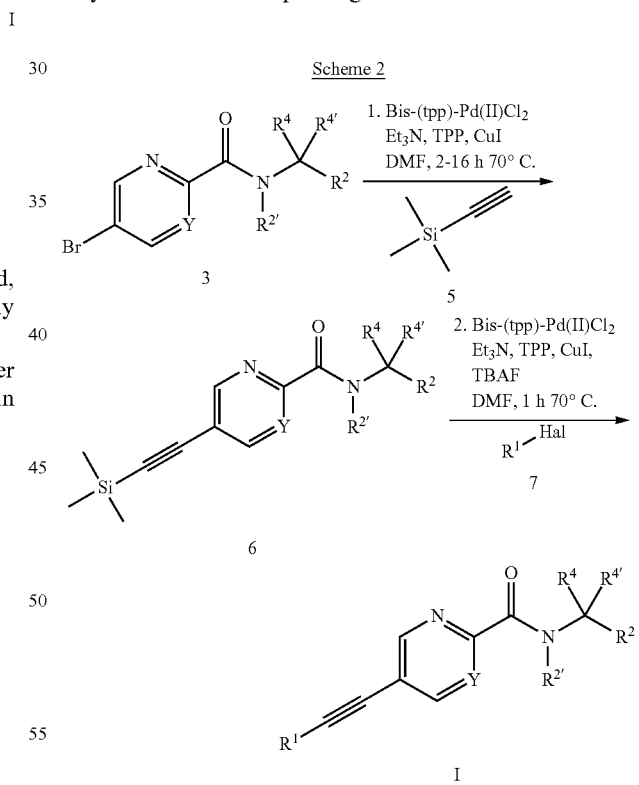

An ethynyl-pyridine or ethynyl-pyrimidine compound of formula I can be obtained by Sonogashira coupling of a 5-bromo-pyridine-2-carboxylic acid amide or 5-bromo-pyrimidine-2-carboxylic acid amide 3 with ethynyltrimethylsilane 5 to yield the corresponding 5-trimethylsilanylethynyl-derivatives 6. Sonogashira coupling with in-situ desilylation of 6 and an appropriately substituted aryl-halogenide 7 yields the desired ethynyl-pyridine or ethynyl-pyrimidine compounds of formula I (scheme 2). Introduction of the $R^{2'}$ substituent can also be realized at various points in the synthetic sequence via alkylation of the corresponding intermediate where $R^{2'}=H$.

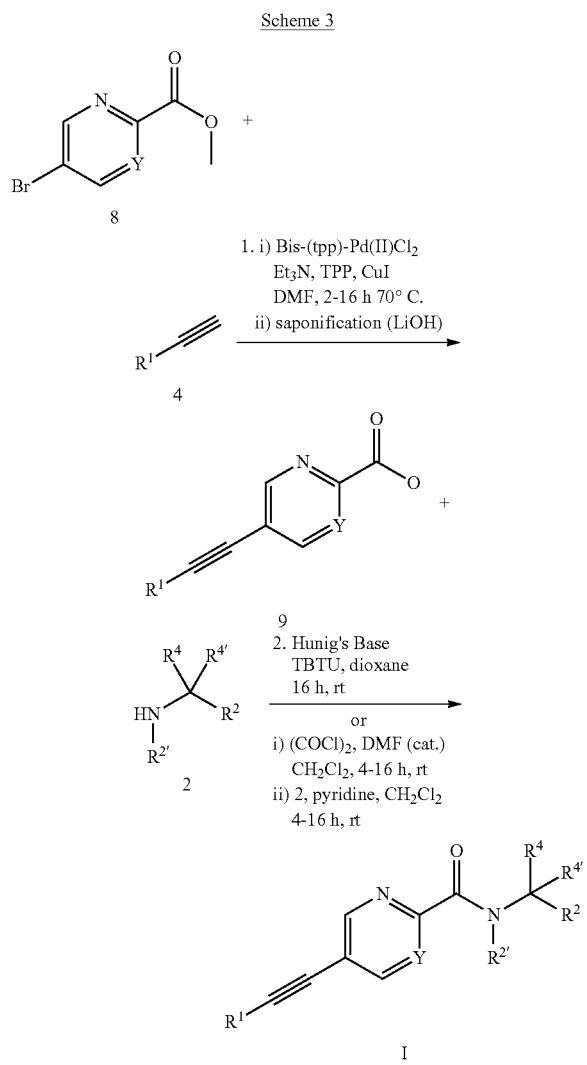

Generally speaking, the sequence of steps used to synthesize the compounds of formula I can also be modified in certain cases, for example by first running the Sonogashira coupling with 5-bromo-pyridine-2-carboxylic acid methyl ester or 5-bromo-pyrimidine-2-carboxylic acid methyl ester 8 and an appropriately substituted arylacetylene 4 followed by saponification with a base such as LiOH to yield the corresponding acid 9. Reacting the corresponding acid 9 with an appropriate amine 2 in presence of a base such as Hunig's Base and a peptide coupling reagent such as TBTU in a solvent such as dioxane or by preparing in-situ the corresponding acid chloride with oxalyl chloride and DMF (cat.) in a solvent such as dichloromethane followed by reaction with the amine 2 in the presence of a base such as pyridine yield the desired ethynyl compounds of general formula I (scheme 3). Introduction of the $R^{2'}$ substituent can also be realized at various points in the synthetic sequence via alkylation of the corresponding intermediate where $R^{2'}=H$.

Preferably, the compound of formula I as described herein as well as its pharmaceutically acceptable salt is used in the treatment or prevention of psychosis, epilepsy, schizophrenia, Alzheimer's disease, cognitive disorders and memory deficits, chronic and acute pain, restricted brain function caused by bypass operations or transplants, poor blood supply to the brain, spinal cord injuries, head injuries, hypoxia caused by pregnancy, cardiac arrest and hypoglycaemia, ischemia, Huntington's chorea, amyotrophic lateral sclerosis (ALS), dementia caused by AIDS, eye injuries, retinopathy, idiopathic parkinsonism or parkinsonism caused by medicaments, muscle spasms, convulsions, migraine, urinary incontinence, gastrointestinal reflux disorder, liver damage or failure whether drug or disease induced, Fragile-X syndrome, Down syndrome, autism, nicotine addiction, opiate addiction, anxiety, vomiting, dyskinesia, eating disorders, in particular bulimia or anorexia nervosa, and depressions, particularly for the treatment and prevention of acute and/or chronic neurological disorders, anxiety, the treatment of chronic and acute pain, urinary incontinence and obesity.

The preferred indications are schizophrenia and cognitive disorders.

Present invention further relates to the use of a compound of formula I as described herein, as well as its pharmaceutically acceptable salt, for the manufacture of a medicament, preferably for the treatment and prevention of the above-mentioned disorders.

Biological Assay and Data

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min with on-line recording of fluorescence. Following this pre-incubation step, the agonist L-glutamate was added to the cells at a concentration corresponding to $EC_{20}$ (typically around 80 µM) with on-line recording of fluorescence; in order to account for day-to-day variations in the responsiveness of cells, the $EC_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was $y=A+((B-A)/(1+((x/C)^D)))$, where y is the % maximal stimulatory effect, A is the minimum y, B is the maximum y, C is the EC$_{50}$, x is the log 10 of the concentration of the competing compound and D is the slope of the curve (the Hill Coefficient). From these curves the EC$_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an EC$_{20}$ concentration of L-glutamate) were indicative of an agonistic activity, the absence of such signals were demonstrating the lack of agonistic activities. A depression of the signal observed after addition of the EC$_{20}$ concentration of L-glutamate was indicative of an inhibitory activity of the test compound.

In the table below are shown the prepared compounds 1-68 with corresponding results (EC$_{50}$ in nM).

LIST OF EXAMPLES

| Ex. | Structure | Name | EC$_{50}$ (nM) mGlu5PAM | Eff. (%) |
|---|---|---|---|---|
| 1 | 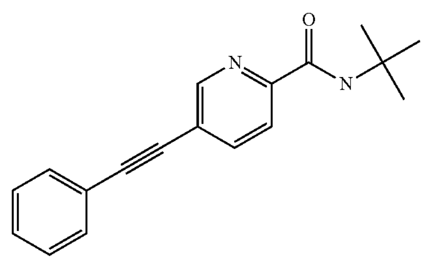 [SMILES: CC(C)(C)NC(=O)c1ccc(C#Cc2ccccc2)cn1] | 5-Phenylethynyl-pyridine-2-carboxylic acid tert-butylamide | 49 | 115 |
| 2 | 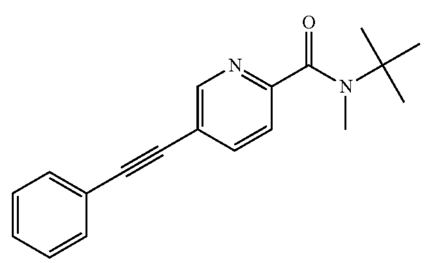 [SMILES: CN(C(=O)c1ccc(C#Cc2ccccc2)cn1)C(C)(C)C] | 5-Phenylethynyl-pyridine-2-carboxylic acid tert-butyl-methyl-amide | 19 | 87 |
| 3 | 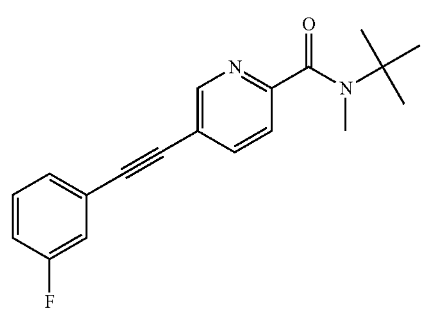 [SMILES: CN(C(=O)c1ccc(C#Cc2cccc(F)c2)cn1)C(C)(C)C] | 5-(3-Fluoro-phenylethynyl)-pyridine-2-carboxylic acid tert-butyl-methyl-amide | 16 | 64 |
| 4 | 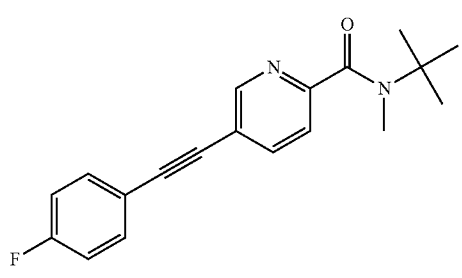 | 5-(4-Fluoro-phenylethynyl)-pyridine-2-carboxylic acid tert-butyl-methyl-amide | 18 | 83 |

-continued

| Ex. | Structure | Name | EC$_{50}$ (nM) mGlu5PAM | Eff. (%) |
|---|---|---|---|---|
| 5 | 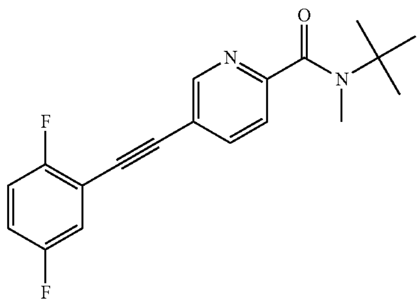 [SMILES: CN(C(=O)c1ccc(C#Cc2cc(F)ccc2F)cn1)C(C)(C)C] | 5-(2,5-Difluoro-phenylethynyl)-pyridine-2-carboxylic acid tert-butyl-methyl-amide | 12 | 42 |
| 6 | 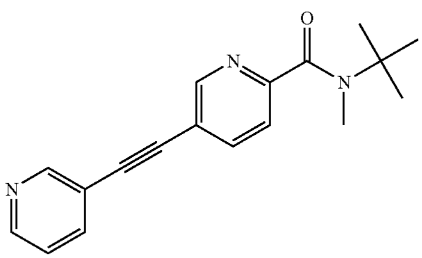 [SMILES: CN(C(=O)c1ccc(C#Cc2cccnc2)cn1)C(C)(C)C] | 5-Pyridin-3-ylethynyl-pyridine-2-carboxylic acid tert-butyl-methyl-amide | 72 | 70 |
| 7 | 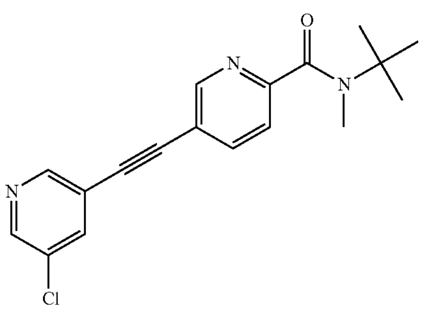 [SMILES: CN(C(=O)c1ccc(C#Cc2cncc(Cl)c2)cn1)C(C)(C)C] | 5-(5-Chloro-pyridin-3-ylethynyl)-pyridine-2-carboxylic acid tert-butyl-methyl-amide | 17 | 33 |
| 8 | 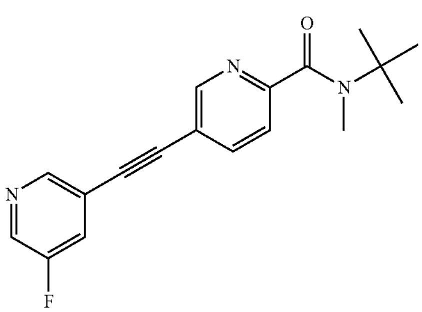 [SMILES: CN(C(=O)c1ccc(C#Cc2cncc(F)c2)cn1)C(C)(C)C] | 5-(5-Fluoro-pyridin-3-ylethynyl)-pyridine-2-carboxylic acid tert-butyl-methyl-amide | 62 | 79 |
| 9 | 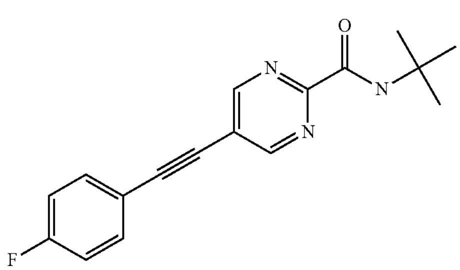 [SMILES: CC(C)(C)NC(=O)c1ncc(C#Cc2ccc(F)cc2)cn1] | 5-(4-Fluoro-phenylethynyl)-pyrimidine-2-carboxylic acid tert-butylamide | 127 | 90 |

| Ex. | Structure | Name | EC$_{50}$ (nM) mGlu5PAM | Eff. (%) |
|---|---|---|---|---|
| 10 | 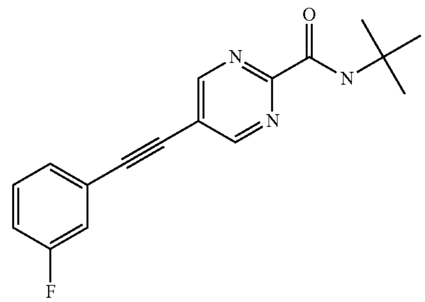 [SMILES: CC(C)(C)NC(=O)c1ncc(C#Cc2cccc(F)c2)cn1] | 5-(3-Fluoro-phenylethynyl)-pyrimidine-2-carboxylic acid tert-butylamide | 36 | 81 |
| 11 | 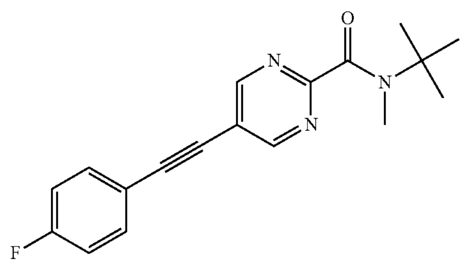 [SMILES: CN(C(=O)c1ncc(C#Cc2ccc(F)cc2)cn1)C(C)(C)C] | 5-(4-Fluoro-phenylethynyl)-pyrimidine-2-carboxylic acid tert-butyl-methyl-amide | 34 | 69 |
| 12 | 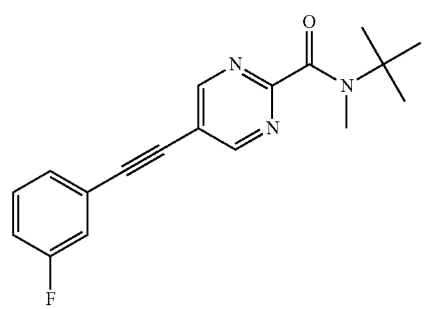 [SMILES: CN(C(=O)c1ncc(C#Cc2cccc(F)c2)cn1)C(C)(C)C] | 5-(3-Fluoro-phenylethynyl)-pyrimidine-2-carboxylic acid tert-butyl-methyl-amide | 23 | 55 |
| 13 | 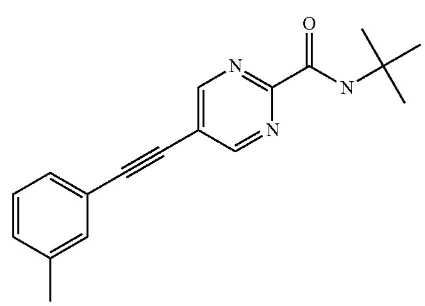 [SMILES: Cc1cccc(C#Cc2cnc(C(=O)NC(C)(C)C)nc2)c1] | 5-m-Tolylethynyl-pyrimidine-2-carboxylic acid tert-butylamide | 71 | 83 |
| 14 | 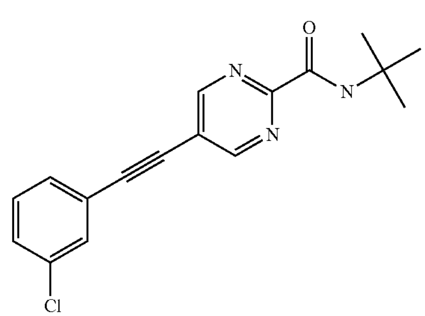 [SMILES: CC(C)(C)NC(=O)c1ncc(C#Cc2cccc(Cl)c2)cn1] | 5-(3-Chloro-phenylethynyl)-pyrimidine-2-carboxylic acid tert-butylamide | 111 | 95 |

| Ex. | Structure | Name | EC$_{50}$ (nM) mGlu5PAM | Eff. (%) |
|---|---|---|---|---|
| 15 | 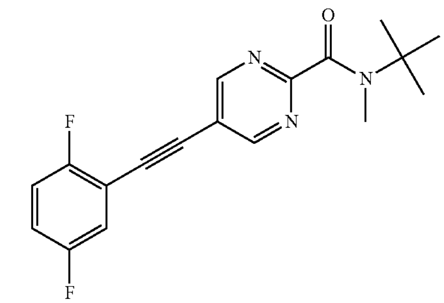 [SMILES: CN(C(=O)c1ncc(C#Cc2cc(F)ccc2F)cn1)C(C)(C)C] | 5-(2,5-Difluoro-phenylethynyl)-pyrimidine-2-carboxylic acid tert-butyl-methyl-amide | 35 | 32 |
| 16 | 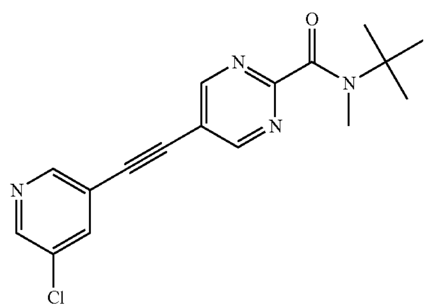 [SMILES: CN(C(=O)c1ncc(C#Cc2cncc(Cl)c2)cn1)C(C)(C)C] | 5-(5-Chloro-pyridin-3-ylethynyl)-pyrimidine-2-carboxylic acid tert-butyl-methyl-amide | 58 | 27 |
| 17 | 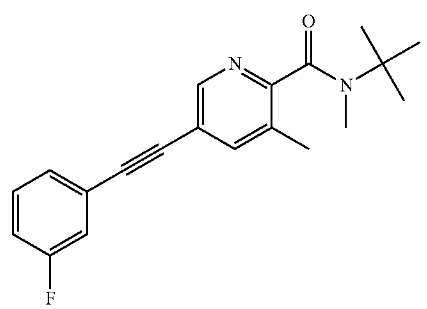 [SMILES: Cc1cc(C#Cc2cccc(F)c2)cnc1C(=O)N(C)C(C)(C)C] | 5-(3-Fluoro-phenylethynyl)-3-methyl-pyridine-2-carboxylic acid tert-butyl-methyl-amide | 37 | 49 |
| 18 | 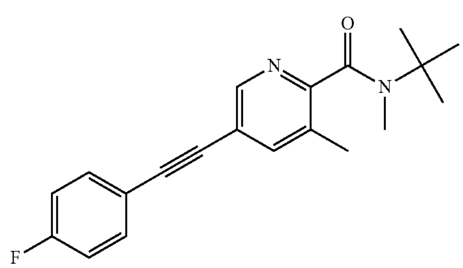 [SMILES: Cc1cc(C#Cc2ccc(F)cc2)cnc1C(=O)N(C)C(C)(C)C] | 5-(4-Fluoro-phenylethynyl)-3-methyl-pyridine-2-carboxylic acid tert-butyl-methyl-amide | 76 | 71 |
| 19 | 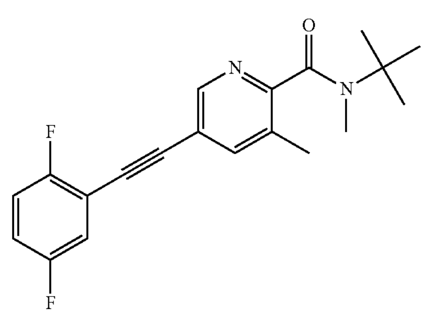 [SMILES: Cc1cc(C#Cc2cc(F)ccc2F)cnc1C(=O)N(C)C(C)(C)C] | 5-(2,5-Difluoro-phenylethynyl)-3-methyl-pyridine-2-carboxylic acid tert-butyl-methyl-amide | 33 | 29 |

-continued

| Ex. | Structure | Name | EC$_{50}$ (nM) mGlu5PAM | Eff. (%) |
|---|---|---|---|---|
| 20 | 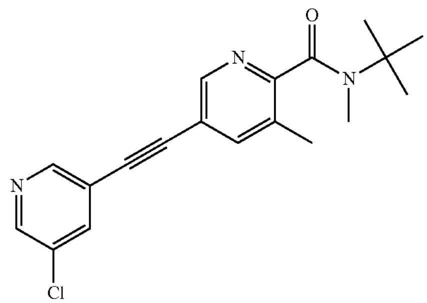 [SMILES: Cc1cc(C#Cc2cncc(Cl)c2)cnc1C(=O)N(C)C(C)(C)C] | 5-(5-Chloro-pyridin-3-ylethynyl)-3-methyl-pyridine-2-carboxylic tert-butyl-methyl-amide | 102 | 26 |
| 21 | 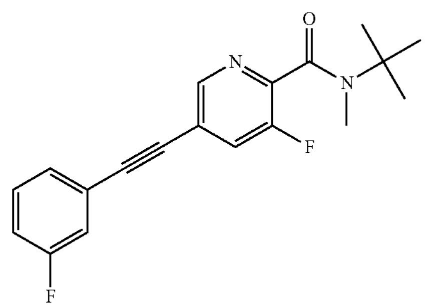 | 3-Fluoro-5-(3-fluoro-phenylethynyl)-pyridine-2-carboxylic acid tert-butyl-methyl-amide | 18 | 54 |
| 22 | 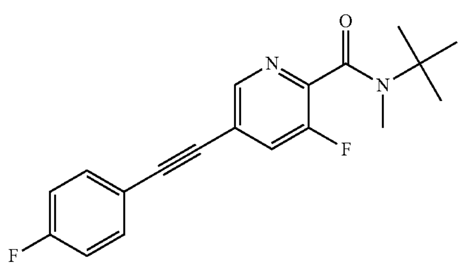 | 3-Fluoro-5-(4-fluoro-phenylethynyl)-pyridine-2-carboxylic acid tert-butyl-methyl-amide | 32 | 65 |
| 23 | 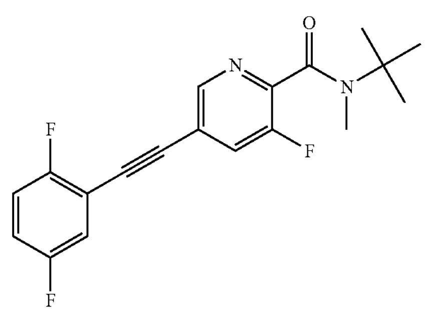 [SMILES: CN(C(=O)c1ncc(C#Cc2cc(F)ccc2F)cc1F)C(C)(C)C] | 5-(2,5-Difluoro-phenylethynyl)-3-fluoro-pyridine-2-carboxylic acid tert-butyl-methyl-amide | 10 | 38 |
| 24 | 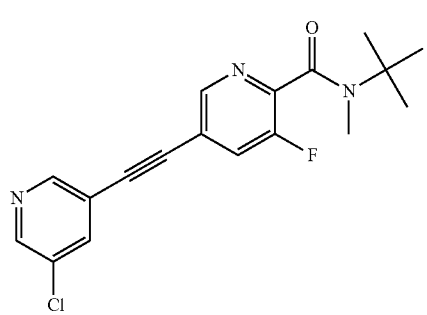 [SMILES: CN(C(=O)c1ncc(C#Cc2cncc(Cl)c2)cc1F)C(C)(C)C] | 5-(5-Chloro-pyridin-3-ylethynyl)-3-fluoro-pyridine-2-carboxylic acid tert-butyl-methyl-amide | 11 | 29 |

-continued

| Ex. | Structure | Name | EC$_{50}$ (nM) mGlu5PAM | Eff. (%) |
|---|---|---|---|---|
| 25 | 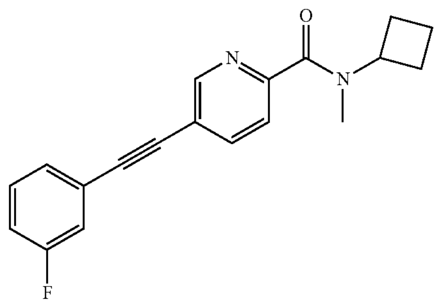 [SMILES: CN(C(=O)c1ccc(C#Cc2cccc(F)c2)cn1)C1CCC1] | 5-(3-Fluoro-phenylethynyl)-pyridine-2-carboxylic acid cyclobutyl-methyl-amide | 32 | 56 |
| 26 | 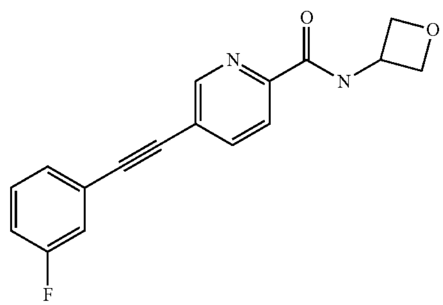 [SMILES: O=C(NC1COC1)c1ccc(C#Cc2cccc(F)c2)cn1] | 5-(3-Fluoro-phenylethynyl)-pyridine-2-carboxylic acid oxetan-3-ylamide | 43 | 80 |
| 27 | 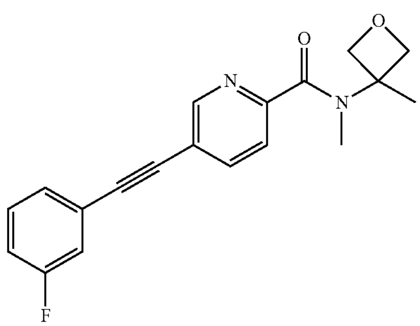 [SMILES: CN(C(=O)c1ccc(C#Cc2cccc(F)c2)cn1)C1(C)COC1] | 5-(3-Fluoro-phenylethynyl)-pyridine-2-carboxylic acid methyl-(3-methyl-oxetan-3-yl)-amide | 24 | 53 |
| 28 | 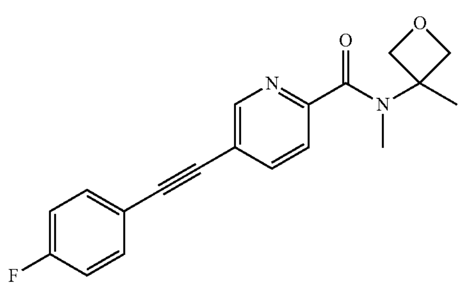 [SMILES: CN(C(=O)c1ccc(C#Cc2ccc(F)cc2)cn1)C1(C)COC1] | 5-(4-Fluoro-phenylethynyl)-pyridine-2-carboxylic acid methyl-(3-methyl-oxetan-3-yl)-amide | 37 | 68 |
| 29 | 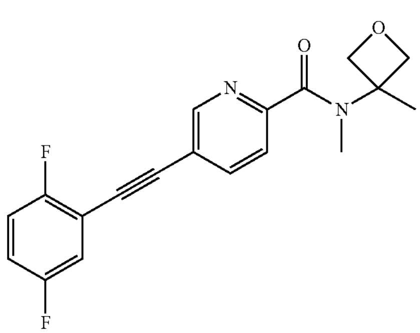 [SMILES: CN(C(=O)c1ccc(C#Cc2cc(F)ccc2F)cn1)C1(C)COC1] | 5-(2,5-Difluoro-phenylethynyl)-pyridine-2-carboxylic acid methyl-(3-methyl-oxetan-3-yl)-amide | 21 | 45 |

| Ex. | Structure | Name | EC$_{50}$ (nM) mGlu5PAM | Eff. (%) |
|---|---|---|---|---|
| 30 | 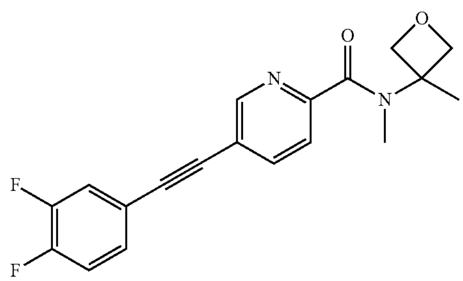 [SMILES: CN(C(=O)c1ccc(C#Cc2ccc(F)c(F)c2)cn1)C1(C)COC1] | 5-(3,4-Difluoro-phenylethynyl)-pyridine-2-carboxylic acid methyl-(3-methyl-oxetan-3-yl)-amide | 60 | 50 |
| 31 | 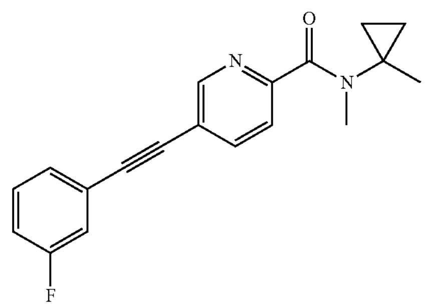 [SMILES: CN(C(=O)c1ccc(C#Cc2cccc(F)c2)cn1)C1(C)CC1] | 5-(3-Fluoro-phenylethynyl)-pyridine-2-carboxylic acid methyl-(1-methyl-cyclopropyl)-amide | 17 | 43 |
| 32 | 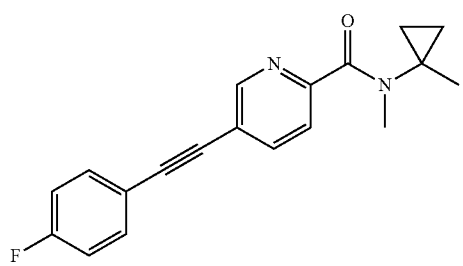 [SMILES: CN(C(=O)c1ccc(C#Cc2ccc(F)cc2)cn1)C1(C)CC1] | 5-(4-Fluoro-phenylethynyl)-pyridine-2-carboxylic acid methyl-(1-methyl-cyclopropyl)-amide | 24 | 59 |
| 33 | 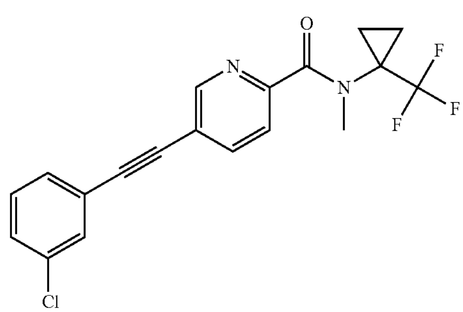 [SMILES: CN(C(=O)c1ccc(C#Cc2cccc(Cl)c2)cn1)C1(C(F)(F)F)CC1] | 5-(3-Chloro-phenylethynyl)-pyridine-2-carboxylic acid methyl-(1-trifluoromethyl-cyclopropyl)-amide | 33 | 37 |
| 34 | 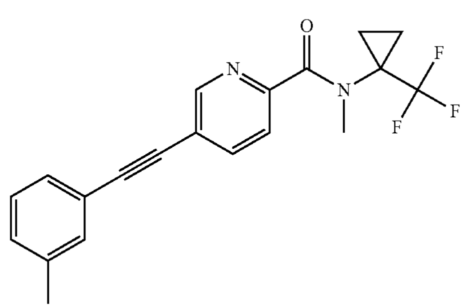 [SMILES: Cc1cccc(C#Cc2ccc(C(=O)N(C)C3(C(F)(F)F)CC3)nc2)c1] | 5-m-Tolylethynyl-pyridine-2-carboxylic acid methyl-(1-trifluoromethyl-cyclopropyl)-amide | 27 | 46 |

-continued

| Ex. | Structure | Name | EC$_{50}$ (nM) mGlu5PAM | Eff. (%) |
|---|---|---|---|---|
| 35 | 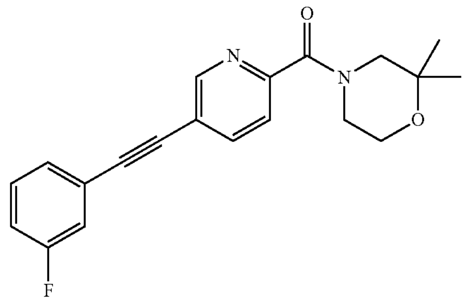 [SMILES: CC1(C)CN(C(=O)c2ccc(C#Cc3cccc(F)c3)cn2)CCO1] | (2,2-Dimethyl-morpholin-4-yl)-[5-(3-fluoro-phenylethynyl)-pyridin-2-yl]-methanone | 46 | 57 |
| 36 | 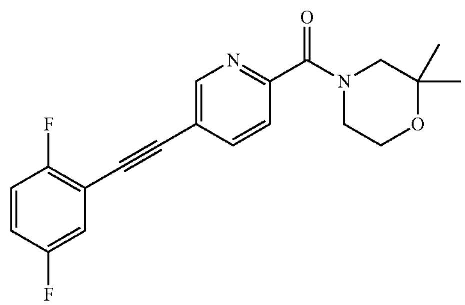 [SMILES: CC1(C)CN(C(=O)c2ccc(C#Cc3cc(F)ccc3F)cn2)CCO1] | [5-(2,5-Difluoro-phenylethynyl)-pyridin-2-yl]-(2,2-dimethyl-morpholin-4-yl)-methanone | 56 | 44 |
| 37 | 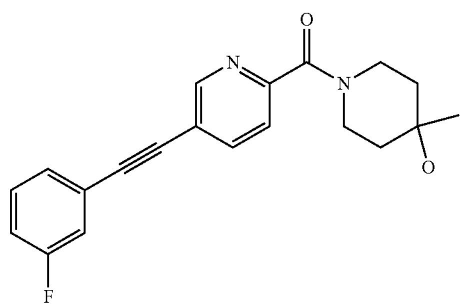 [SMILES: CC1(O)CCN(C(=O)c2ccc(C#Cc3cccc(F)c3)cn2)CC1] | [5-(3-Fluoro-phenylethynyl)-pyridin-2-yl]-(4-hydroxy-4-methyl-piperidin-1-yl)-methanone | 79 | 38 |
| 38 | 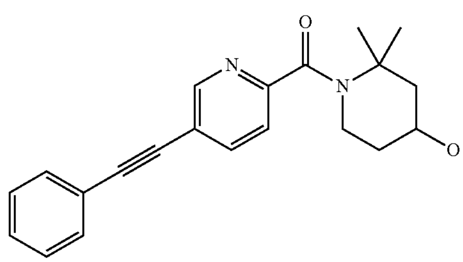 [SMILES: CC1(C)CC(O)CCN1C(=O)c1ccc(C#Cc2ccccc2)cn1] | (RS)-(4-Hydroxy-2,2-dimethyl-piperidin-1-yl)-(5-phenylethynyl-pyridin-2-yl)-methanone | 28 | 57 |
| 39 | 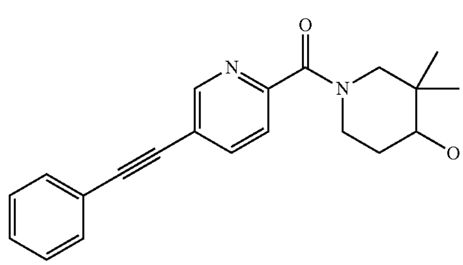 [SMILES: CC1(C)CN(C(=O)c2ccc(C#Cc3ccccc3)cn2)CCC1O] | (RS)-(4-Hydroxy-3,3-dimethyl-piperidin-1-yl)-(5-phenylethynyl-pyridin-2-yl)-methanone | 35 | 58 |

| Ex. | Structure | Name | EC$_{50}$ (nM) mGlu5PAM | Eff. (%) |
|---|---|---|---|---|
| 40 | 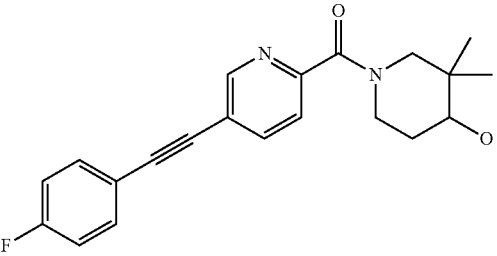 [SMILES: CC1(C)CN(C(=O)c2ccc(C#Cc3ccc(F)cc3)cn2)CCC1O] | (RS)-[5-(4-Fluoro-phenylethynyl)-pyridin-2-yl]-(4-hydroxy-3,3-dimethyl-piperidin-1-yl)-methanone | 93 | 37 |
| 41 | 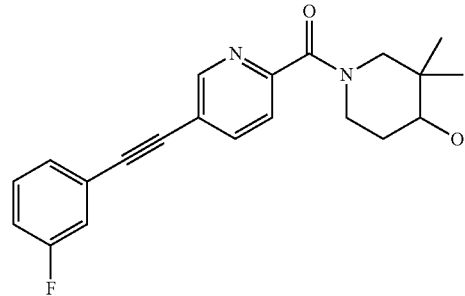 [SMILES: CC1(C)CN(C(=O)c2ccc(C#Cc3cccc(F)c3)cn2)CCC1O] | (RS)-[5-(3-Fluoro-phenylethynyl)-pyridin-2-yl]-(4-hydroxy-3,3-dimethyl-piperidin-1-yl)-methanone | 72 | 45 |
| 42 | 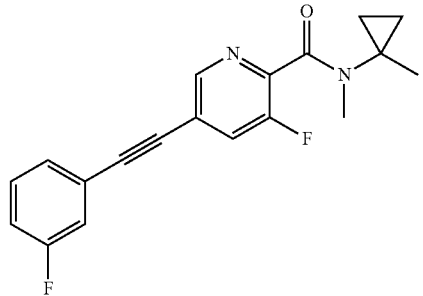 [SMILES: CN(C(=O)c1ncc(C#Cc2cccc(F)c2)cc1F)C1(C)CC1] | 3-Fluoro-5-(3-fluoro-phenylethynyl)-pyridine-2-carboxylic acid methyl-(1-methyl-cyclopropyl)-amide | 33 | 35 |
| 43 | 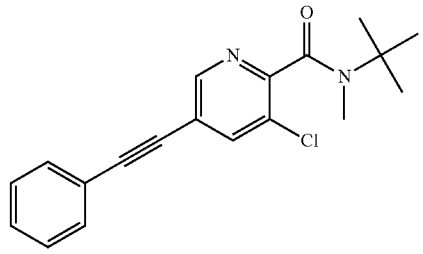 [SMILES: CN(C(=O)c1ncc(C#Cc2ccccc2)cc1Cl)C(C)(C)C] | 3-Chloro-5-phenylethynyl-pyridine-2-carboxylic acid tert-butyl-methyl-amide | 36 | 69 |
| 44 | 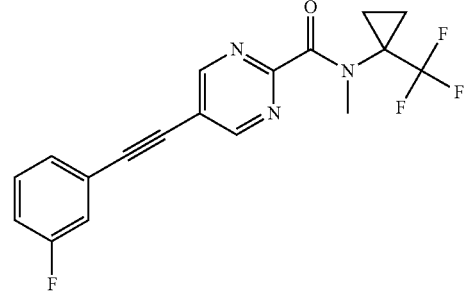 [SMILES: CN(C(=O)c1ncc(C#Cc2cccc(F)c2)cn1)C1(C(F)(F)F)CC1] | 5-(3-Fluoro-phenylethynyl)-pyrimidine-2-carboxylic acid methyl-(1-trifluoromethyl-cyclopropyl)-amide | 42 | 68 |

| Ex. | Structure | Name | EC₅₀ (nM) mGlu5PAM | Eff. (%) |
|---|---|---|---|---|
| 45 | 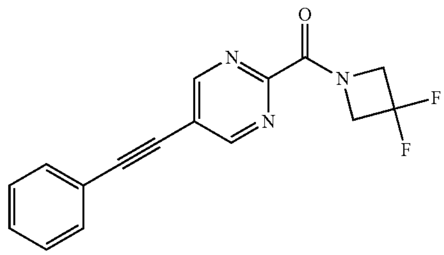 [SMILES: O=C(c1ncc(C#Cc2ccccc2)cn1)N1CC(F)(F)C1] | (3,3-Difluoro-azetidin-1-yl)-(5-phenylethynyl-pyrimidin-2-yl)-methanone | 62 | 51 |
| 46 | 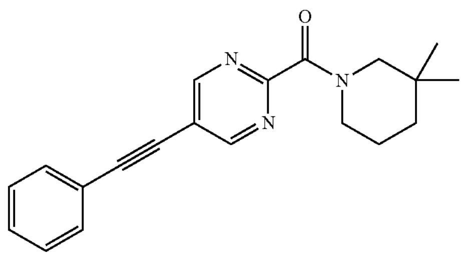 [SMILES: CC1(C)CCCN(C(=O)c2ncc(C#Cc3ccccc3)cn2)C1] | (3,3-Dimethyl-piperidin-1-yl)-(5-phenylethynyl-pyrimidin-2-yl)-methanone | 50 | 59 |
| 47 | 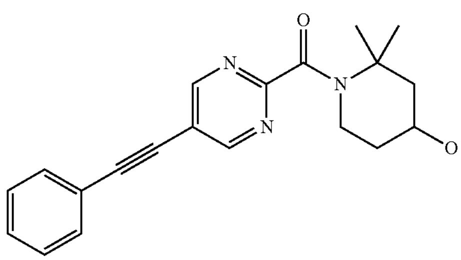 [SMILES: CC1(C)CC(O)CCN1C(=O)c1ncc(C#Cc2ccccc2)cn1] | (RS)-(4-Hydroxy-2,2-dimethyl-piperidin-1-yl)-(5-phenylethynyl-pyrimidin-2-yl)-methanone | 66 | 57 |
| 48 | 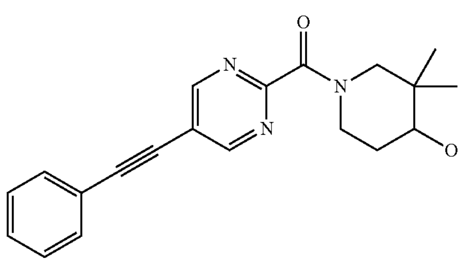 [SMILES: CC1(C)CN(C(=O)c2ncc(C#Cc3ccccc3)cn2)CCC1O] | (RS)-(4-Hydroxy-3,3-dimethyl-piperidin-1-yl)-(5-phenylethynyl-pyrimidin-2-yl)-methanone | 49 | 55 |
| 49 | 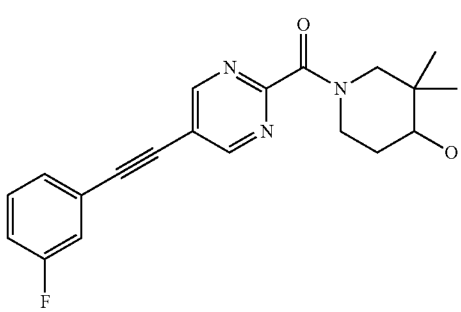 [SMILES: CC1(C)CN(C(=O)c2ncc(C#Cc3cccc(F)c3)cn2)CCC1O] | (RS)-[5-(3-Fluoro-phenylethynyl)-pyrimidin-2-yl]-(4-hydroxy-3,3-dimethyl-piperidin-1-yl)-methanone | 98 | 48 |

-continued

| Ex. | Structure | Name | EC$_{50}$ (nM) mGlu5PAM | Eff. (%) |
|---|---|---|---|---|
| 50 | 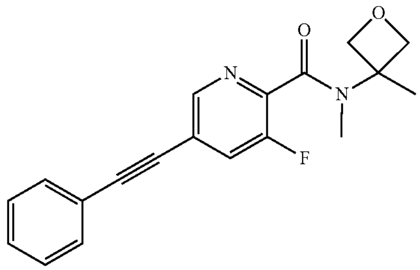 [SMILES: CN(C(=O)c1ncc(C#Cc2ccccc2)cc1F)C1(C)COC1] | 3-Fluoro-5-phenylethynyl-pyridine-2-carboxylic acid methyl-(3-methyl-oxetan-3-yl)-amide | 40 | 67 |
| 51 | 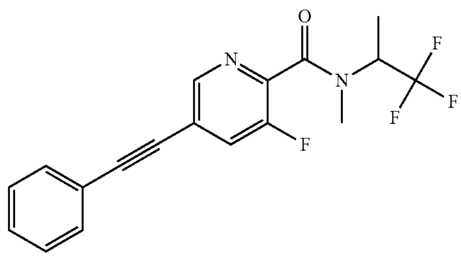 [SMILES: CC(N(C)C(=O)c1ncc(C#Cc2ccccc2)cc1F)C(F)(F)F] | (RS)-3-Fluoro-5-phenylethynyl-pyridine-2-carboxylic acid methyl-(2,2,2-trifluoro-1-methyl-ethyl)-amide | 66 | 69 |
| 52 | 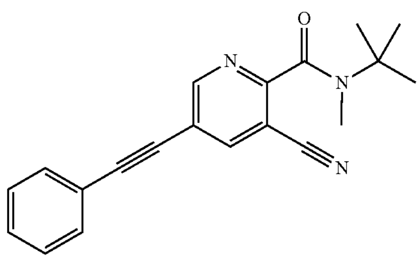 [SMILES: CN(C(=O)c1ncc(C#Cc2ccccc2)cc1C#N)C(C)(C)C] | 3-Cyano-5-phenylethynyl-pyridine-2-carboxylic acid tert-butyl-methyl-amide | 34 | 96 |
| 53 | 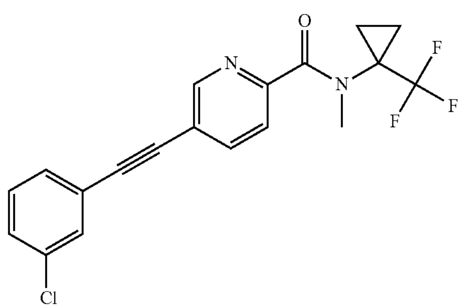 [SMILES: CN(C(=O)c1ccc(C#Cc2cccc(Cl)c2)cn1)C1(C(F)(F)F)CC1] | 5-(5-Chloro-pyridin-3-ylethynyl)-pyridine-2-carboxylic acid methyl-(1-trifluoromethyl-cyclopropyl)-amide | 44 | 57 |
| 54 | 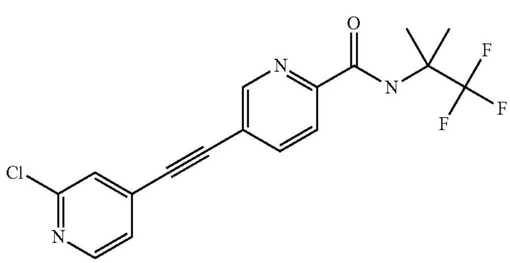 [SMILES: CC(C)(NC(=O)c1ccc(C#Cc2ccnc(Cl)c2)cn1)C(F)(F)F] | 5-(2-Chloro-pyridin-4-ylethynyl)-pyridine-2-carboxylic acid (2,2,2-trifluoro-1,1-dimethyl-ethyl)-amide | 37 | 80 |

-continued

| Ex. | Structure | Name | EC$_{50}$ (nM) mGlu5PAM | Eff. (%) |
|---|---|---|---|---|
| 55 | 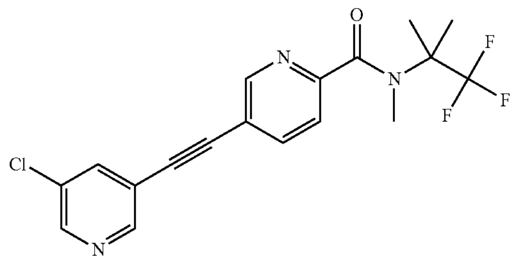 [SMILES: CN(C(=O)c1ccc(C#Cc2cncc(Cl)c2)cn1)C(C)(C)C(F)(F)F] | 5-(5-Chloro-pyridin-3-ylethynyl)-pyridine-2-carboxylic acid methyl-(2,2,2-trifluoro-1,1-dimethyl-ethyl)-amide | 37 | 63 |
| 56 | 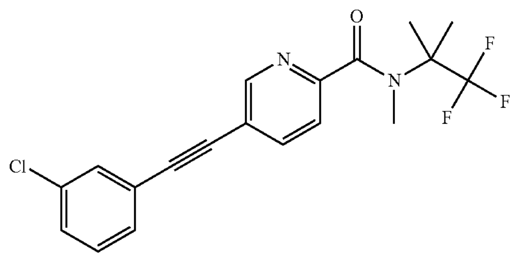 [SMILES: CN(C(=O)c1ccc(C#Cc2cccc(Cl)c2)cn1)C(C)(C)C(F)(F)F] | 5-(3-Chloro-phenylethynyl)-pyridine-2-carboxylic acid methyl-(2,2,2-trifluoro-1,1-dimethyl-ethyl)-amide | 22 | 29 |
| 57 | 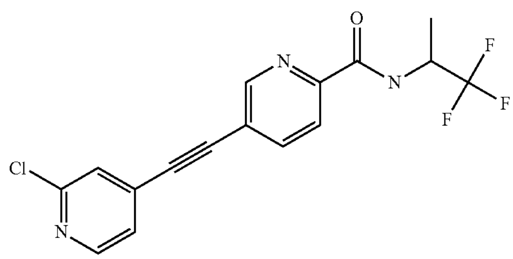 [SMILES: CC(NC(=O)c1ccc(C#Cc2ccnc(Cl)c2)cn1)C(F)(F)F] | (RS)-5-(2-Chloro-pyridin-4-ylethynyl)-pyridine-2-carboxylic acid (2,2,2-trifluoro-1-methyl-ethyl)-amide | 22 | 42 |
| 58 | 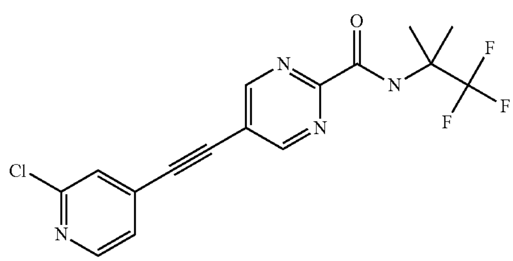 [SMILES: CC(C)(NC(=O)c1ncc(C#Cc2ccnc(Cl)c2)cn1)C(F)(F)F] | 5-(2-Chloro-pyridin-4-ylethynyl)-pyrimidine-2-carboxylic acid (2,2,2-trifluoro-1,1-dimethyl-ethyl)-amide | 57 | 30 |
| 59 | | (R) or (S)-5-(2-Chloro-pyridin-4-ylethynyl)-pyridine-2-carboxylic acid (2,2,2-trifluoro-1-methyl-ethyl)-amide | 27 | 47 |

OR

| Ex. | Structure | Name | EC$_{50}$ (nM) mGlu5PAM | Eff. (%) |
|---|---|---|---|---|
| 60 | 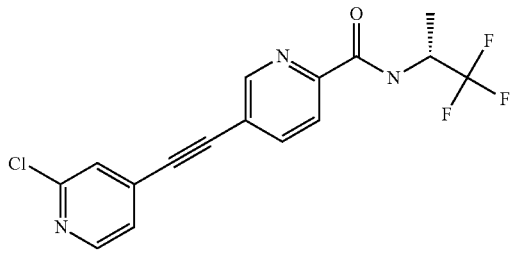 OR 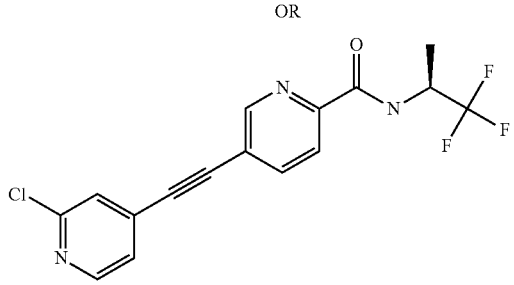 | (S) or (R)-5-(2-Chloro-pyridin-4-ylethynyl)-pyridine-2-carboxylic acid (2,2,2-trifluoro-1-methyl-ethyl)-amide | 69 | 60 |
| 61 | 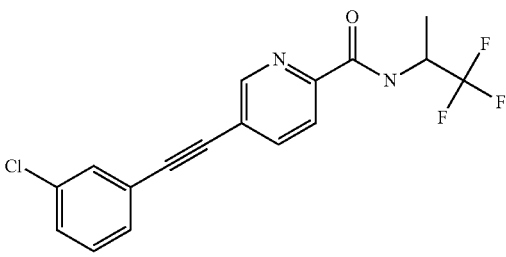 | (RS)-5-(3-Chloro-phenylethynyl)-pyridine-2-carboxylic acid (2,2,2-trifluoro-1-methyl-ethyl)-amide | 61 | 83 |
| 62 | 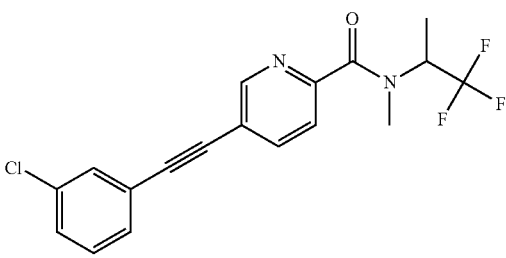 | (RS)-5-(3-Chloro-phenylethynyl)-pyridine-2-carboxylic acid methyl-(2,2,2-trifluoro-1-methyl-ethyl)-amide | 25 | 35 |
| 63 | 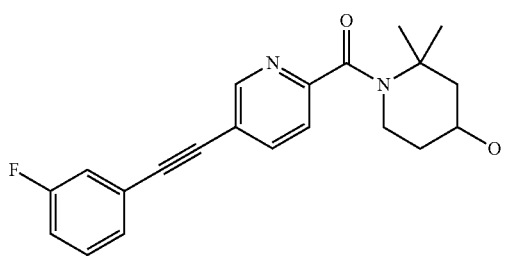 | (RS)-[5-(3-Fluoro-phenylethynyl)-pyridin-2-yl]-(4-hydroxy-2,2-dimethyl-piperidin-1-yl)-methanone | 40 | 45 |

-continued

| Ex. | Structure | Name | EC$_{50}$ (nM) mGlu5PAM | Eff. (%) |
|---|---|---|---|---|
| 64 | 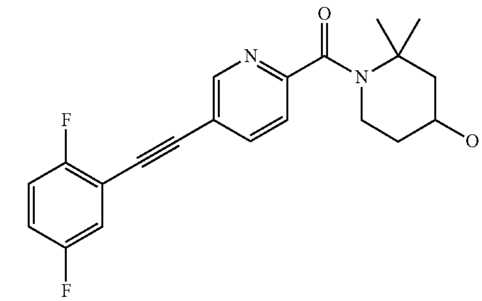 [SMILES: CC1(C)CC(O)CCN1C(=O)c1ccc(C#Cc2cc(F)ccc2F)cn1] | (RS)-[5-(2,5-Difluoro-phenylethynyl)-pyridin-2-yl]-(4-hydroxy-2,2-dimethyl-piperidin-1-yl)-methanone | 34 | 42 |
| 65 | 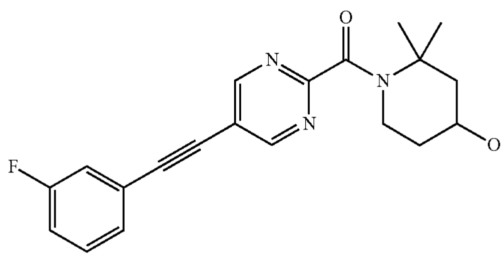 [SMILES: CC1(C)CC(O)CCN1C(=O)c1ncc(C#Cc2cccc(F)c2)cn1] | (RS)-[5-(3-Fluoro-phenylethynyl)-pyrimidin-2-yl]-(4-hydroxy-2,2-dimethyl-piperidin-1-yl)-methanone | 149 | 55 |
| 66 | 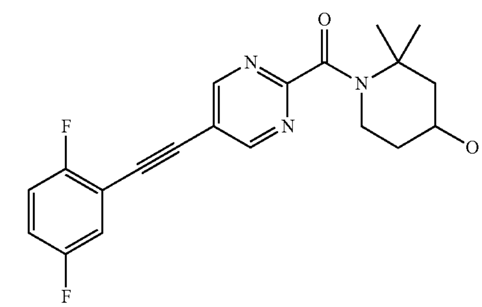 [SMILES: CC1(C)CC(O)CCN1C(=O)c1ncc(C#Cc2cc(F)ccc2F)cn1] | (RS)-[5-(2,5-Difluoro-phenylethynyl)-pyrimidin-2-yl]-(4-hydroxy-2,2-dimethyl-piperidin-1-yl)-methanone | 101 | 49 |
| 67 | 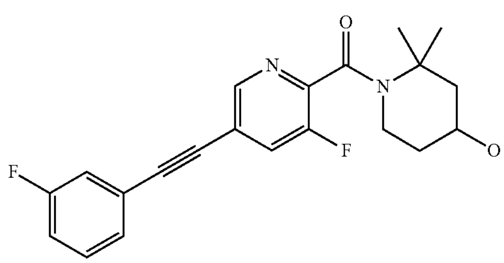 [SMILES: CC1(C)CC(O)CCN1C(=O)c1ncc(C#Cc2cccc(F)c2)cc1F] | (RS)-[3-Fluoro-5-(3-fluoro-phenylethynyl)-pyridin-2-yl]-(4-hydroxy-2,2-dimethyl-piperidin-1-yl)-methanone | 54 | 57 |
| 68 | 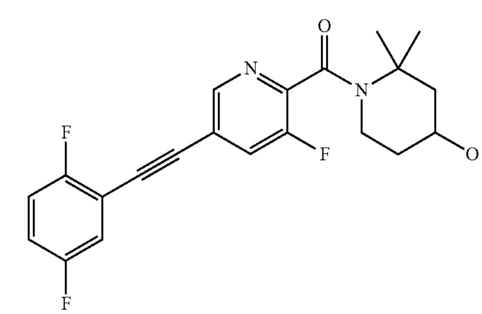 [SMILES: CC1(C)CC(O)CCN1C(=O)c1ncc(C#Cc2cc(F)ccc2F)cc1F] | (RS)-[5-(2,5-Difluoro-phenylethynyl)-3-fluoro-pyridin-2-yl]-(4-hydroxy-2,2-dimethyl-piperidin-1-yl)-methanone | 46 | 54 |

The compounds of formula (I) and pharmaceutically acceptable salts thereof can be used as therapeutics, e.g. in the form of pharmaceutical compositions. The pharmaceutical compositions can be administered orally, e.g. in the form of tablets, coated tablets, dragées, hard and soft gelatin capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, the invention provides pharmaceutical compositions containing a compound of formula (I) or pharmaceutically acceptable salts thereof and a therapeutically inert excipient, a process for the production of such pharmaceutical compositions which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the present invention provides the use of the compounds of formula (I) for the preparation of medicaments useful in the prevention and/or the treatment of the above recited diseases.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention Example A Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXPERIMENTAL SECTION

Example 1

5-Phenylethynyl-pyridine-2-carboxylic Acid tert-butylamide

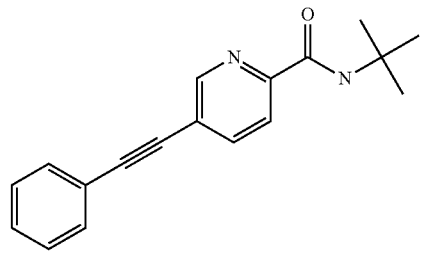 [SMILES: CC(C)(C)NC(=O)c1ccc(C#Cc2ccccc2)cn1]

Step 1: 5-Bromo-pyridine-2-carboxylic Acid tert-butylamide

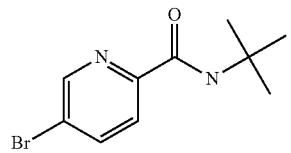

5-Bromopicolinic acid (200 mg, 0.99 mmol) was dissolved in dioxane (2 ml) and Hunig's Base (520 µl, 2.97 mmol, 3 equiv.), TBTU (350 mg, 1.09 mmol, 1.1 equiv.) and tert-butyl amine (124 µl, 1.19 mmol, 1.2 equiv.) were added at room temperature. The mixture was stirred for 16 hours at room temperature. The reaction mixture was evaporated and extracted saturated NaHCO₃ solution and two times with a small volume of dichloromethane. The crude product was purified by flash chromatography by directly loading the dichloromethane layers onto a silica gel column and eluting with an ethyl acetate:heptane gradient 0:100 to 50:50. The desired 5-bromo-pyridine-2-carboxylic acid tert-butylamide (235 mg, 92% yield) was obtained as a colorless oil, MS: m/e=257.0/259.0 (M+H+).

Step 2: 5-Phenylethynyl-pyridine-2-carboxylic Acid tert-butylamide

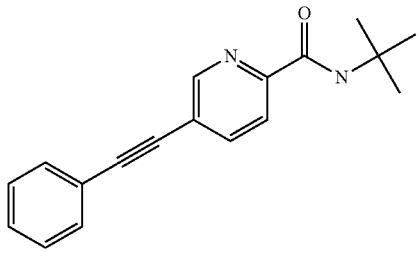 [SMILES: CC(C)(C)NC(=O)c1ccc(C#Cc2ccccc2)cn1]

Bis-(triphenylphosphine)-palladium(II)dichloride (31 mg, 44.7 µmol, 0.05 equiv.) was dissolved in 2 ml DMF. (230 mg, 894 µmol) 5-Bromo-pyridine-2-carboxylic acid tert-butylamide (Example 1, step 1) and phenylacetylene (183 mg, 196 µl, 1.79 mmol, 2 equiv.) were added at room temperature. Triethylamine (272 mg, 374 µl, 2.68 mmol, 3 equiv.), triphenylphosphine (7 mg, 26.8 µmol, 0.03 equiv.) and copper(I) iodide (5 mg, 26.8 µmol, 0.03 equiv.) were added and the mixture was stirred for 2 hours at 70° C. The reaction mixture was cooled and extracted with saturated NaHCO₃ solution and two times with a small volume of dichloromethane. The crude product was purified by flash chromatography by directly loading the dichloromethane layers onto a silica gel column eluting with an ethyl acetate:heptane gradient 0:100 to 100:0. The desired 5-phenylethynyl-pyridine-2-carboxylic acid tert-butylamide (174 mg, 70% yield) was obtained as a light yellow solid, MS: m/e=279.1 (M+H+).

Example 2

5-Phenylethynyl-pyridine-2-carboxylic Acid tert-butyl-methyl-amide

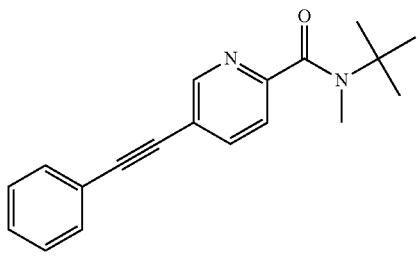 [SMILES: CN(C(=O)c1ccc(C#Cc2ccccc2)cn1)C(C)(C)C]

(74 mg, 266 µmol) 5-Phenylethynyl-pyridine-2-carboxylic acid tert-butylamide (Example 1, step 2) was dissolved in DMF (1 ml) and cooled to 0-5° C. NaH (55%) (14 mg, 319 µmol, 1.2 equiv.) was added and the mixture was stirred for 30 min at 0-5° C. Iodomethane (22 µl, 346 µmol, 1.3 equiv.) was added, and the mixture was then stirred for 1 hour at room temperature. The reaction mixture was evaporated and treated with sat. NaHCO₃ solution and extracted twice with a small volume of CH₂Cl₂. The organic layers were loaded directly to silica gel column and the crude material was purified by flash chromatography on silica gel (20 g, ethyl acetate/heptane gradient, 0:100 to 100:0). The desired 5-phenylethynyl-pyridine-2-carboxylic acid tert-butyl-methyl-amide (48 mg, 62% yield) was obtained as a light yellow solid, MS: m/e=293.0 (M+H+).

Example 3

5-(3-Fluoro-phenylethynyl)-pyridine-2-carboxylic Acid tert-butyl-methyl-amide

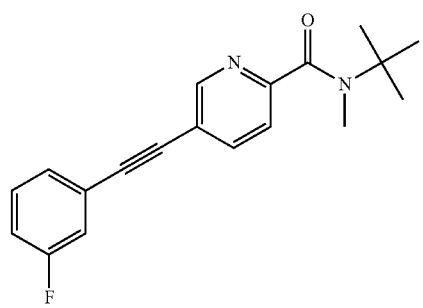 [SMILES: CN(C(=O)c1ccc(C#Cc2cccc(F)c2)cn1)C(C)(C)C]

Step 1: 5-Bromo-pyridine-2-carboxylic Acid tert-butyl-methyl-amide

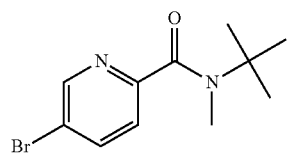

The title compound was obtained as a white solid, MS: m/e=271.2/273.2 (M+H+), using chemistry similar to that described in Example 2 from 5-bromo-pyridine-2-carboxylic acid tert-butylamide (Example 1, step 1) and iodomethane.

Step 2: 5-Trimethylsilanylethynyl-pyridine-2-carboxylic Acid tert-butyl-methyl-amide

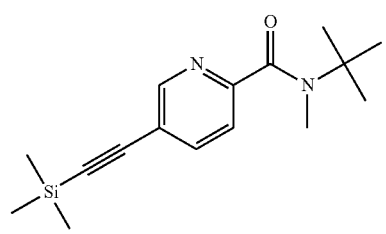 [SMILES: CN(C(=O)c1ccc(C#C[Si](C)(C)C)cn1)C(C)(C)C]

The title compound was obtained as a yellow solid, MS: m/e=289.2 (M+H+), using chemistry similar to that described in Example 1, step 2 from 5-bromo-pyridine-2-carboxylic acid tert-butyl-methyl-amide (Example 3, step 1) and ethynyltrimethylsilane.

Step 3: 5-(3-Fluoro-phenylethynyl)-pyridine-2-carboxylic Acid tert-butyl-methyl-amide

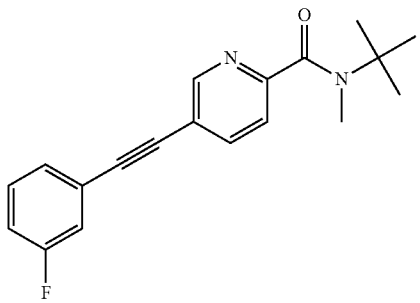

5-Trimethylsilanylethynyl-pyridine-2-carboxylic acid tert-butyl-methyl-amide (Example 3, step 2) (60 mg, 0.2 mmol) was dissolved in DMF (1 ml). 1-Fluoro-3-iodobenzene (74 mg, 0.33 mmol, 1.6 equiv.), Et$_3$N (87 µl, 0.62 mmol, 3 equiv.), Bis-(triphenylphosphine)-palladium(II)dichloride (7 mg, 10.4 µmol, 0.05 equiv.) and copper(I)iodide (0.4 mg, 2 µmol, 0.01 equiv.) were added under nitrogen and the mixture was heated to 70° C. TBAF 1M in THF (230 µl, 0.23 mmol, 1.1 equiv.) was added dropwise over a period of 20 minutes at 70° C. The reaction mixture was stirred for 30 minutes at 70° C. and evaporated in presence of Isolute® sorbent to dryness. The crude product was purified by flash chromatography with a 20 g silica gel column eluting with heptane:ethyl acetate 100:0→70:30. The desired 5-(3-fluoro-phenylethynyl)-pyridine-2-carboxylic acid tert-butyl-methyl-amide (64 mg, 99% yield) was obtained as a colorless oil, MS: m/e=311.5 (M+H$^+$).

Example 4

5-(4-Fluoro-phenylethynyl)-pyridine-2-carboxylic Acid tert-butyl-methyl-amide

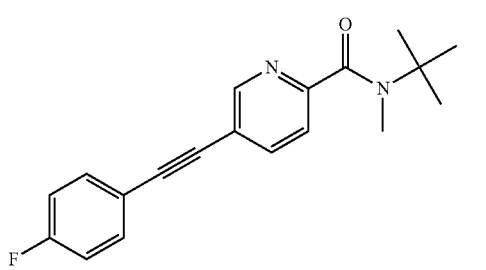

The title compound was obtained as a light yellow solid, MS: m/e=311.5 (M+H$^+$), using chemistry similar to that described in Example 3, step 3 from 5-trimethylsilanylethynyl-pyridine-2-carboxylic acid tert-butyl-methyl-amide (Example 3, step 2) and 1-fluoro-4-iodobenzene.

Example 5

5-(2,5-Difluoro-phenylethynyl)-pyridine-2-carboxylic Acid tert-butyl-methyl-amide

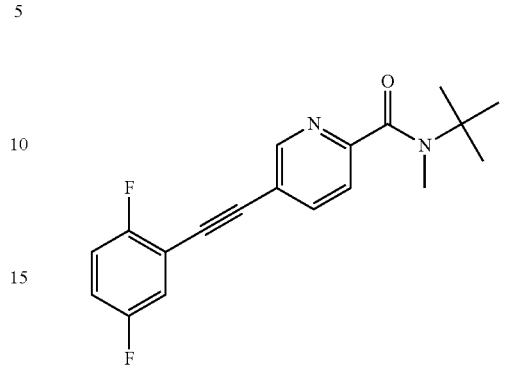

The title compound was obtained as a light yellow solid, MS: m/e=329.1 (M+H$^+$), using chemistry similar to that described in Example 3, step 3 from 5-trimethylsilanylethynyl-pyridine-2-carboxylic acid tert-butyl-methyl-amide (Example 3, step 2) and 1,4-difluoro-2-iodobenzene.

Example 6

5-Pyridin-3-ylethynyl-pyridine-2-carboxylic Acid tert-butyl-methyl-amide

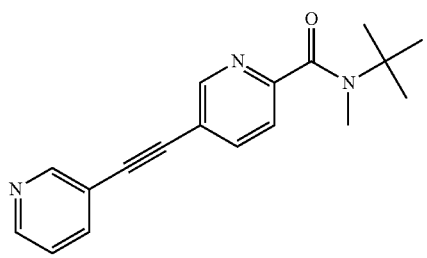 [SMILES: CN(C(=O)c1ccc(C#Cc2cccnc2)cn1)C(C)(C)C]

The title compound was obtained as a light yellow solid, MS: m/e=294.1 (M+H$^+$), using chemistry similar to that described in Example 3, step 3 from 5-trimethylsilanylethynyl-pyridine-2-carboxylic acid tert-butyl-methyl-amide (Example 3, step 2) and 3-iodopyridine.

Example 7

5-(5-Chloro-pyridin-3-ylethynyl)-pyridine-2-carboxylic Acid tert-butyl-methyl-amide

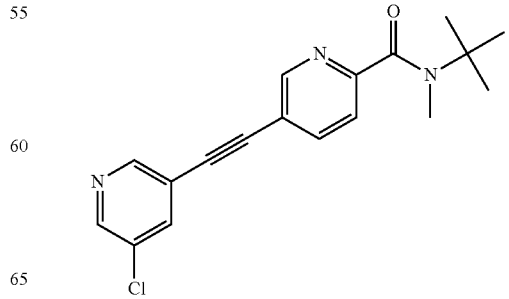

The title compound was obtained as a white solid, MS: m/e=328.1/330.0 (M+H$^+$), using chemistry similar to that described in Example 3, step 3 from 5-trimethylsilanylethynyl-pyridine-2-carboxylic acid tert-butyl-methyl-amide (Example 3, step 2) and 3-chloro-5-iodopyridine.

Example 8

5-(5-Fluoro-pyridin-3-ylethynyl)-pyridine-2-carboxylic Acid tert-butyl-methyl-amide

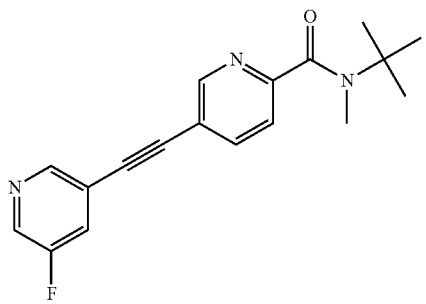

The title compound was obtained as a white solid, MS: m/e=312.2 (M+H$^+$), using chemistry similar to that described in Example 3, step 3 from 5-trimethylsilanylethynyl-pyridine-2-carboxylic acid tert-butyl-methyl-amide (Example 3, step 2) and 3-fluoro-5-iodopyridine.

Example 9

5-(4-Fluoro-phenylethynyl)-pyrimidine-2-carboxylic Acid tert-butylamide

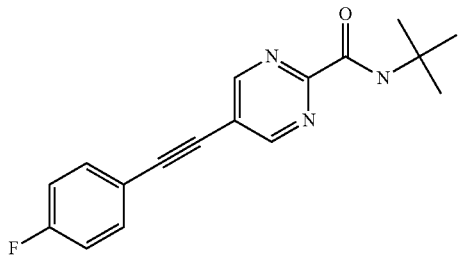

Step 1: 5-Bromo-pyrimidine-2-carboxylic Acid tert-butylamide

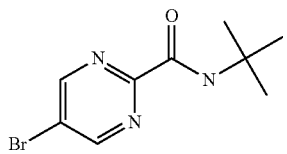

5-Bromopyrimidine-2-carboxylic acid (1 g, 4.93 mmol) was suspended in dichloromethane (10 ml) and DMF (20 μl). Oxalyl chloride (520 μl, 5.91 mmol, 1.2 equiv.) was added drop wise at room temperature and the mixture was stirred for 16 hours. The reaction mixture was then cooled to 0-5° C. and pyridine (480 μl, 5.91 mmol, 1.2 equiv.) and tert-butyl amine (621 μl, 5.91 mmol, 1.2 equiv.) were added drop wise at 0-5° C. The mixture was stirred for 4 hours at room temperature. The reaction mixture was extracted with saturated NaHCO$_3$ solution and dichloromethane. The organic layers were extracted with water and brine, dried over sodium sulfate and evaporated to dryness. The desired 5-bromo-pyrimidine-2-carboxylic acid tert-butylamide (960 mg, 76% yield) was obtained as a light yellow solid, MS: m/e=258.0/259.9 (M+H$^+$).

Step 2: 5-Iodo-pyrimidine-2-carboxylic Acid tert-butylamide

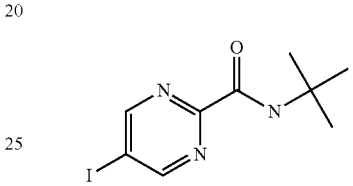

5-Bromo-pyrimidine-2-carboxylic acid tert-butylamide (Example 9, step 1) (950 mg, 3.68 mmol) was dissolved in dioxane (10 ml). Sodium iodide (2.2 g, 14.7 mmol, 4 equiv.), copper(I)iodide (66 mg, 0.74 mmol, 0.2 equiv.) and trans-N,N'-dimethylcyclohexane-1,2-diamine (CAS 67579-81-1) (105 mg, 0.74 mmol, 0.2 equiv.) were added and the mixture was stirred for 16 hours at 100° C. The reaction mixture was extracted with saturated NaHCO$_3$ solution and two times with ethyl acetate. The organic layers were extracted with brine, dried over sodium sulfate and evaporated to dryness. The crude product was purified by flash chromatography with a 20 g silica gel column and eluting with heptane:ethyl acetate 100:0→0:100. The desired 5-iodo-pyrimidine-2-carboxylic acid tert-butylamide (870 mg, 78% yield) was obtained as a yellow solid, MS: m/e=306.0 (M+H$^+$).

Step 3: 5-(4-Fluoro-phenylethynyl)-pyrimidine-2-carboxylic Acid tert-butylamide

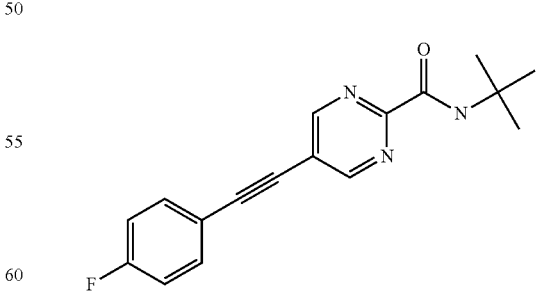

The title compound was obtained as a yellow solid, MS: m/e=298.4 (M+H$^+$), using chemistry similar to that described in Example 1, step 2 from 5-iodo-pyrimidine-2-carboxylic acid tert-butylamide (Example 9, step 2) and 1-ethynyl-4-fluoro-benzene.

Example 10

5-(3-Fluoro-phenylethynyl)-pyrimidine-2-carboxylic Acid tert-butylamide

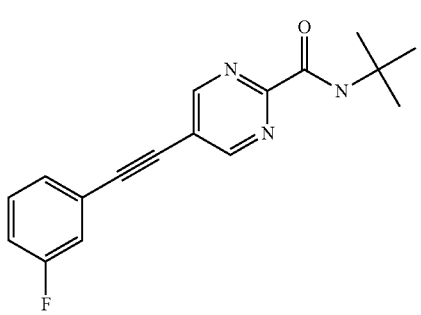

The title compound was obtained as a yellow solid, MS: m/e=298.5 (M+H$^+$), using chemistry similar to that described in Example 1, step 2 from 5-iodo-pyrimidine-2-carboxylic acid tert-butylamide (Example 9, step 2) and 1-ethynyl-3-fluoro-benzene.

Example 11

5-(4-Fluoro-phenylethynyl)-pyrimidine-2-carboxylic Acid tert-butyl-methyl-amide

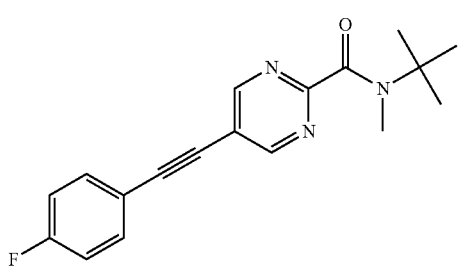

Step 1: 5-Bromo-pyrimidine-2-carboxylic Acid tert-butyl-methyl-amide

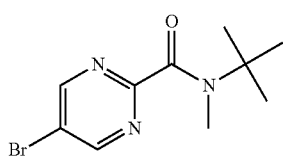

The title compound was obtained as a white solid, MS: m/e=272.2/274.1 (M+H$^+$), using chemistry similar to that described in Example 9, step 1 from 5-bromopyrimidine-2-carboxylic acid and tert-butyl-methyl-amine.

Step 2: 5-Iodo-pyrimidine-2-carboxylic Acid tert-butyl-methyl-amide

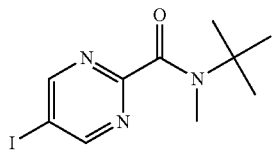

The title compound was obtained as a white solid, MS: m/e=319.9 (M+H$^+$), using chemistry similar to that described in Example 9, step 2 from 5-bromo-pyrimidine-2-carboxylic acid tert-butyl-methyl-amide (Example 11, step 1).

Step 3: 5-(4-Fluoro-phenylethynyl)-pyrimidine-2-carboxylic Acid tert-butyl-methyl-amide

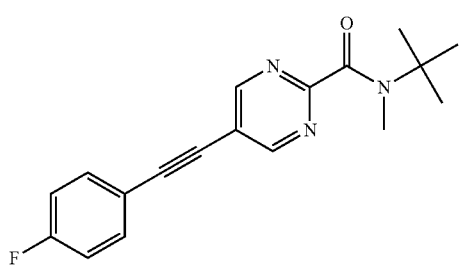 [SMILES: CN(C(=O)c1ncc(C#Cc2ccc(F)cc2)cn1)C(C)(C)C]

The title compound was obtained as a yellow solid, MS: m/e=312.3 (M+H$^+$), using chemistry similar to that described in Example 1, step 2 from 5-iodo-pyrimidine-2-carboxylic acid tert-butyl-methyl-amide (Example 11, step 2) and 1-ethynyl-4-fluoro-benzene.

Example 12

5-(3-Fluoro-phenylethynyl)-pyrimidine-2-carboxylic Acid tert-butyl-methyl-amide

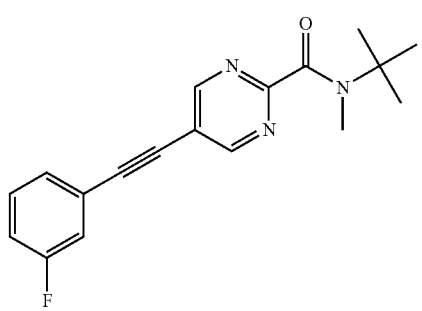 [SMILES: CN(C(=O)c1ncc(C#Cc2cccc(F)c2)cn1)C(C)(C)C]

The title compound was obtained as a light brown solid, MS: m/e=312.2 (M+H$^+$), using chemistry similar to that described in Example 1, step 2 from 5-iodo-pyrimidine-2-carboxylic acid tert-butyl-methyl-amide (Example 11, step 2) and 1-ethynyl-3-fluoro-benzene.

Example 13

5-m-Tolylethynyl-pyrimidine-2-carboxylic Acid tert-butylamide

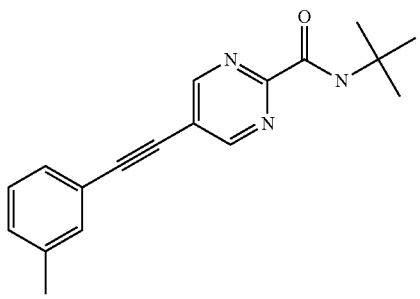 [SMILES: Cc1cccc(C#Cc2cnc(C(=O)NC(C)(C)C)nc2)c1]

The title compound was obtained as an orange oil, MS: m/e=294.0 (M+H$^+$), using chemistry similar to that described in Example 1, step 2 from 5-iodo-pyrimidine-2-carboxylic acid tert-butylamide (Example 9, step 2) and 1-ethynyl-3-methyl-benzene.

Example 14

5-(3-Chloro-phenylethynyl)-pyrimidine-2-carboxylic Acid tert-butylamide

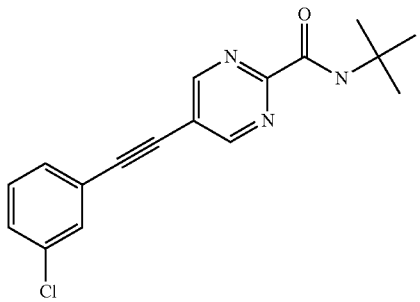

The title compound was obtained as a light yellow solid, MS: m/e=314.0/316.0 (M+H$^+$), using chemistry similar to that described in Example 1, step 2 from 5-iodo-pyrimidine-2-carboxylic acid tert-butylamide (Example 9, step 2) and 1-chloro-3-ethynylbenzene.

Example 15

5-(2,5-Difluoro-phenylethynyl)-pyrimidine-2-carboxylic Acid tert-butyl-methyl-amide

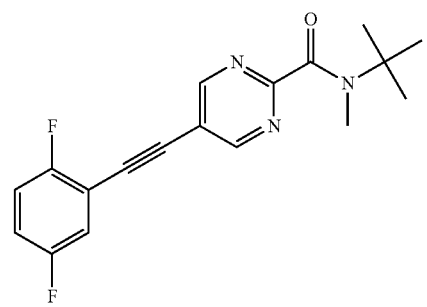 [SMILES: CN(C(=O)c1ncc(C#Cc2cc(F)ccc2F)cn1)C(C)(C)C]

Step 1:
5-Trimethylsilanylethynyl-pyrimidine-2-carboxylic Acid tert-butyl-methyl-amide

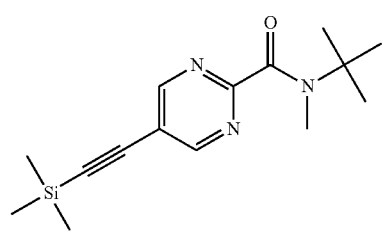 [SMILES: CN(C(=O)c1ncc(C#C[Si](C)(C)C)cn1)C(C)(C)C]

The title compound was obtained as an orange solid, MS: m/e=290.1 (M+H$^+$), using chemistry similar to that described in Example 1, step 2 from 5-iodo-pyrimidine-2-carboxylic acid tert-butyl-methyl-amide (Example 11, step 2) and ethynyltrimethylsilane.

Step 2: 5-(2,5-Difluoro-phenylethynyl)-pyrimidine-2-carboxylic Acid tert-butyl-methyl-amide

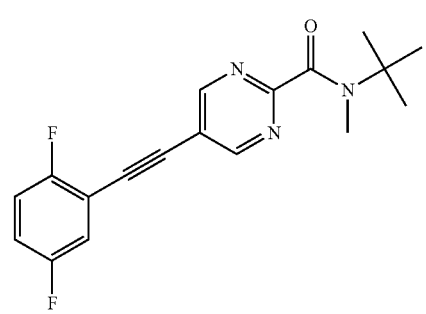 [SMILES: CN(C(=O)c1ncc(C#Cc2cc(F)ccc2F)cn1)C(C)(C)C]

The title compound was obtained as a light yellow solid, MS: m/e=312.3 (M+H$^+$), using chemistry similar to that described in Example 3, step 3 from 5-trimethylsilanylethynyl-pyrimidine-2-carboxylic acid tert-butyl-methyl-amide (Example 15, step 1) and 1,4-difluoro-2-iodobenzene.

Example 16

5-(5-Chloro-pyridin-3-ylethynyl)-pyrimidine-2-carboxylic Acid tert-butyl-methyl-amide

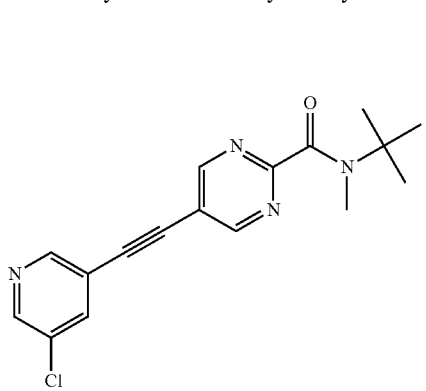

The title compound was obtained as a light yellow solid, MS: m/e=329.0/331.2 (M+H$^+$), using chemistry similar to that described in Example 3, step 3 from 5-trimethylsilanyl-ethynyl-pyrimidine-2-carboxylic acid tert-butyl-methyl-amide (Example 15, step 1) and 3-chloro-5-iodopyridine.

Example 17

5-(3-Fluoro-phenylethynyl)-3-methyl-pyridine-2-carboxylic Acid tert-butyl-methyl-amide

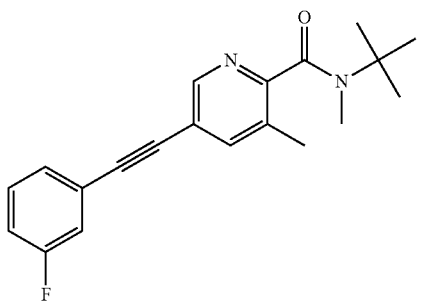 [SMILES: Cc1cc(C#Cc2cccc(F)c2)cnc1C(=O)N(C)C(C)(C)C]

Step 1: 5-Bromo-3-methyl-pyridine-2-carboxylic Acid tert-butyl-methyl-amide

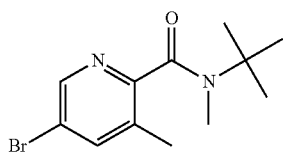 [SMILES: Cc1cc(Br)cnc1C(=O)N(C)C(C)(C)C]

The title compound was obtained as a yellow oil, MS: m/e=285.0/286.9 (M+H$^+$), using chemistry similar to that described in Example 9, step 1 from 5-bromo-3-methylpicolinic acid and tert-butyl-methyl-amine.

Step 2: 5-(3-Fluoro-phenylethynyl)-3-methyl-pyridine-2-carboxylic Acid tert-butyl-methyl-amide

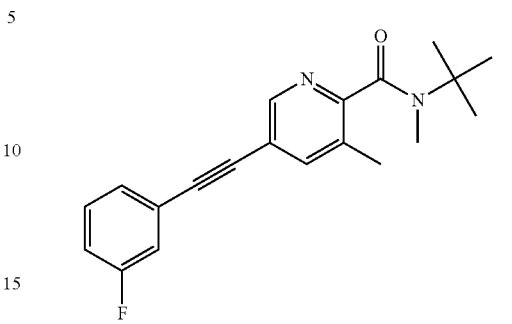

The title compound was obtained as a yellow solid, MS: m/e=325.3 (M+H$^+$), using chemistry similar to that described in Example 1, step 2 from 5-bromo-3-methyl-pyridine-2-carboxylic acid tert-butyl-methyl-amide (Example 17, step 1) and 1-ethynyl-3-fluoro-benzene.

Example 18

5-(4-Fluoro-phenylethynyl)-3-methyl-pyridine-2-carboxylic Acid tert-butyl-methyl-amide

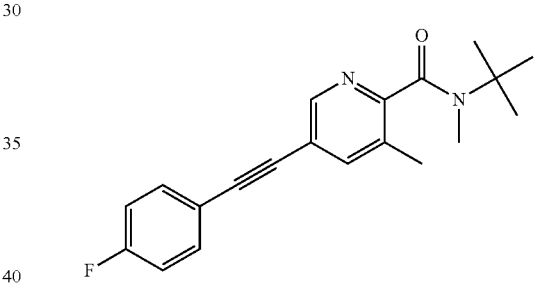

The title compound was obtained as a yellow solid, MS: m/e=325.3 (M+H$^+$), using chemistry similar to that described in Example 1, step 2 from 5-bromo-3-methyl-pyridine-2-carboxylic acid tert-butyl-methyl-amide (Example 17, step 1) and 1-ethynyl-4-fluoro-benzene.

Example 19

5-(2,5-Difluoro-phenylethynyl)-3-methyl-pyridine-2-carboxylic Acid tert-butyl-methyl-amide

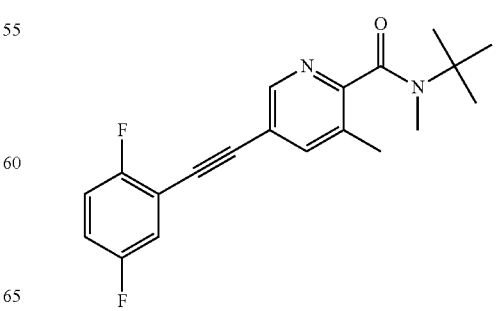

Step 1: 3-Methyl-5-trimethylsilanylethynyl-pyridine-2-carboxylic Acid tert-butyl-methyl-amide

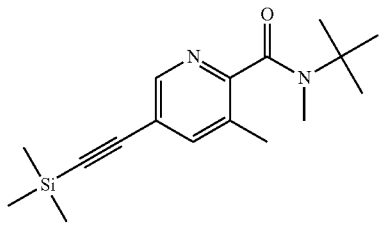 [SMILES: Cc1cc(C#C[Si](C)(C)C)cnc1C(=O)N(C)C(C)(C)C]

The title compound was obtained as a brown solid, MS: m/e=303.0 (M+H⁺), using chemistry similar to that described in Example 1, step 2 from 5-bromo-3-methyl-pyridine-2-carboxylic acid tert-butyl-methyl-amide (Example 17, step 1) and ethynyltrimethylsilane.

Step 2: 5-(2,5-Difluoro-phenylethynyl)-3-methyl-pyridine-2-carboxylic Acid tert-butyl-methyl-amide

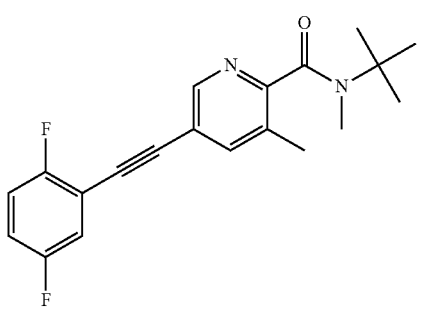

The title compound was obtained as a white solid, MS: m/e=343.1 (M+H⁺), using chemistry similar to that described in Example 3, step 3 from 3-methyl-5-trimethylsilanylethynyl-pyridine-2-carboxylic acid tert-butyl-methyl-amide (Example 19, step 1) and 1,4-difluoro-2-iodobenzene.

Example 20

5-(5-Chloro-pyridin-3-ylethynyl)-3-methyl-pyridine-2-carboxylic Acid tert-butyl-methyl-amide

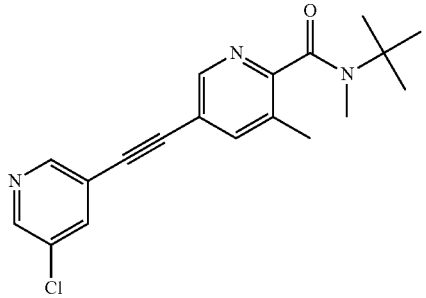 [SMILES: Cc1cc(C#Cc2cncc(Cl)c2)cnc1C(=O)N(C)C(C)(C)C]

The title compound was obtained as a yellow solid, MS: m/e=342.1/344.0 (M+H⁺), using chemistry similar to that described in Example 3, step 3 from 3-methyl-5-trimethylsilanylethynyl-pyridine-2-carboxylic acid tert-butyl-methyl-amide (Example 19, step 1) and 3-chloro-5-iodopyridine.

Example 21

3-Fluoro-5-(3-fluoro-phenylethynyl)-pyridine-2-carboxylic Acid tert-butyl-methyl-amide

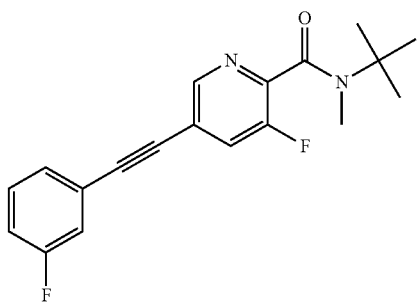 [SMILES: CN(C(=O)c1ncc(C#Cc2cccc(F)c2)cc1F)C(C)(C)C]

Step 1: 5-Bromo-3-fluoro-pyridine-2-carboxylic Acid tert-butyl-methyl-amide

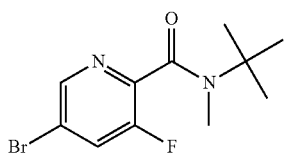 [SMILES: CN(C(=O)c1ncc(Br)cc1F)C(C)(C)C]

The title compound was obtained as a light yellow oil, MS: m/e=288.9/290.9 (M+H⁺), using chemistry similar to that described in Example 9, step 1 from 5-bromo-3-fluoropicolinic acid and tert-butyl-methyl-amine.

Step 2: 3-Fluoro-5-(3-fluoro-phenylethynyl)-pyridine-2-carboxylic Acid tert-butyl-methyl-amide

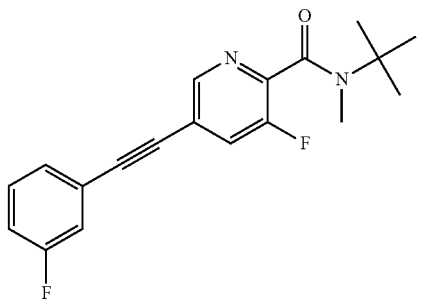 [SMILES: CN(C(=O)c1ncc(C#Cc2cccc(F)c2)cc1F)C(C)(C)C]

The title compound was obtained as a yellow oil, MS: m/e=329.0 (M+H⁺), using chemistry similar to that described in Example 1, step 2 from 5-bromo-3-fluoro-pyridine-2-carboxylic acid tert-butyl-methyl-amide (Example 21, step 1) and 1-ethynyl-3-fluoro-benzene.

Example 22

3-Fluoro-5-(4-fluoro-phenylethynyl)-pyridine-2-carboxylic Acid tert-butyl-methyl-amide

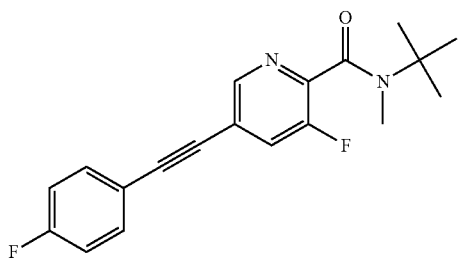

The title compound was obtained as a light yellow solid, MS: m/e=329.1 (M+H$^+$), using chemistry similar to that described in Example 1, step 2 from 5-bromo-3-fluoro-pyridine-2-carboxylic acid tert-butyl-methyl-amide (Example 21, step 1) and 1-ethynyl-4-fluoro-benzene.

Example 23

5-(2,5-Difluoro-phenylethynyl)-3-fluoro-pyridine-2-carboxylic Acid tert-butyl-methyl-amide

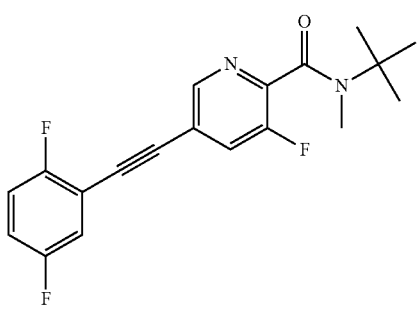

Step 1: 3-Fluoro-5-trimethylsilanylethynyl-pyridine-2-carboxylic Acid tert-butyl-methyl-amide

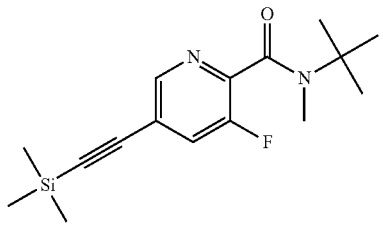 [SMILES: CN(C(=O)c1ncc(C#C[Si](C)(C)C)cc1F)C(C)(C)C]

The title compound was obtained as a light yellow solid, MS: m/e=307.3 (M+H$^+$), using chemistry similar to that described in Example 1, step 2 from 5-bromo-3-fluoro-pyridine-2-carboxylic acid tert-butyl-methyl-amide (Example 21, step 1) and ethynyltrimethylsilane.

Step 2: 5-(2,5-Difluoro-phenylethynyl)-3-fluoro-pyridine-2-carboxylic Acid tert-butyl-methyl-amide

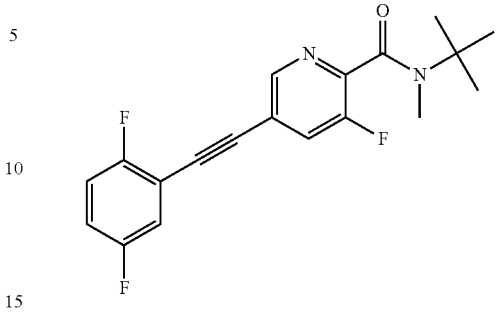

The title compound was obtained as a light yellow solid, MS: m/e=347.0 (M+H$^+$), using chemistry similar to that described in Example 3, step 3 from 3-fluoro-5-trimethylsilanylethynyl-pyridine-2-carboxylic acid tert-butyl-methyl-amide (Example 23, step 1) and 1,4-difluoro-2-iodobenzene.

Example 24

5-(5-Chloro-pyridin-3-ylethynyl)-3-fluoro-pyridine-2-carboxylic Acid tert-butyl-methyl-amide

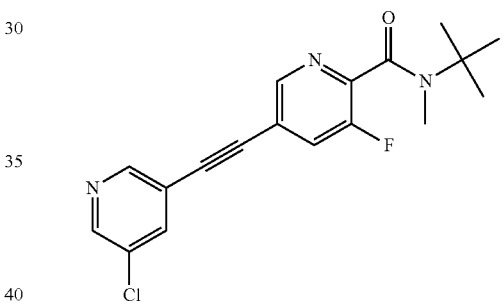

The title compound was obtained as a white solid, MS: m/e=346.0/348.0 (M+H$^+$), using chemistry similar to that described in Example 3, step 3 from 3-fluoro-5-trimethylsilanylethynyl-pyridine-2-carboxylic acid tert-butyl-methyl-amide (Example 23, step 1) and 3-chloro-5-iodopyridine.

Example 25

5-(3-Fluoro-phenylethynyl)-pyridine-2-carboxylic Acid cyclobutyl-methyl-amide

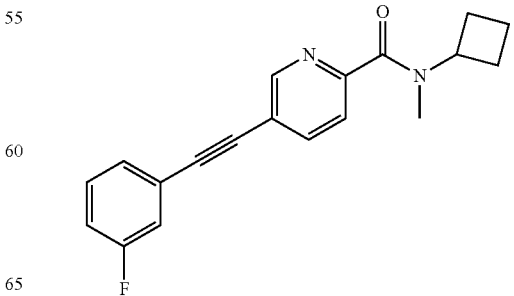

Step 1:
5-(3-Fluoro-phenylethynyl)-pyridine-2-carboxylic Acid

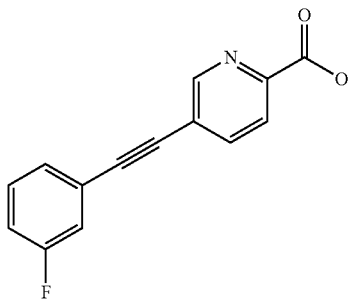 [SMILES: O=C(O)c1ccc(C#Cc2cccc(F)c2)cn1]

The title compound was obtained as a light yellow solid, MS: m/e=239.8 (M–H⁺), using chemistry similar to that described in Example 1, step 2 from 5-bromo-pyridine-2-carboxylic acid methyl ester and 1-ethynyl-3-fluoro-benzene followed by saponification with LiOH.

Step 2:
5-(3-Fluoro-phenylethynyl)-pyridine-2-carboxylic Acid Cyclobutylamide

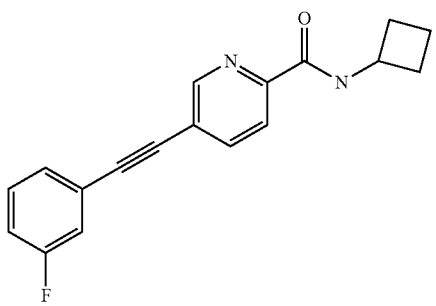 [SMILES: O=C(NC1CCC1)c1ccc(C#Cc2cccc(F)c2)cn1]

The title compound was obtained as a white solid, MS: m/e=295.1 (M+H⁺), using chemistry similar to that described in Example 1, step 1 from 5-(3-fluoro-phenylethynyl)-pyridine-2-carboxylic acid (Example 25, step 1) and cyclobutanamine.

Step 3:
5-(3-Fluoro-phenylethynyl)-pyridine-2-carboxylic Acid cyclobutyl-methyl-amide

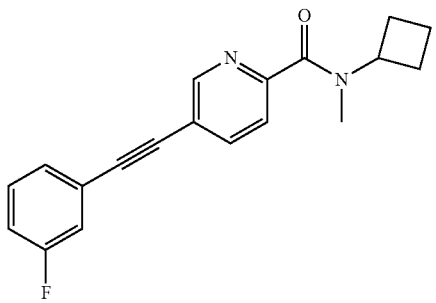 [SMILES: CN(C(=O)c1ccc(C#Cc2cccc(F)c2)cn1)C1CCC1]

The title compound was obtained as a light yellow oil, MS: m/e=309.1 (M+H⁺), using chemistry similar to that described in Example 2 from 5-(3-fluoro-phenylethynyl)-pyridine-2-carboxylic acid cyclobutylamide (Example 25, step 2) and iodomethane.

Example 26

5-(3-Fluoro-phenylethynyl)-pyridine-2-carboxylic Acid oxetan-3-ylamide

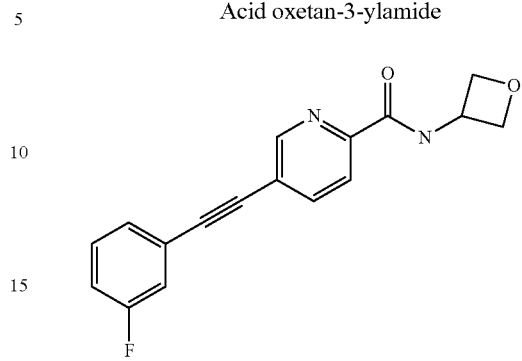

The title compound was obtained as a yellow solid, MS: m/e=297.2 (M+H⁺), using chemistry similar to that described in Example 1, step 1 from 5-(3-fluoro-phenylethynyl)-pyridine-2-carboxylic acid (Example 25, step 1) and oxetan-3-amine hydrochloride.

Example 27

5-(3-Fluoro-phenylethynyl)-pyridine-2-carboxylic Acid methyl-(3-methyl-oxetan-3-yl)-amide

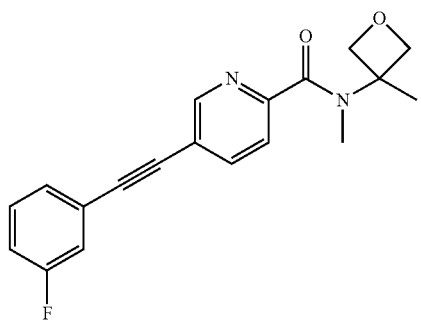 [SMILES: CN(C(=O)c1ccc(C#Cc2cccc(F)c2)cn1)C1(C)COC1]

Step 1: 5-Bromo-pyridine-2-carboxylic Acid (3-methyl-oxetan-3-yl)-amide

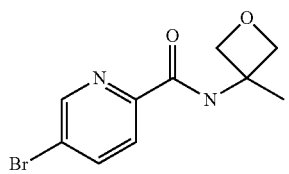

The title compound was obtained as a light yellow solid, MS: m/e=271.1/273.1 (M+H⁺), using chemistry similar to that described in Example 1, step 1 from 5-bromo-pyridine-2-carboxylic acid and 3-methyloxetan-3-amine.

Step 2: 5-Bromo-pyridine-2-carboxylic Acid methyl-(3-methyl-oxetan-3-yl)-amide

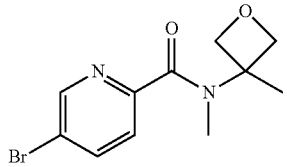 [SMILES: CN(C(=O)c1ccc(Br)cn1)C1(C)COC1]

The title compound was obtained as a white solid, MS: m/e=285.0/286.9 (M+H$^+$), using chemistry similar to that described in Example 2 from 5-bromo-pyridine-2-carboxylic acid (3-methyl-oxetan-3-yl)-amide (Example 27, step 1) and iodomethane.

Step 3: 5-(3-Fluoro-phenylethynyl)-pyridine-2-carboxylic Acid methyl-(3-methyl-oxetan-3-yl)-amide

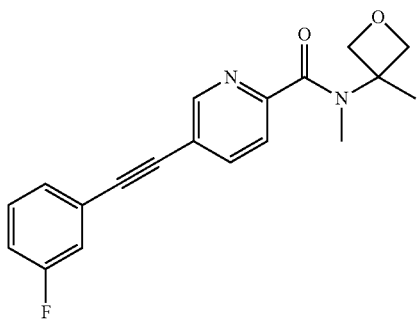 [SMILES: CN(C(=O)c1ccc(C#Cc2cccc(F)c2)cn1)C1(C)COC1]

The title compound was obtained as a brown oil, MS: m/e=325.3 (M−H$^+$), using chemistry similar to that described in Example 1, step 2 from 5-bromo-pyridine-2-carboxylic acid methyl-(3-methyl-oxetan-3-yl)-amide (Example 27, step 2) and 1-ethynyl-3-fluoro-benzene.

Example 28

5-(4-Fluoro-phenylethynyl)-pyridine-2-carboxylic Acid methyl-(3-methyl-oxetan-3-yl)-amide

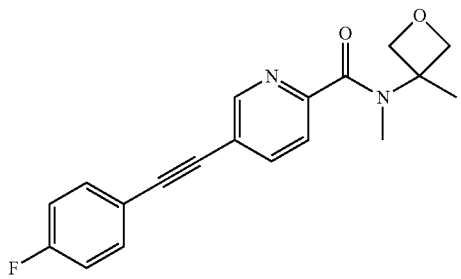

The title compound was obtained as a yellow oil, MS: m/e=325.3 (M−H$^+$), using chemistry similar to that described in Example 1, step 2 from 5-bromo-pyridine-2-carboxylic acid methyl-(3-methyl-oxetan-3-yl)-amide (Example 27, step 2) and 1-ethynyl-4-fluoro-benzene.

Example 29

5-(2,5-Difluoro-phenylethynyl)-pyridine-2-carboxylic Acid methyl-(3-methyl-oxetan-3-yl)-amide

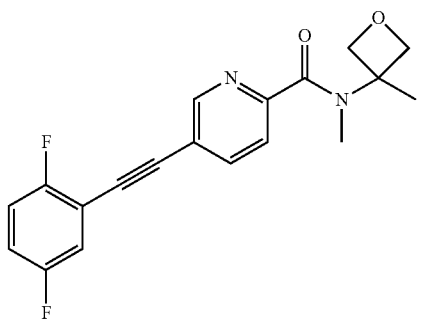 [SMILES: CN(C(=O)c1ccc(C#Cc2cc(F)ccc2F)cn1)C1(C)COC1]

Step 1: 5-Trimethylsilanylethynyl-pyridine-2-carboxylic Acid methyl-(3-methyl-oxetan-3-yl)-amide

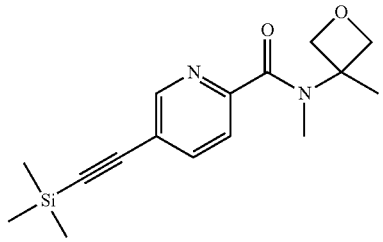

The title compound was obtained as a yellow solid, MS: m/e=303.2 (M−H$^+$), using chemistry similar to that described in Example 1, step 2 from 5-bromo-pyridine-2-carboxylic acid methyl-(3-methyl-oxetan-3-yl)-amide (Example 27, step 2) and ethynyltrimethylsilane.

Step 2: 5-(2,5-Difluoro-phenylethynyl)-pyridine-2-carboxylic Acid methyl-(3-methyl-oxetan-3-yl)-amide

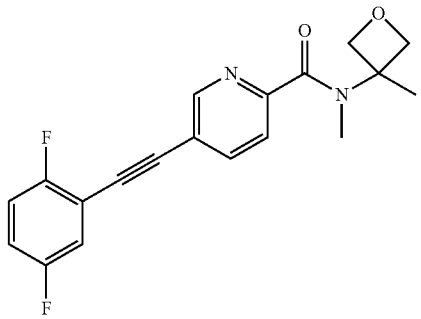 [SMILES: CN(C(=O)c1ccc(C#Cc2cc(F)ccc2F)cn1)C1(C)COC1]

The title compound was obtained as a yellow oil, MS: m/e=343.1 (M+H$^+$), using chemistry similar to that described in Example 3, step 3 from 5-trimethylsilanylethynyl-pyridine-2-carboxylic acid methyl-(3-methyl-oxetan-3-yl)-amide (Example 29, step 1) and 1,4-difluoro-2-iodobenzene.

Example 30

5-(3,4-Difluoro-phenylethynyl)-pyridine-2-carboxylic Acid methyl-(3-methyl-oxetan-3-yl)-amide

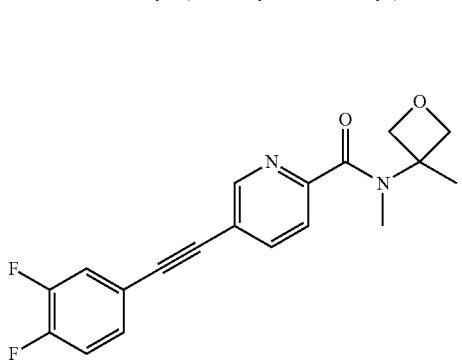

The title compound was obtained as a yellow oil, MS: m/e=343.3 (M+H⁺), using chemistry similar to that described in Example 3, step 3 from 5-trimethylsilanylethynyl-pyridine-2-carboxylic acid methyl-(3-methyl-oxetan-3-yl)-amide (Example 29, step 1) and 1,2-difluoro-4-iodobenzene.

Example 31

5-(3-Fluoro-phenylethynyl)-pyridine-2-carboxylic Acid methyl-(1-methyl-cyclopropyl)-amide

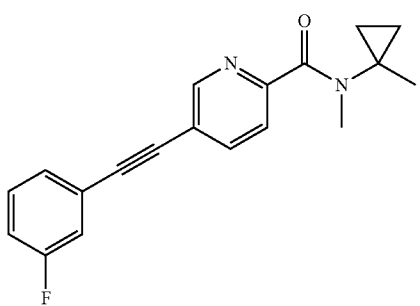 [SMILES: CN(C(=O)c1ccc(C#Cc2cccc(F)c2)cn1)C1(C)CC1]

Step 1: 5-Bromo-pyridine-2-carboxylic Acid (1-methyl-cyclopropyl)-amide

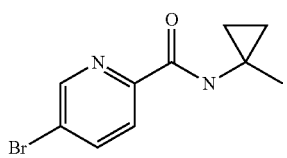

The title compound was obtained as a colorless oil, MS: m/e=255.0/257.0 (M+H⁺), using chemistry similar to that described in Example 1, step 1 from 5-bromo-pyridine-2-carboxylic acid and 1-methylcyclopropanamine hydrochloride.

Step 2: 5-Bromo-pyridine-2-carboxylic Acid methyl-(1-methyl-cyclopropyl)-amide

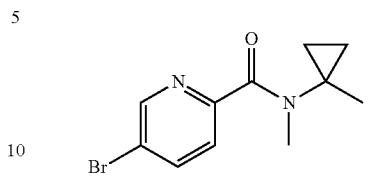

The title compound was obtained as a colorless oil, MS: m/e=269.1/271.1 (M+H⁺), using chemistry similar to that described in Example 2 from 5-bromo-pyridine-2-carboxylic acid (1-methyl-cyclopropyl)-amide (Example 31, step 1) and iodomethane.

Step 3: 5-(3-Fluoro-phenylethynyl)-pyridine-2-carboxylic Acid methyl-(1-methyl-cyclopropyl)-amide

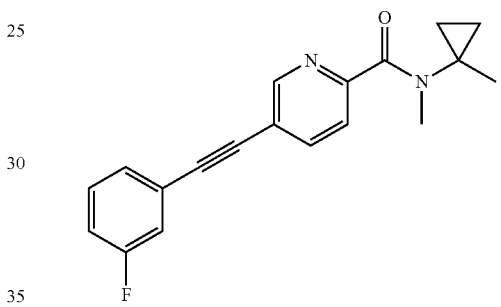

The title compound was obtained as a yellow oil, MS: m/e=309.0 (M−H⁺), using chemistry similar to that described in Example 1, step 2 from 5-bromo-pyridine-2-carboxylic acid methyl-(1-methyl-cyclopropyl)-amide (Example 31, step 2) and 1-ethynyl-3-fluoro-benzene.

Example 32

5-(4-Fluoro-phenylethynyl)-pyridine-2-carboxylic Acid methyl-(1-methyl-cyclopropyl)-amide

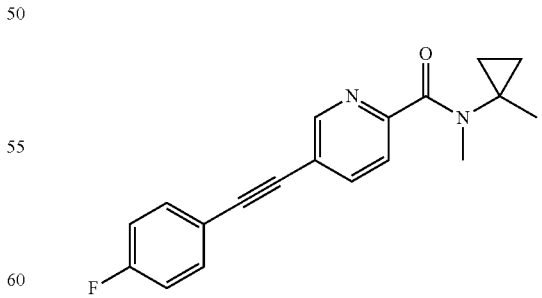

The title compound was obtained as a yellow oil, MS: m/e=309.4 (M−H⁺), using chemistry similar to that described in Example 1, step 2 from 5-bromo-pyridine-2-carboxylic acid methyl-(1-methyl-cyclopropyl)-amide (Example 31, step 2) and 1-ethynyl-4-fluoro-benzene.

Example 33

5-(3-Chloro-phenylethynyl)-pyridine-2-carboxylic Acid methyl-(1-trifluoromethyl-cyclopropyl)-amide

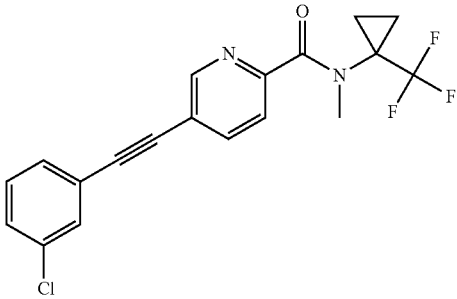 [SMILES: CN(C(=O)c1ccc(C#Cc2cccc(Cl)c2)cn1)C1(C(F)(F)F)CC1]

Step 1: 5-Bromo-pyridine-2-carboxylic Acid (1-trifluoromethyl-cyclopropyl)-amide

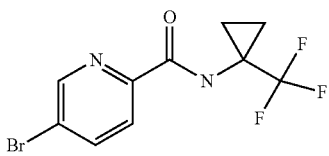

The title compound was obtained as a white solid, MS: m/e=308.9/311.0 (M+H⁺), using chemistry similar to that described in Example 1, step 1 from 5-bromo-pyridine-2-carboxylic acid and 1-(trifluoromethyl)cyclopropanamine.

Step 2: 5-Bromo-pyridine-2-carboxylic Acid methyl-(1-trifluoromethyl-cyclopropyl)-amide

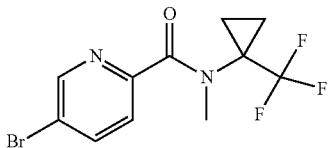 [SMILES: CN(C(=O)c1ccc(Br)cn1)C1(C(F)(F)F)CC1]

The title compound was obtained as a colorless oil, MS: m/e=323.0/325.1 (M+H⁺), using chemistry similar to that described in Example 2 from 5-bromo-pyridine-2-carboxylic acid (1-trifluoromethyl-cyclopropyl)-amide (Example 33, step 1) and iodomethane.

Step 3: 5-(3-Chloro-phenylethynyl)-pyridine-2-carboxylic Acid methyl-(1-trifluoromethyl-cyclopropyl)-amide

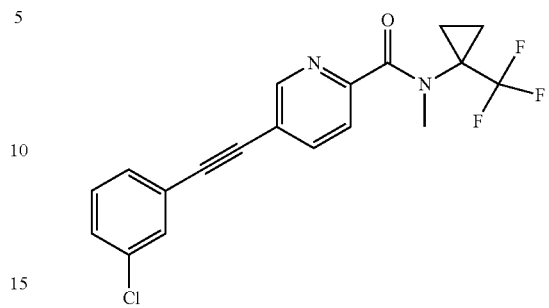

The title compound was obtained as a brown oil, MS: m/e=379.2/381.2 (M−H⁺), using chemistry similar to that described in Example 1, step 2 from 5-bromo-pyridine-2-carboxylic acid methyl-(1-trifluoromethyl-cyclopropyl)-amide (Example 33, step 2) and 1-ethynyl-3-chloro-benzene.

Example 34

5-m-Tolylethynyl-pyridine-2-carboxylic Acid methyl-(1-trifluoromethyl-cyclopropyl)-amide

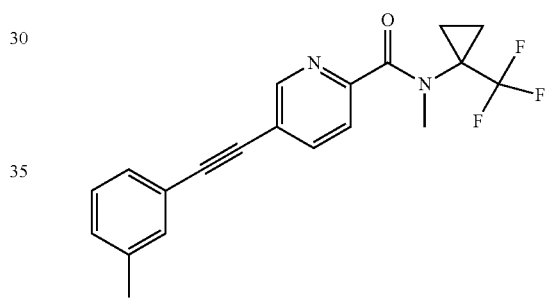

The title compound was obtained as a brown oil, MS: m/e=359.0 (M−H⁺), using chemistry similar to that described in Example 1, step 2 from 5-bromo-pyridine-2-carboxylic acid methyl-(1-trifluoromethyl-cyclopropyl)-amide (Example 33, step 2) and 1-ethynyl-3-methyl-benzene.

Example 35

(2,2-Dimethyl-morpholin-4-yl)-[5-(3-fluoro-phenylethynyl)-pyridin-2-yl]-methanone

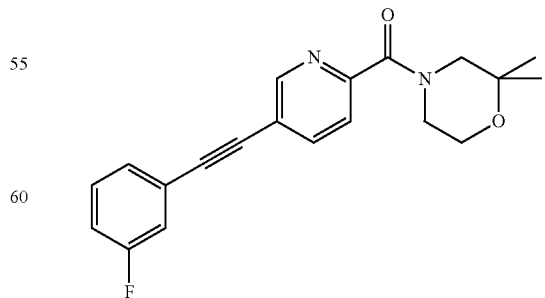

The title compound was obtained as a yellow solid, MS: m/e=339.3 (M+H⁺), using chemistry similar to that described in Example 1, step 1 from 5-(3-fluoro-phenylethynyl)-pyridine-2-carboxylic acid (Example 25, step 1) and 2,2-dimethylmorpholine.

Example 36

[5-(2,5-Difluoro-phenylethynyl)-pyridin-2-yl]-(2,2-dimethyl-morpholin-4-yl)-methanone

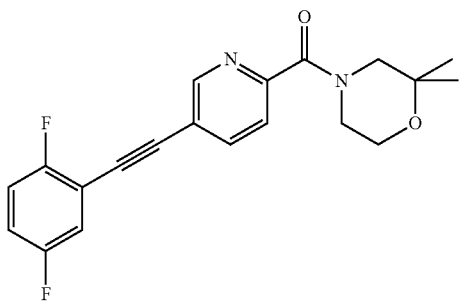 [SMILES: CC1(C)CN(C(=O)c2ccc(C#Cc3cc(F)ccc3F)cn2)CCO1]

Step 1: (5-Bromo-pyridin-2-yl)-(2,2-dimethyl-morpholin-4-yl)-methanone

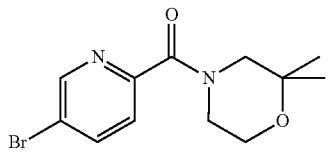 [SMILES: CC1(C)CN(C(=O)c2ccc(Br)cn2)CCO1]

The title compound was obtained as a colorless oil, MS: m/e=299.2/301.1 (M+H$^+$), using chemistry similar to that described in Example 1, step 1 from 5-bromo-pyridine-2-carboxylic acid and 2,2-dimethylmorpholine.

Step 2: (2,2-Dimethyl-morpholin-4-yl)-(5-trimethylsilanylethynyl-pyridin-2-yl)-methanone

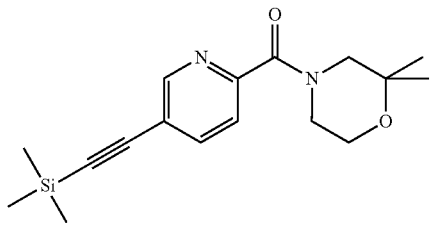

The title compound was obtained as a yellow oil, MS: m/e=317.1 (M−H$^+$), using chemistry similar to that described in Example 1, step 2 from (5-bromo-pyridin-2-yl)-(2,2-dimethyl-morpholin-4-yl)-methanone (Example 36, step 1) and ethynyltrimethylsilane.

Step 3: [5-(2,5-Difluoro-phenylethynyl)-pyridin-2-yl]-(2,2-dimethyl-morpholin-4-yl)-methanone

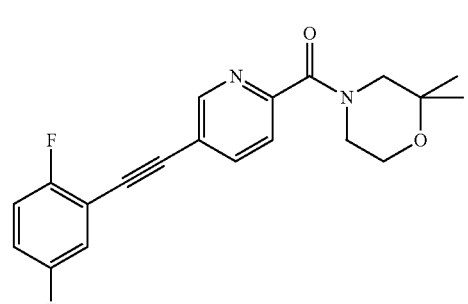

The title compound was obtained as a yellow oil, MS: m/e=357.1 (M+H$^+$), using chemistry similar to that described in Example 3, step 3 from (2,2-dimethyl-morpholin-4-yl)-(5-trimethylsilanylethynyl-pyridin-2-yl)-methanone (Example 36, step 2) and 1,4-difluoro-2-iodobenzene.

Example 37

[5-(3-Fluoro-phenylethynyl)-pyridin-2-yl]-(4-hydroxy-4-methyl-piperidin-1-yl)-methanone

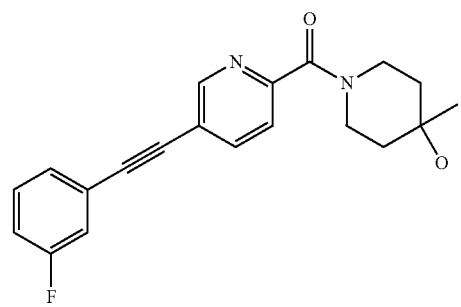 [SMILES: CC1(O)CCN(C(=O)c2ccc(C#Cc3cccc(F)c3)cn2)CC1]

Step 1: 1-(5-Bromo-pyridine-2-carbonyl)-piperidin-4-one

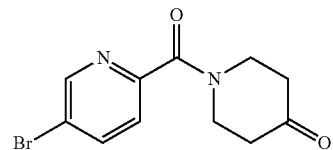 [SMILES: O=C1CCN(C(=O)c2ccc(Br)cn2)CC1]

The title compound was obtained as a white solid, MS: m/e=283.0/285.0 (M+H$^+$), using chemistry similar to that described in Example 1, step 1 from 5-bromo-pyridine-2-carboxylic acid and piperidin-4-one hydrochloride.

Step 2: (5-Bromo-pyridin-2-yl)-(4-hydroxy-4-methyl-piperidin-1-yl)-methanone

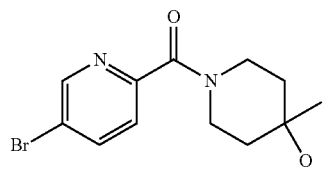 [SMILES: CC1(O)CCN(C(=O)c2ccc(Br)cn2)CC1]

1-(5-Bromo-pyridine-2-carbonyl)-piperidin-4-one (Example 37, step 1) (135 mg, 0.48 mmol) was dissolved in THF (3 ml) and the mixture was cooled to 0-5° C. 3M Methylmagnesium bromide (190 µl, 0.57 mmol, 1.2 equiv.) was added drop wise at 0-5° C. and the mixture was stirred for 2 hours at 0-5° C. The reaction mixture was extracted with saturated NH$_4$Cl solution and two times with ethyl acetate. The organic layers were extracted with water and brine, dried over sodium sulfate and evaporated to dryness. The crude product was purified by flash chromatography with a 20 g silica gel column and eluting with heptane:ethyl acetate 100:0→0:100. The desired (5-bromo-pyridin-2-yl)-(4-hydroxy-4-methyl-piperidin-1-yl)-methanone (35 mg, 25% yield) was obtained as a colorless oil, MS: m/e=299.2/301.1 (M+H$^+$).

Step 3: [5-(3-Fluoro-phenylethynyl)-pyridin-2-yl]-(4-hydroxy-4-methyl-piperidin-1-yl)-methanone

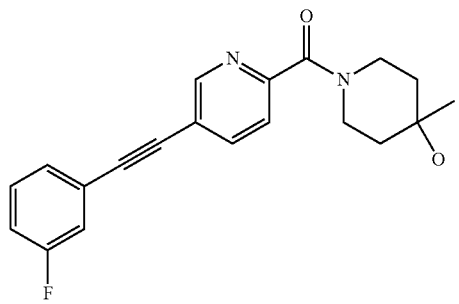 [SMILES: CC1(O)CCN(C(=O)c2ccc(C#Cc3cccc(F)c3)cn2)CC1]

The title compound was obtained as a brown oil, MS: m/e=339.3 (M−H$^+$), using chemistry similar to that described in Example 1, step 2 from (5-bromo-pyridin-2-yl)-(4-hydroxy-4-methyl-piperidin-1-yl)-methanone (Example 37, step 2) and 1-ethynyl-3-fluoro-benzene.

Example 38

(RS)-(4-Hydroxy-2,2-dimethyl-piperidin-1-yl)-(5-phenylethynyl-pyridin-2-yl)-methanone

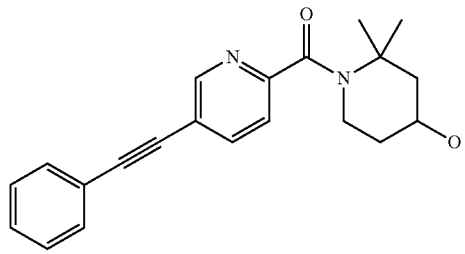 [SMILES: CC1(C)CC(O)CCN1C(=O)c1ccc(C#Cc2ccccc2)cn1]

Step 1: (RS)-(5-Bromo-pyridin-2-yl)-(4-hydroxy-2,2-dimethyl-piperidin-1-yl)-methanone

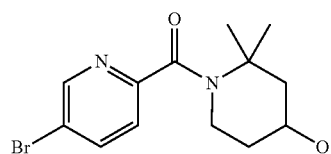 [SMILES: CC1(C)CC(O)CCN1C(=O)c1ccc(Br)cn1]

The title compound was obtained as a white solid, MS: m/e=314.4 (M+H$^+$), using chemistry similar to that described in Example 9, step 1 from 5-bromo-pyridine-2-carbonyl chloride and (RS)-2,2-dimethyl-piperidin-4-ol (CAS 937681-12-4).

Step 2: (RS)-(4-Hydroxy-2,2-dimethyl-piperidin-1-yl)-(5-phenylethynyl-pyridin-2-yl)-methanone

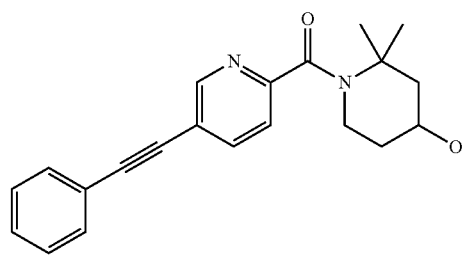 [SMILES: CC1(C)CC(O)CCN1C(=O)c1ccc(C#Cc2ccccc2)cn1]

The title compound was obtained as a white solid, MS: m/e=335.4 (M−H$^+$), using chemistry similar to that described in Example 1, step 2 from (RS)-(5-bromo-pyridin-2-yl)-(4-hydroxy-2,2-dimethyl-piperidin-1-yl)-methanone (Example 38, step 1) and phenylacetylene.

Example 39

(RS)-(4-Hydroxy-3,3-dimethyl-piperidin-1-yl)-(5-phenylethynyl-pyridin-2-yl)-methanone

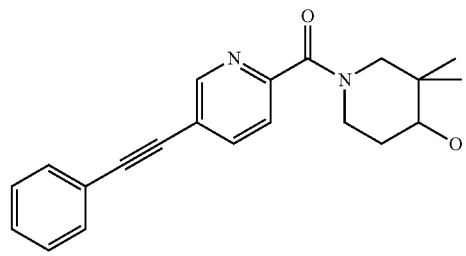

Step 1: (RS)-(5-Bromo-pyridin-2-yl)-(4-hydroxy-3,3-dimethyl-piperidin-1-yl)-methanone

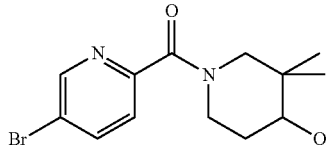 [SMILES: CC1(C)CN(C(=O)c2ccc(Br)cn2)CCC1O]

The title compound was obtained as a white solid, MS: m/e=314.2 (M+H$^+$), using chemistry similar to that described in Example 1, step 1 from 5-bromo-pyridine-2-carboxylic acid and (RS)-3,3-dimethyl-piperidin-4-ol (CAS 373603-88-4).

Step 2: (RS)-(4-Hydroxy-3,3-dimethyl-piperidin-1-yl)-(5-phenylethynyl-pyridin-2-yl)-methanone

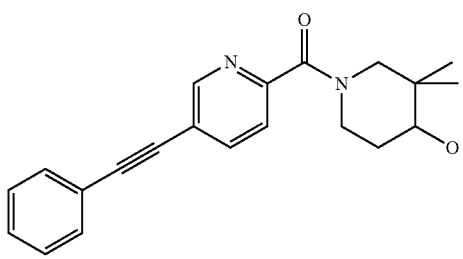 [SMILES: CC1(C)CN(C(=O)c2ccc(C#Cc3ccccc3)cn2)CCC1O]

The title compound was obtained as a colorless oil, MS: m/e=335.4 (M−H$^+$), using chemistry similar to that described in Example 1, step 2 from (RS)-(5-bromo-pyridin-2-yl)-(4-hydroxy-3,3-dimethyl-piperidin-1-yl)-methanone (Example 39, step 1) and phenylacetylene.

Example 40

(RS)-[5-(4-Fluoro-phenylethynyl)-pyridin-2-yl]-(4-hydroxy-3,3-dimethyl-piperidin-1-yl)-methanone

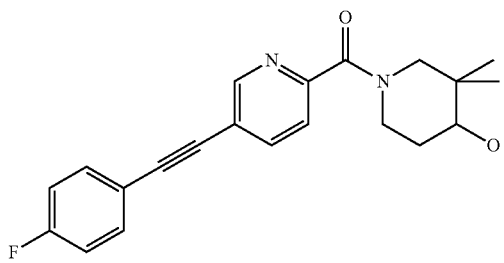

The title compound was obtained as a light yellow solid, MS: m/e=353.3 (M−H$^+$), using chemistry similar to that described in Example 1, step 2 from (RS)-(5-bromo-pyridin-2-yl)-(4-hydroxy-3,3-dimethyl-piperidin-1-yl)-methanone (Example 39, step 1) and 1-ethynyl-4-fluoro-benzene.

Example 41

(RS)-[5-(3-Fluoro-phenylethynyl)-pyridin-2-yl]-(4-hydroxy-3,3-dimethyl-piperidin-1-yl)-methanone

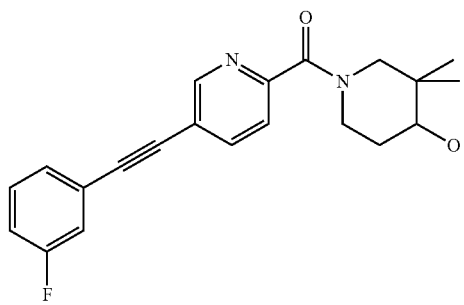 [SMILES: CC1(C)CN(C(=O)c2ccc(C#Cc3cccc(F)c3)cn2)CCC1O]

The title compound was obtained as a yellow oil, MS: m/e=353.3 (M−H$^+$), using chemistry similar to that described in Example 1, step 2 from (RS)-(5-bromo-pyridin-2-yl)-(4-hydroxy-3,3-dimethyl-piperidin-1-yl)-methanone (Example 39, step 1) and 1-ethynyl-3-fluoro-benzene.

Example 42

3-Fluoro-5-(3-fluoro-phenylethynyl)-pyridine-2-carboxylic Acid methyl-(1-methyl-cyclopropyl)-amide

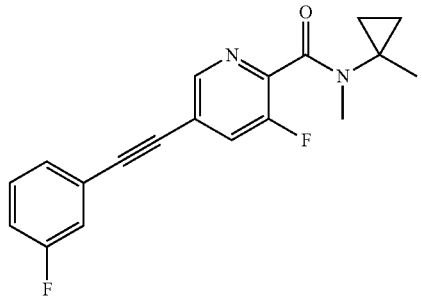 [SMILES: CN(C(=O)c1ncc(C#Cc2cccc(F)c2)cc1F)C1(C)CC1]

Step 1: 5-Bromo-3-fluoro-pyridine-2-carboxylic Acid (1-methyl-cyclopropyl)-amide

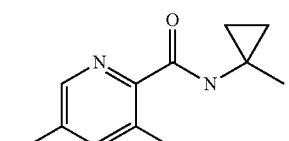

The title compound was obtained as a white solid, MS: m/e=273.1/275.1 (M+H$^+$), using chemistry similar to that described in Example 1, step 1 from 5-bromo-3-fluoro-pyridine-2-carboxylic acid and 1-methylcyclopropanamine hydrochloride.

Step 2: 5-Bromo-3-fluoro-pyridine-2-carboxylic Acid methyl-(1-methyl-cyclopropyl)-amide

The title compound was obtained as a white solid, MS: m/e=286.9/288.9 (M+H⁺), using chemistry similar to that described in Example 2 from 5-bromo-3-fluoro-pyridine-2-carboxylic acid (1-methyl-cyclopropyl)-amide (Example 42, step 1) and iodomethane.

Step 3: 3-Fluoro-5-(3-fluoro-phenylethynyl)-pyridine-2-carboxylic Acid methyl-(1-methyl-cyclopropyl)-amide

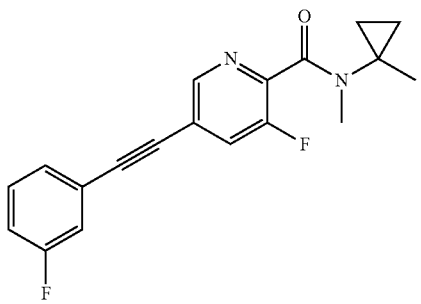 [SMILES: CN(C(=O)c1ncc(C#Cc2cccc(F)c2)cc1F)C1(C)CC1]

The title compound was obtained as a yellow oil, MS: m/e=327.3 (M−H⁺), using chemistry similar to that described in Example 1, step 2 from 5-bromo-3-fluoro-pyridine-2-carboxylic acid methyl-(1-methyl-cyclopropyl)-amide (Example 42, step 2) and 1-ethynyl-3-fluoro-benzene.

Example 43

3-Chloro-5-phenylethynyl-pyridine-2-carboxylic Acid tert-butyl-methyl-amide

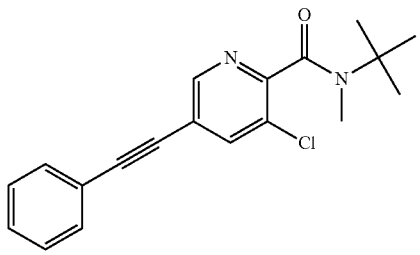 [SMILES: CN(C(=O)c1ncc(C#Cc2ccccc2)cc1Cl)C(C)(C)C]

Step 1: 5-Bromo-3-chloro-pyridine-2-carboxylic Acid tert-butyl-methyl-amide

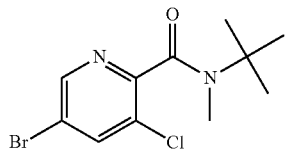 [SMILES: CN(C(=O)c1ncc(Br)cc1Cl)C(C)(C)C]

The title compound was obtained as a yellow oil, MS: m/e=304.9/307.0 (M+H⁺), using chemistry similar to that described in Example 1, step 1 from 5-bromo-3-chloro-pyridine-2-carboxylic acid and tert-butyl-methyl-amine.

Step 2: 3-Chloro-5-phenylethynyl-pyridine-2-carboxylic Acid tert-butyl-methyl-amide

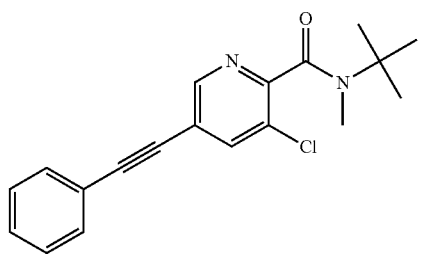 [SMILES: CN(C(=O)c1ncc(C#Cc2ccccc2)cc1Cl)C(C)(C)C]

The title compound was obtained as an orange solid, MS: m/e=327.1/329.0 (M−H⁺), using chemistry similar to that described in Example 1, step 2 from 5-bromo-3-chloro-pyridine-2-carboxylic acid tert-butyl-methyl-amide (Example 43, step 1) and phenylacetylene.

Example 44

5-(3-Fluoro-phenylethynyl)-pyrimidine-2-carboxylic Acid methyl-(1-trifluoromethyl-cyclopropyl)-amide

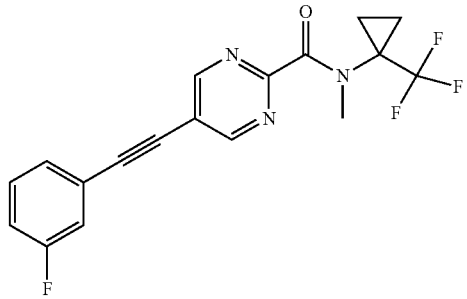 [SMILES: CN(C(=O)c1ncc(C#Cc2cccc(F)c2)cn1)C1(C(F)(F)F)CC1]

Step 1: 5-Bromo-pyrimidine-2-carboxylic Acid (1-trifluoromethyl-cyclopropyl)-amide

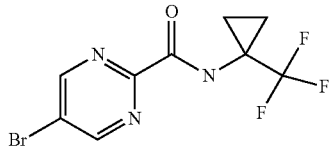 [SMILES: O=C(NC1(C(F)(F)F)CC1)c1ncc(Br)cn1]

The title compound was obtained as a yellow solid, MS: m/e=310.0/312.0 (M+H$^+$), using chemistry similar to that described in Example 1, step 1 from 5-bromo-pyrimidine-2-carboxylic acid and 1-(trifluoromethyl)cyclopropanamine Step 2: 5-Bromo-pyrimidine-2-carboxylic Acid methyl-(1-trifluoromethyl-cyclopropyl)-amide

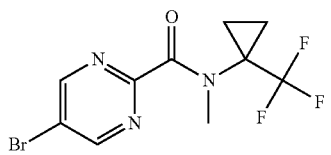 [SMILES: CN(C(=O)c1ncc(Br)cn1)C1(C(F)(F)F)CC1]

The title compound was obtained as a white solid, MS: m/e=324.0/326.1 (M+H$^+$), using chemistry similar to that described in Example 2 from 5-bromo-pyrimidine-2-carboxylic acid (1-trifluoromethyl-cyclopropyl)-amide (Example 44, step 1) and iodomethane.

Step 3: 5-(3-Fluoro-phenylethynyl)-pyrimidine-2-carboxylic Acid methyl-(1-trifluoromethyl-cyclopropyl)-amide

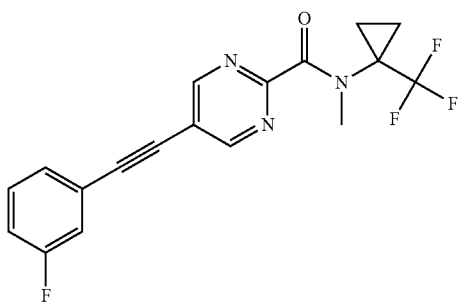 [SMILES: CN(C(=O)c1ncc(C#Cc2cccc(F)c2)cn1)C1(C(F)(F)F)CC1]

The title compound was obtained as a brown solid, MS: m/e=364.1 (M−H$^+$), using chemistry similar to that described in Example 1, step 2 from 5-bromo-pyrimidine-2-carboxylic acid methyl-(1-trifluoromethyl-cyclopropyl)-amide (Example 44, step 2) and 1-ethynyl-3-fluoro-benzene.

Example 45

(3,3-Difluoro-azetidin-1-yl)-(5-phenylethynyl-pyrimidin-2-yl)-methanone

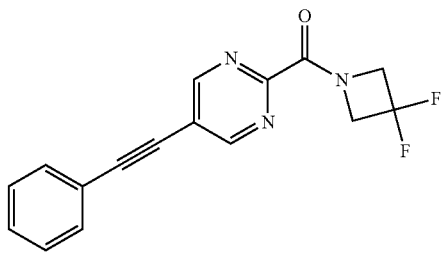 [SMILES: O=C(c1ncc(C#Cc2ccccc2)cn1)N1CC(F)(F)C1]

Step 1: 5-Phenylethynyl-pyrimidine-2-carboxylic Acid

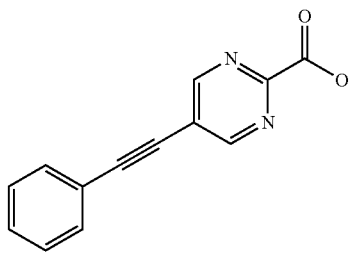 [SMILES: O=C(O)c1ncc(C#Cc2ccccc2)cn1]

The title compound was obtained as a white solid, MS: m/e=222.8 (M−H$^+$), using chemistry similar to that described in Example 25, step 1 from 5-bromo-pyrimidine-2-carboxylic acid.

Step 2: (3,3-Difluoro-azetidin-1-yl)-(5-phenylethynyl-pyrimidin-2-yl)-methanone

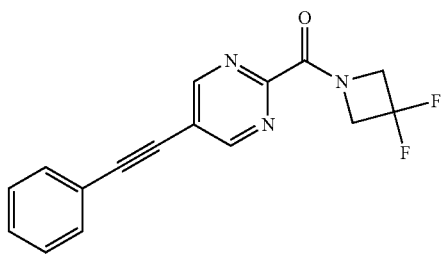 [SMILES: O=C(c1ncc(C#Cc2ccccc2)cn1)N1CC(F)(F)C1]

The title compound was obtained as a brown solid, MS: m/e=300.2 (M+H$^+$), using chemistry similar to that described in Example 1, step 1 from 5-phenylethynyl-pyrimidine-2-carboxylic acid (Example 45, step 1) and 3,3-difluoro-azetidine hydrochloride.

Example 46

(3,3-Dimethyl-piperidin-1-yl)-(5-phenylethynyl-pyrimidin-2-yl)-methanone

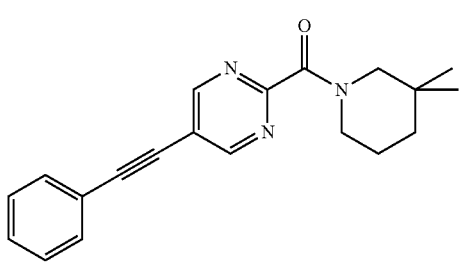 [SMILES: CC1(C)CCCN(C(=O)c2ncc(C#Cc3ccccc3)cn2)C1]

The title compound was obtained as an orange oil, MS: m/e=320.4 (M+H+), using chemistry similar to that described in Example 1, step 1 from 5-phenylethynyl-pyrimidine-2-carboxylic acid (Example 45, step 1) and 3,3-dimethylpiperidine.

Example 47

(RS)-(4-Hydroxy-2,2-dimethyl-piperidin-1-yl)-(5-phenylethynyl-pyrimidin-2-yl)-methanone

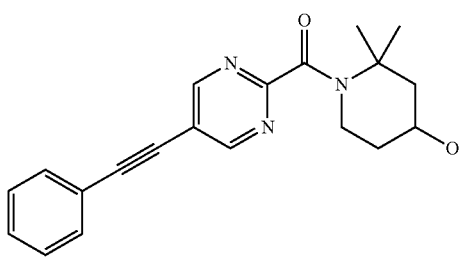 [SMILES: CC1(C)CC(O)CCN1C(=O)c1ncc(C#Cc2ccccc2)cn1]

Step 1: (RS)-(5-Bromo-pyrimidin-2-yl)-(4-hydroxy-2,2-dimethyl-piperidin-1-yl)-methanone

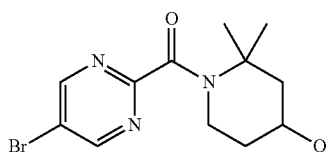 [SMILES: CC1(C)CC(O)CCN1C(=O)c1ncc(Br)cn1]

The title compound was obtained as a white solid, MS: m/e=315.2 (M+H+), using chemistry similar to that described in Example 9, step 1 from 5-bromo-pyrimidine-2-carboxylic acid and (RS)-2,2-dimethyl-piperidin-4-ol (CAS 937681-12-4).

Step 2: (RS)-(4-Hydroxy-2,2-dimethyl-piperidin-1-yl)-(5-phenylethynyl-pyrimidin-2-yl)-methanone

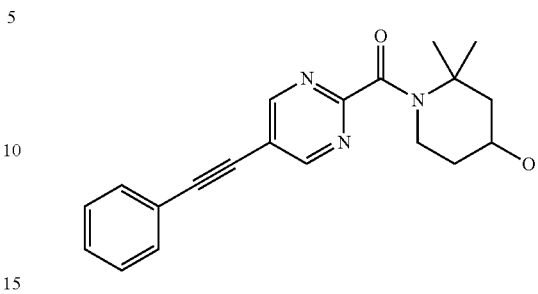

The title compound was obtained as a white solid, MS: m/e=336.2 (M−H+), using chemistry similar to that described in Example 1, step 2 from (RS)-(5-bromo-pyrimidin-2-yl)-(4-hydroxy-2,2-dimethyl-piperidin-1-yl)-methanone (Example 47, step 1) and phenylacetylene.

Example 48

(RS)-(4-Hydroxy-3,3-dimethyl-piperidin-1-yl)-(5-phenylethynyl-pyrimidin-2-yl)-methanone

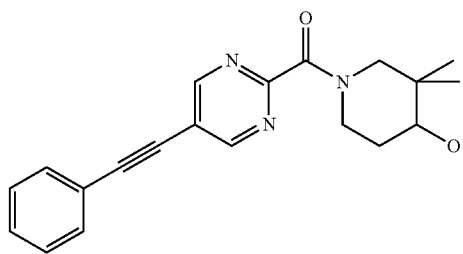

Step 1: (RS)-(5-Bromo-pyrimidin-2-yl)-(4-hydroxy-3,3-dimethyl-piperidin-1-yl)-methanone

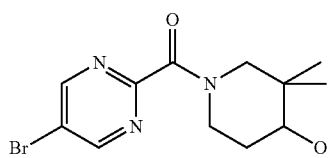 [SMILES: CC1(C)CN(C(=O)c2ncc(Br)cn2)CCC1O]

The title compound was obtained as a white solid, MS: m/e=315.4 (M+H+), using chemistry similar to that described in Example 1, step 1 from 5-bromo-pyrimidine-2-carboxylic acid and (RS)-3,3-dimethyl-piperidin-4-ol (CAS 373603-88-4).

Step 2: (RS)-(4-Hydroxy-3,3-dimethyl-piperidin-1-yl)-(5-phenylethynyl-pyrimidin-2-yl)-methanone

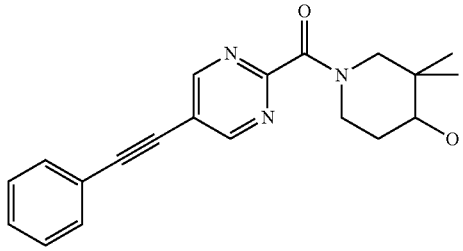

The title compound was obtained as a brown solid, MS: m/e=336.2 (M−H⁺), using chemistry similar to that described in Example 1, step 2 from (RS)-(5-bromo-pyrimidin-2-yl)-(4-hydroxy-3,3-dimethyl-piperidin-1-yl)-methanone (Example 48, step 1) and phenylacetylene.

Example 49

(RS)-[5-(3-Fluoro-phenylethynyl)-pyrimidin-2-yl]-(4-hydroxy-3,3-dimethyl-piperidin-1-yl)-methanone

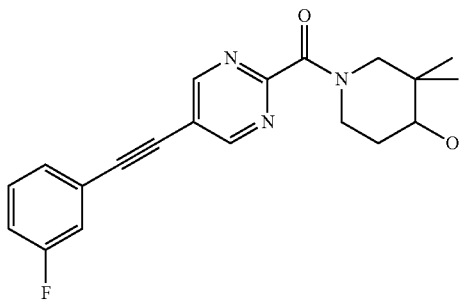 [SMILES: CC1(C)CN(C(=O)c2ncc(C#Cc3cccc(F)c3)cn2)CCC1O]

The title compound was obtained as a light yellow solid, MS: m/e=354.3 (M−H⁺), using chemistry similar to that described in Example 1, step 2 from (RS)-(5-bromo-pyrimidin-2-yl)-(4-hydroxy-3,3-dimethyl-piperidin-1-yl)-methanone (Example 48, step 1) and 1-ethynyl-3-fluoro-benzene.

Example 50

3-Fluoro-5-phenylethynyl-pyridine-2-carboxylic Acid methyl-(3-methyl-oxetan-3-yl)-amide

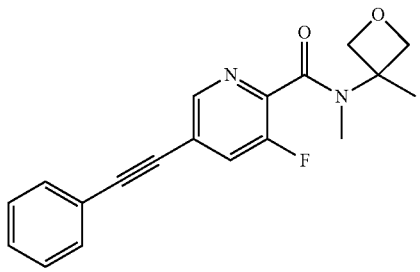 [SMILES: CN(C(=O)c1ncc(C#Cc2ccccc2)cc1F)C1(C)COC1]

Step 1: 3-Fluoro-5-phenylethynyl-pyridine-2-carboxylic Acid

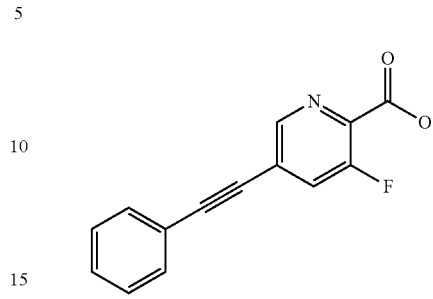

The title compound was obtained as a yellow solid, MS: m/e=239.8 (M−H⁺), using chemistry similar to that described in Example 25, step 1 from 5-bromo-3-fluoro-pyridine-2-carboxylic acid.

Step 2: 3-Fluoro-5-phenylethynyl-pyridine-2-carboxylic Acid (3-methyl-oxetan-3-yl)-amide

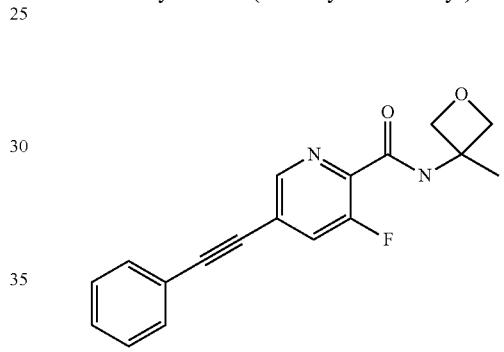

The title compound was obtained as a light yellow solid, MS: m/e=311.2 (M+H⁺), using chemistry similar to that described in Example 1, step 1 from 3-fluoro-5-phenylethynyl-pyridine-2-carboxylic acid (Example 50, step 1) and 3-methyloxetan-3-amine.

Step 3: 3-Fluoro-5-phenylethynyl-pyridine-2-carboxylic Acid methyl-(3-methyl-oxetan-3-yl)-amide

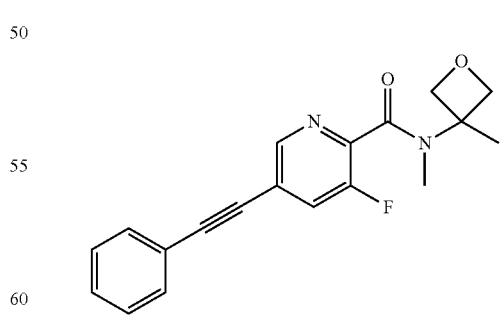

The title compound was obtained as a light yellow semi-solid, MS: m/e=325.4 (M+H⁺), using chemistry similar to that described in Example 2 from 3-fluoro-5-phenylethynyl-pyridine-2-carboxylic acid (3-methyl-oxetan-3-yl)-amide (Example 50, step 2) and iodomethane.

Example 51

(RS)-3-Fluoro-5-phenylethynyl-pyridine-2-carboxylic Acid methyl-(2,2,2-trifluoro-1-methyl-ethyl)-amide

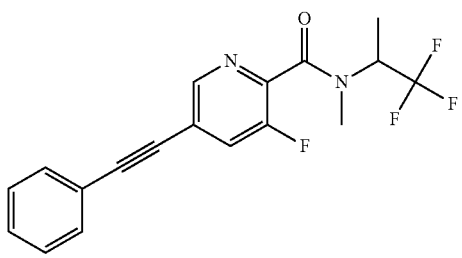 [SMILES: CC(N(C)C(=O)c1ncc(C#Cc2ccccc2)cc1F)C(F)(F)F]

Step 1: (RS)-3-Fluoro-5-phenylethynyl-pyridine-2-carboxylic Acid (2,2,2-trifluoro-1-methyl-ethyl)-amide

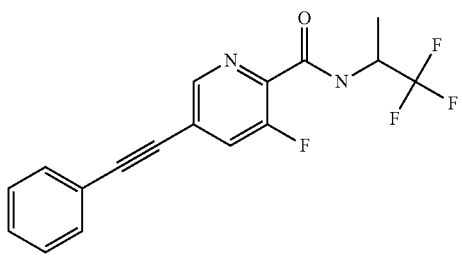 [SMILES: CC(NC(=O)c1ncc(C#Cc2ccccc2)cc1F)C(F)(F)F]

The title compound was obtained as a light yellow solid, MS: m/e=337.1 (M+H$^+$), using chemistry similar to that described in Example 1, step 1 from 3-fluoro-5-phenylethynyl-pyridine-2-carboxylic acid (Example 50, step 1) and (RS)-1,1,1-trifluoropropan-2-amine hydrochloride.

Step 2: (RS)-3-Fluoro-5-phenylethynyl-pyridine-2-carboxylic Acid methyl-(2,2,2-trifluoro-1-methyl-ethyl)-amide

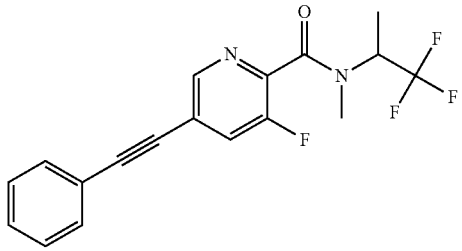 [SMILES: CC(N(C)C(=O)c1ncc(C#Cc2ccccc2)cc1F)C(F)(F)F]

The title compound was obtained as a light yellow oil, MS: m/e=351.3 (M+H$^+$), using chemistry similar to that described in Example 2 from (RS)-3-fluoro-5-phenylethynyl-pyridine-2-carboxylic acid (2,2,2-trifluoro-1-methyl-ethyl)-amide (Example 51, step 1) and iodomethane.

Example 52

3-Cyano-5-phenylethynyl-pyridine-2-carboxylic Acid tert-butyl-methyl-amide

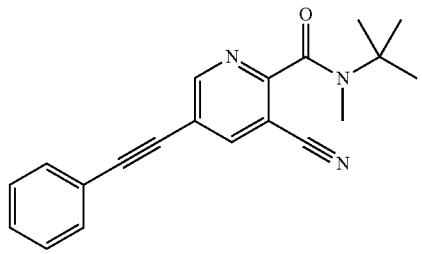 [SMILES: CN(C(=O)c1ncc(C#Cc2ccccc2)cc1C#N)C(C)(C)C]

Step 1: 3-Bromo-furo[3,4-b]pyridine-5,7-dione

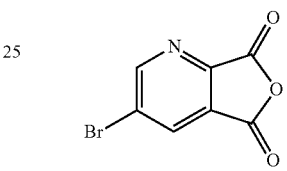

A suspension of 5-bromo-pyridine-2,3-dicarboxylic acid (700 mg, 2.85 mmol) in acetic anhydride (0.88 ml, 9.39 mmol, 3.3 equiv.) was heated at 80° C. for 10 min and then refluxed for 1 h. Acetic anhydride was evaporated off in vacuo. The resulting solid was triturated with hexane to afford 3-bromo-furo[3,4-b]pyridine-5,7-dione (510 mg, 79%) as off white solid.

Step 2: 5-Bromo-pyridine-2,3-dicarboxylic Acid 2-isopropyl Ester

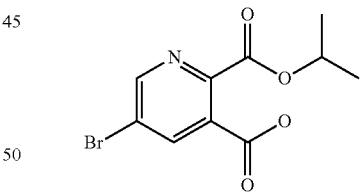

To a solution of 3-bromo-furo[3,4-b]pyridine-5,7-dione (200 mg, 0.877 mmol) in THF (3 ml) at −10° C. was added Mg(ClO$_4$)$_2$ (235 mg, 1.053 mmol, 1.2 equiv.) and the reaction mixture was stirred for 5 min at that temperature. Then isopropanol (6 ml) was added and the reaction mixture was stirred at 25° C. for 16 hours. The volatilities were removed in vacuo and the resultant residue was dissolved in EtOAc (30 ml). The organic layer was washed with water (15 ml) and brine (15 ml), dried over anhydrous Na$_2$SO$_4$, filtered and evaporated off in vacuo. The crude material thus obtained was purified by column chromatography over normal silica gel (30-50% EtOAc/hexane) to afford 5-bromo-pyridine-2,3-dicarboxylic acid 2-isopropyl ester (210 mg, 83.1%) as light brown solid, MS: m/e=286.0 (M−H$^+$).

Step 3: 5-Bromo-3-cyano-pyridine-2-carboxylic Acid Isopropyl Ester

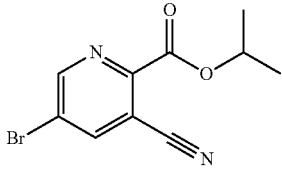

To a solution of 5-bromo-pyridine-2,3-dicarboxylic acid 2-isopropyl ester (630 mg, 2.187 mmol) in pyridine (8 ml) at 0° C. was added methane sulfonyl chloride (0.34 ml, 4.37 mmol, 2 equiv.) and the reaction mixture was stirred for 1 hour at 25° C. Then NH₃ gas was purged in to reaction mixture at 0° C. and stirred at 25° C. for 30 minutes. The excess NH₃ was evaporated off in vacuo. The reaction mixture was cooled to 0° C., a fresh lot of methane sulfonyl chloride (1.35 ml, 17.49 mmol, 8 equiv.) was added drop wise to the mixture and stirring was continued at 25° C. for another 16 hours. The reaction mixture was quenched with saturated aqueous NaHCO₃ solution (20 ml) and extracted with EtOAc (2×40 ml). The combined organic layer was dried over anhydrous Na₂SO₄ and evaporated under reduced pressure to dryness. The resulting crude material was purified by column chromatography over normal silica gel (10% EtOAc in hexane) to give 5-bromo-3-cyano-pyridine-2-carboxylic acid isopropyl ester (320 mg, 54%) as yellow oil.

Step 4: 5-Bromo-3-cyano-pyridine-2-carboxylic Acid

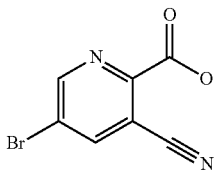 [SMILES: N#Cc1cc(Br)cnc1C(=O)O]

To a solution of 5-bromo-3-cyano-pyridine-2-carboxylic acid isopropyl ester (70 mg, 0.26 mmol) in a mixture of THF (3 ml) and water (3 ml) was added lithium hydroxide monohydrate (32.75 mg, 0.78 mmol, 3 equiv.). The reaction mixture was stirred for 2 hours at 25° C. The mixture was acidified with 2N aqueous HCl solution (pH 5) and extracted with EtOAc (2×15 ml). The combined organic layer was dried over anhydrous Na₂SO₄ and evaporated under reduced pressure to dryness to give 5-bromo-3-cyano-pyridine-2-carboxylic acid (45 mg, 76%) as a yellow solid which was used in next step without further purification.

Step 5: 5-Bromo-3-cyano-pyridine-2-carboxylic Acid tert-butyl-methyl-amide

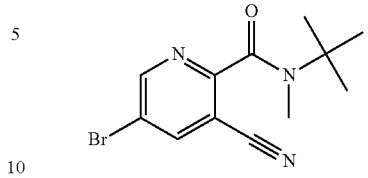

To a solution of 5-bromo-3-cyano-pyridine-2-carboxylic acid (100 mg, 0.44 mmol) in dichloromethane (5 ml) at 0° C. were added DIPEA (0.226 ml, 1.32 mmol, 3 equiv.), methyl tert-butyl amine (0.079 ml, 0.661 mmol, 1.5 equiv.) and HBTU (250 mg, 0.661 mmol, 1.5 equiv.). The reaction mixture was stirred at 25° C. for 14 hours. The solvent was removed in vacuum and the resulting crude material was purified by column chromatography over normal silica gel (10-20% EtOAc in hexane) to afford 5-bromo-3-cyano-pyridine-2-carboxylic acid tert-butyl-methyl-amide (85 mg, 65%) as colorless oil.

Step 6: 3-Cyano-5-phenylethynyl-pyridine-2-carboxylic Acid tert-butyl-methyl-amide

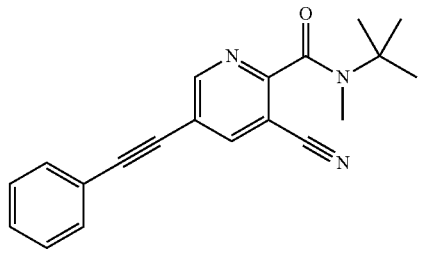 [SMILES: CN(C(=O)c1ncc(C#Cc2ccccc2)cc1C#N)C(C)(C)C]

The title compound was obtained as a light brown solid, MS: m/e=318.0 (M–H⁺), using chemistry similar to that described in Example 1, step 2 from 5-bromo-3-cyano-pyridine-2-carboxylic acid tert-butyl-methyl-amide (Example 52, step 2) and phenylacetylene.

Example 53

5-(5-Chloro-pyridin-3-ylethynyl)-pyridine-2-carboxylic Acid methyl-(1-trifluoromethyl-cyclopropyl)-amide

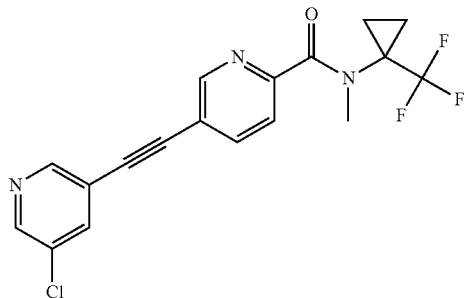 [SMILES: CN(C(=O)c1ccc(C#Cc2cncc(Cl)c2)cn1)C1(C(F)(F)F)CC1]

The title compound was obtained as a light yellow solid, MS: m/e=380.3/382.3 (M–H⁺), using chemistry similar to that described in Example 1, step 2 from 5-bromo-pyridine- 2-carboxylic acid methyl-(1-trifluoromethyl-cyclopropyl)-amide (Example 33, step 2) and 3-chloro-5-ethynyl-pyridine.

Example 54

5-(2-Chloro-pyridin-4-ylethynyl)-pyridine-2-carboxylic Acid (2,2,2-trifluoro-1,1-dimethyl-ethyl)-amide

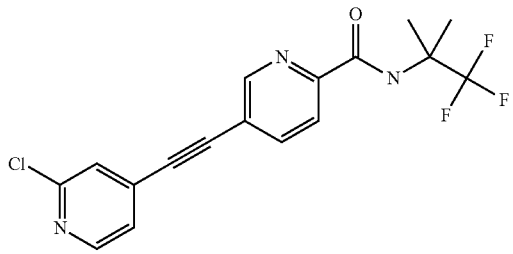 [SMILES: CC(C)(NC(=O)c1ccc(C#Cc2ccnc(Cl)c2)cn1)C(F)(F)F]

Step 1: 5-Bromo-pyridine-2-carboxylic Acid (2,2,2-trifluoro-1,1-dimethyl-ethyl)-amide

The title compound was obtained as a colorless oil, MS: m/e=311.2/313.2 (M+H⁺), using chemistry similar to that described in Example 1, step 1 from 5-bromo-pyridine-2-carboxylic acid and 1,1,1-trifluoro-2-methylpropan-2-amine.

Step 2: 5-(2-Chloro-pyridin-4-ylethynyl)-pyridine-2-carboxylic Acid (2,2,2-trifluoro-1,1-dimethyl-ethyl)-amide

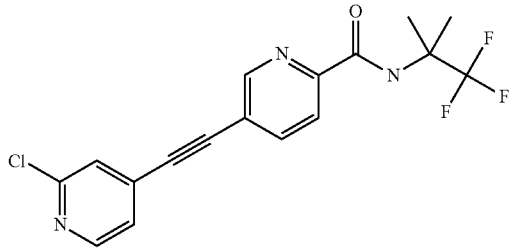 [SMILES: CC(C)(NC(=O)c1ccc(C#Cc2ccnc(Cl)c2)cn1)C(F)(F)F]

The title compound was obtained as a yellow oil, MS: m/e=368.4/370.4 (M−H⁺), using chemistry similar to that described in Example 3, step 3 from 5-bromo-pyridine-2-carboxylic acid (2,2,2-trifluoro-1,1-dimethyl-ethyl)-amide (Example 54, step 1) and 2-chloro-4-trimethylsilanylethynyl-pyridine.

Example 55

5-(5-Chloro-pyridin-3-ylethynyl)-pyridine-2-carboxylic Acid methyl-(2,2,2-trifluoro-1,1-dimethyl-ethyl)-amide

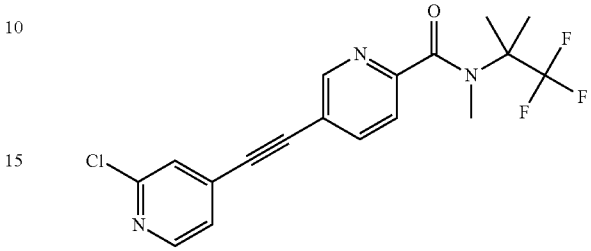

Step 1: 5-(5-Chloro-pyridin-3-ylethynyl)-pyridine-2-carboxylic Acid (2,2,2-trifluoro-1,1-dimethyl-ethyl)-amide

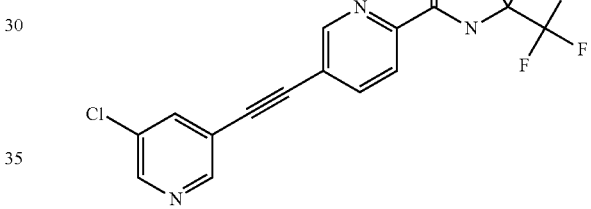

The title compound was obtained as a white solid, MS: m/e=368.3/370.4 (M−H⁺), using chemistry similar to that described in Example 1, step 2 from 5-bromo-pyridine-2-carboxylic acid (2,2,2-trifluoro-1,1-dimethyl-ethyl)-amide (Example 54, step 1) and 3-chloro-5-ethynyl-pyridine.

Step 2: 5-(5-Chloro-pyridin-3-ylethynyl)-pyridine-2-carboxylic Acid methyl-(2,2,2-trifluoro-1,1-dimethyl-ethyl)-amide

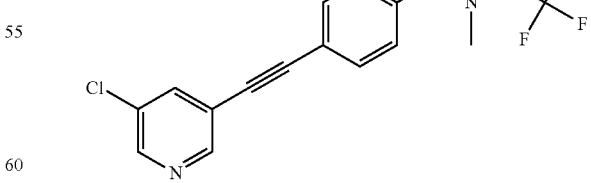

The title compound was obtained as a white solid, MS: m/e=382.3/384.3 (M+H⁺), using chemistry similar to that described in Example 2 from 5-(5-chloro-pyridin-3-ylethynyl)-pyridine-2-carboxylic acid (2,2,2-trifluoro-1,1-dimethyl-ethyl)-amide (Example 55, step 1) and iodomethane.

Example 56

5-(3-Chloro-phenylethynyl)-pyridine-2-carboxylic Acid methyl-(2,2,2-trifluoro-1,1-dimethyl-ethyl)-amide

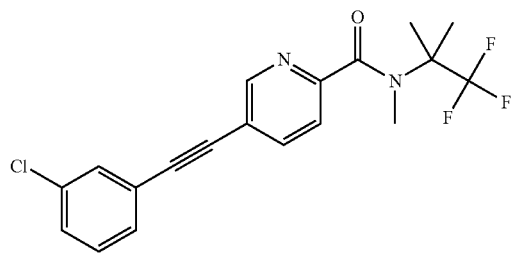 [SMILES: CN(C(=O)c1ccc(C#Cc2cccc(Cl)c2)cn1)C(C)(C)C(F)(F)F]

Step 1: 5-(3-Chloro-phenylethynyl)-pyridine-2-carboxylic Acid (2,2,2-trifluoro-1,1-dimethyl-ethyl)-amide

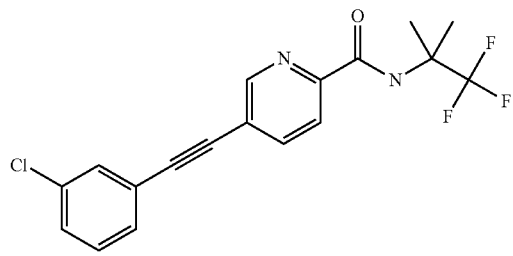

The title compound was obtained as a light yellow solid, MS: m/e=367.3/369.3 (M−H⁺), using chemistry similar to that described in Example 1, step 2 from 5-bromo-pyridine-2-carboxylic acid (2,2,2-trifluoro-1,1-dimethyl-ethyl)-amide (Example 54, step 1) and 3-chlorophenylacetylene.

Step 2: 5-(3-Chloro-phenylethynyl)-pyridine-2-carboxylic Acid methyl-(2,2,2-trifluoro-1,1-dimethyl-ethyl)-amide

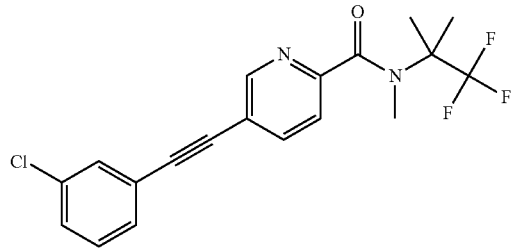 [SMILES: CN(C(=O)c1ccc(C#Cc2cccc(Cl)c2)cn1)C(C)(C)C(F)(F)F]

The title compound was obtained as a light yellow oil, MS: m/e=381.4/383.3 (M+H⁺), using chemistry similar to that described in Example 2 from 5-(3-chloro-phenylethynyl)-pyridine-2-carboxylic acid (2,2,2-trifluoro-1,1-dimethyl-ethyl)-amide (Example 56, step 1) and iodomethane.

Example 57

(RS)-5-(2-Chloro-pyridin-4-ylethynyl)-pyridine-2-carboxylic Acid (2,2,2-trifluoro-1-methyl-ethyl)-amide

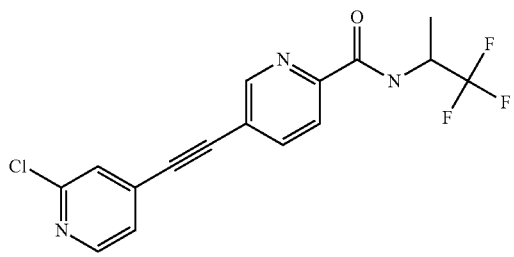

Step 1: (RS)-5-Bromo-pyridine-2-carboxylic Acid (2,2,2-trifluoro-1-methyl-ethyl)-amide

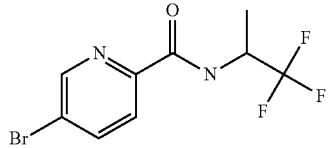 [SMILES: CC(NC(=O)c1ccc(Br)cn1)C(F)(F)F]

The title compound was obtained as a colorless oil, MS: m/e=297.2/299.2 (M+H⁺), using chemistry similar to that described in Example 1, step 1 from 5-bromo-pyridine-2-carboxylic acid and (RS)-1,1,1-trifluoropropan-2-amine.

Step 2: (RS)-5-(2-Chloro-pyridin-4-ylethynyl)-pyridine-2-carboxylic Acid (2,2,2-trifluoro-1-methyl-ethyl)-amide

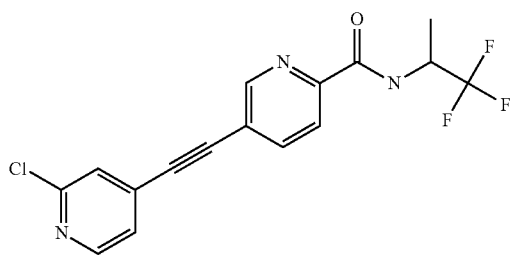

The title compound was obtained as a light yellow solid, MS: m/e=354.3/356.3 (M−H⁺), using chemistry similar to that described in Example 3, step 3 from (RS)-5-bromo-pyridine-2-carboxylic acid (2,2,2-trifluoro-1-methyl-ethyl)-amide (Example 57, step 1) and 2-chloro-4-trimethylsilanyl-ethynyl-pyridine.

Example 58

5-(2-Chloro-pyridin-4-ylethynyl)-pyrimidine-2-carboxylic Acid (2,2,2-trifluoro-1,1-dimethyl-ethyl)-amide

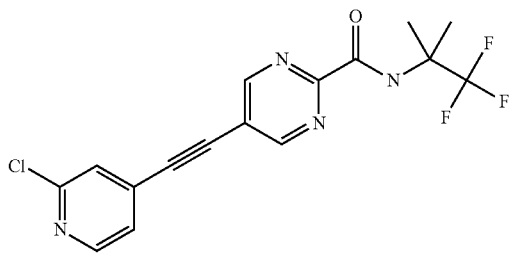 [SMILES: CC(C)(NC(=O)c1ncc(C#Cc2ccnc(Cl)c2)cn1)C(F)(F)F]

Step 1: 5-Bromo-pyrimidine-2-carboxylic Acid (2,2,2-trifluoro-1,1-dimethyl-ethyl)-amide

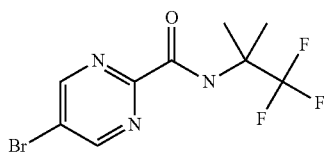 [SMILES: CC(C)(NC(=O)c1ncc(Br)cn1)C(F)(F)F]

The title compound was obtained as a light yellow solid, MS: m/e=312.2/314.2 (M+H⁺), using chemistry similar to that described in Example 1, step 1 from 5-bromo-pyrimidine-2-carboxylic acid and 1,1,1-trifluoro-2-methylpropan-2-amine.

Step 2: 5-(2-Chloro-pyrimidin-4-ylethynyl)-pyridine-2-carboxylic Acid (2,2,2-trifluoro-1,1-dimethyl-ethyl)-amide

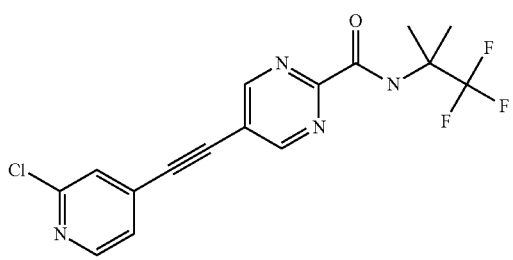 [SMILES: CC(C)(NC(=O)c1ncc(C#Cc2ccnc(Cl)c2)cn1)C(F)(F)F]

The title compound was obtained as a brown solid, MS: m/e=369.3/371.2 (M−H⁺), using chemistry similar to that described in Example 3, step 3 from 5-bromo-pyrimidine-2-carboxylic acid (2,2,2-trifluoro-1,1-dimethyl-ethyl)-amide (Example 58, step 1) and 2-chloro-4-trimethylsilanylethynyl-pyridine.

Example 59

(R) or (S)-5-(2-Chloro-pyridin-4-ylethynyl)-pyridine-2-carboxylic Acid (2,2,2-trifluoro-1-methyl-ethyl)-amide

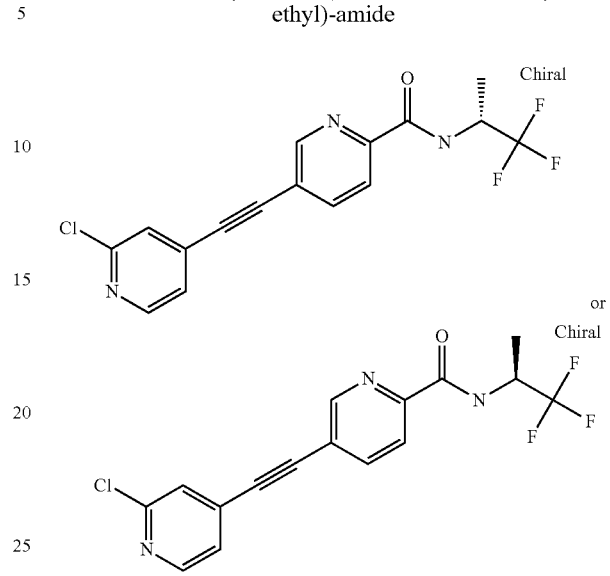

The title compound, a white solid, MS: m/e=354.3/356.3 (M+H⁺), was prepared by separation of (RS)-5-(2-chloro-pyridin-4-ylethynyl)-pyridine-2-carboxylic acid (2,2,2-trifluoro-1-methyl-ethyl)-amide (Example 57) using a chiral column (Reprosil chiral NR with heptane:isopropanol 80:20 as solvent).

Example 60

(S) or (R)-5-(2-Chloro-pyridin-4-ylethynyl)-pyridine-2-carboxylic Acid (2,2,2-trifluoro-1-methyl-ethyl)-amide

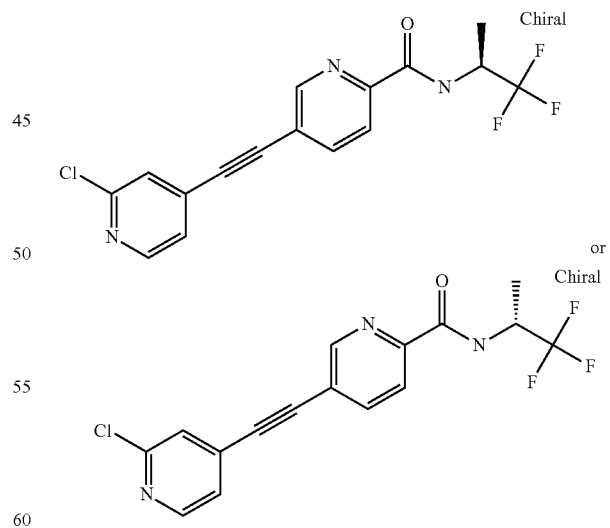

The title compound, a white solid, MS: m/e=354.3/356.3 (M+H⁺), was prepared by separation of (RS)-5-(2-chloro-pyridin-4-ylethynyl)-pyridine-2-carboxylic acid (2,2,2-trifluoro-1-methyl-ethyl)-amide (Example 57) using a chiral column (Reprosil chiral NR with heptane:isopropanol 80:20 as solvent).

Example 61

(RS)-5-(3-Chloro-phenylethynyl)-pyridine-2-carboxylic Acid (2,2,2-trifluoro-1-methyl-ethyl)-amide

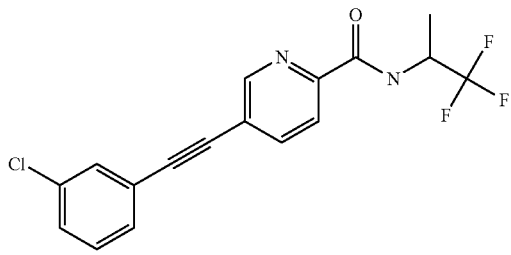

The title compound was obtained as a light yellow solid, MS: m/e=353.3/355.3 (M–H⁺), using chemistry similar to that described in Example 1, step 2 from (RS)-5-bromo-pyridine-2-carboxylic acid (2,2,2-trifluoro-1-methyl-ethyl)-amide (Example 57, step 1) and 3-chlorophenylacetylene.

Example 62

(RS)-5-(3-Chloro-phenylethynyl)-pyridine-2-carboxylic acid methyl-(2,2,2-trifluoro-1-methyl-ethyl)-amide

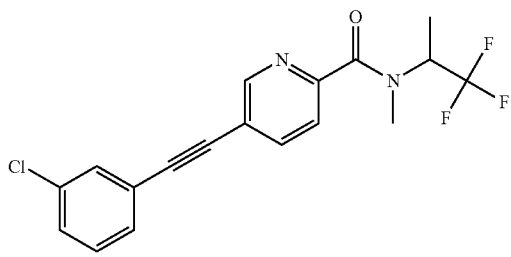 [SMILES: CC(N(C)C(=O)c1ccc(C#Cc2cccc(Cl)c2)cn1)C(F)(F)F]

The title compound was obtained as a colorless oil, MS: m/e=367.3/369.2 (M+H⁺), using chemistry similar to that described in Example 2 from (RS)-5-(3-chloro-phenylethynyl)-pyridine-2-carboxylic acid (2,2,2-trifluoro-1-methyl-ethyl)-amide (Example 61) and iodomethane.

Example 63

(RS)-[5-(3-Fluoro-phenylethynyl)-pyridin-2-yl]-(4-hydroxy-2,2-dimethyl-piperidin-1-yl)-methanone

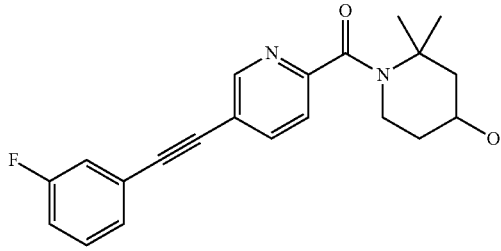 [SMILES: CC1(C)CC(O)CCN1C(=O)c1ccc(C#Cc2cccc(F)c2)cn1]

The title compound was obtained as a light yellow solid, MS: m/e=353.4 (M+H⁺), using chemistry similar to that described in Example 1, step 1 from 5-(3-fluoro-phenylethynyl)-pyridine-2-carboxylic acid (Example 25, step 1) and (RS)-2,2-dimethyl-piperidin-4-ol (CAS 937681-12-4).

Example 64

(RS)-[5-(2,5-Difluoro-phenylethynyl)-pyridin-2-yl]-(4-hydroxy-2,2-dimethyl-piperidin-1-yl)-methanone

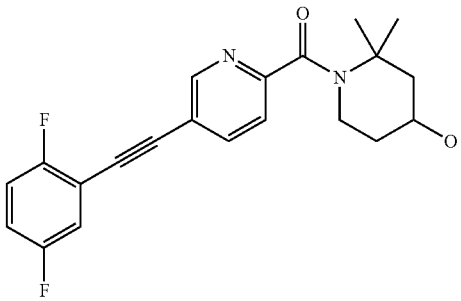 [SMILES: CC1(C)CC(O)CCN1C(=O)c1ccc(C#Cc2cc(F)ccc2F)cn1]

The title compound was obtained as a light yellow solid, MS: m/e=371.4 (M–H⁺), using chemistry similar to that described in Example 1, step 2 from (RS)-(5-bromo-pyridin-2-yl)-(4-hydroxy-2,2-dimethyl-piperidin-1-yl)-methanone (Example 38, step 1) and 2,5-difluorophenylacetylene.

Example 65

(RS)-[5-(3-Fluoro-phenylethynyl)-pyrimidin-2-yl]-(4-hydroxy-2,2-dimethyl-piperidin-1-yl)-methanone

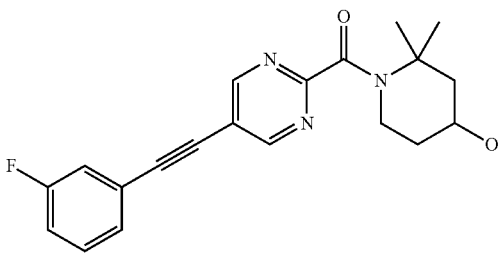

Step 1: (RS)-(5-Bromo-pyrimidin-2-yl)-(4-hydroxy-2,2-dimethyl-piperidin-1-yl)-methanone

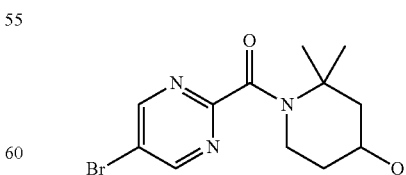

The title compound was obtained as a white solid, MS: m/e=314.4/316.3 (M+H⁺), using chemistry similar to that described in Example 1, step 1 from 5-bromo-pyrimidine-2-carboxylic acid and (RS)-2,2-dimethyl-piperidin-4-ol (CAS 937681-12-4).

Step 2: (RS)-[5-(3-Fluoro-phenylethynyl)-pyrimidin-2-yl]-(4-hydroxy-2,2-dimethyl-piperidin-1-yl)-methanone

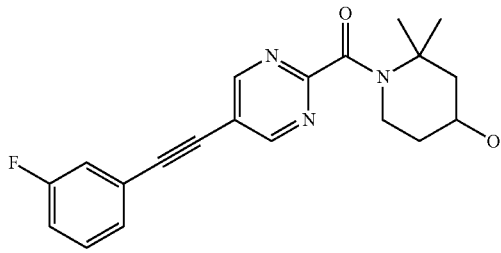

The title compound was obtained as a light yellow solid, MS: m/e=354.4 (M–H⁺), using chemistry similar to that described in Example 1, step 2 from (RS)-(5-bromo-pyrimidin-2-yl)-(4-hydroxy-2,2-dimethyl-piperidin-1-yl)-methanone (Example 65, step 1) and 3-fluorophenylacetylene.

Example 66

(RS)-[5-(2,5-Difluoro-phenylethynyl)-pyrimidin-2-yl]-(4-hydroxy-2,2-dimethyl-piperidin-1-yl)-methanone

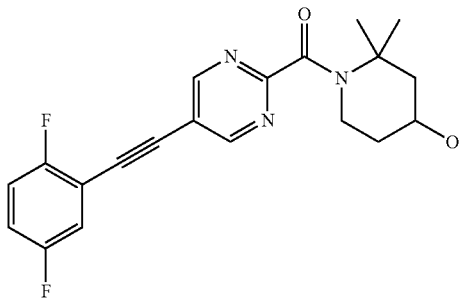 [SMILES: CC1(C)CC(O)CCN1C(=O)c1ncc(C#Cc2cc(F)ccc2F)cn1]

The title compound was obtained as a yellow solid, MS: m/e=372.4 (M–H⁺), using chemistry similar to that described in Example 1, step 2 from (RS)-(5-bromo-pyrimidin-2-yl)-(4-hydroxy-2,2-dimethyl-piperidin-1-yl)-methanone (Example 65, step 1) and 2,5-difluorophenylacetylene.

Example 67

(RS)-[3-Fluoro-5-(3-fluoro-phenylethynyl)-pyridin-2-yl]-(4-hydroxy-2,2-dimethyl-piperidin-1-yl)-methanone

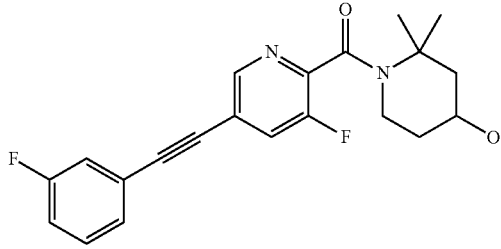

Step 1: (RS)-(5-Bromo-3-fluoro-pyridin-2-yl)-(4-hydroxy-2,2-dimethyl-piperidin-1-yl)-methanone

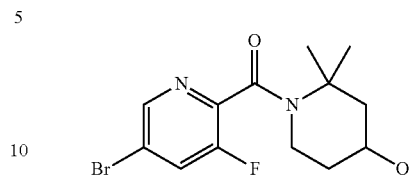

The title compound was obtained as a yellow oil, MS: m/e=331.2/333.2 (M+H⁺), using chemistry similar to that described in Example 1, step 1 from 5-bromo-3-fluoro-pyridine-2-carboxylic acid and (RS)-2,2-dimethyl-piperidin-4-ol (CAS 937681-12-4).

Step 2: (RS)-[3-Fluoro-5-(3-fluoro-phenylethynyl)-pyridin-2-yl]-(4-hydroxy-2,2-dimethyl-piperidin-1-yl)-methanone

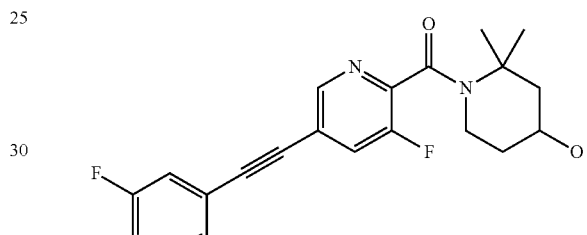

The title compound was obtained as a yellow oil, MS: m/e=371.4 (M–H⁺), using chemistry similar to that described in Example 1, step 2 from (RS)-(5-bromo-3-fluoro-pyridin-2-yl)-(4-hydroxy-2,2-dimethyl-piperidin-1-yl)-methanone (Example 67, step 1) and 3-fluorophenylacetylene.

Example 68

(RS)-[5-(2,5-Difluoro-phenylethynyl)-3-fluoro-pyridin-2-yl]-(4-hydroxy-2,2-dimethyl-piperidin-1-yl)-methanone

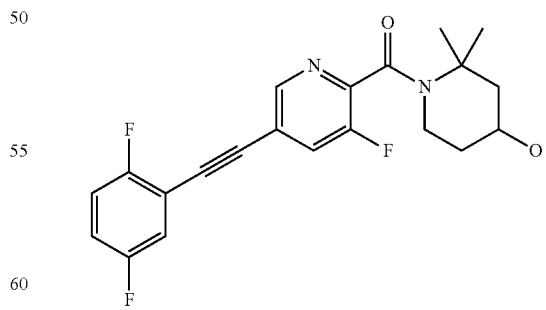

The title compound was obtained as a yellow solid, MS: m/e=389.4 (M–H⁺), using chemistry similar to that described in Example 1, step 2 from (RS)-(5-bromo-3-fluoro-pyridin-2-yl)-(4-hydroxy-2,2-dimethyl-piperidin-1-yl)-methanone (Example 67, step 1) and 2,5-difluorophenylacetylene.

The invention claimed is:
1. A compound of formula I

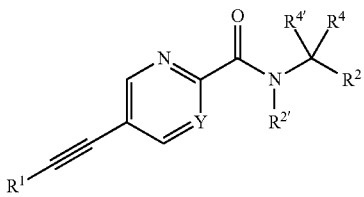

wherein
Y is N or C—R³,
R³ is hydrogen, methyl, halogen or nitrile;
R¹ is selected from the group consisting of pyridinyl, optionally substituted by halogen, lower alkyl or lower alkoxy, and phenyl substituted by halogen, lower alkyl or lower alkoxy;
R²/R²' are each independently hydrogen, lower alkyl or lower alkyl substituted by halogen, or R² and R²' together with the N-atom to which they are attached form a morpholine ring, a piperidine ring or an azetidine ring, each of which is unsubstituted or substituted one or more substituents selected from lower alkoxy, halogen, hydroxy and methyl;
R⁴/R⁴' are each independently hydrogen or lower alkyl, or R⁴ and R⁴' together form tetrahydrofuran- or an oxetane- ring;
or a pharmaceutically acceptable acid addition salt, racemic mixture, corresponding enantiomer, optical isomer, or stereoisomer thereof.

2. A compound of formula IA,

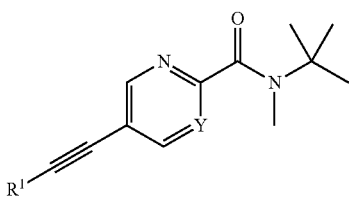

wherein
Y is N or C—R³;
R³ is hydrogen, methyl, halogen or nitrile;
R¹ is phenyl or pyridinyl, each of which is optionally substituted by halogen, lower alkyl or lower alkoxy;
or a pharmaceutically acceptable acid addition salt, racemic mixture, corresponding enantiomer, optical isomer, or stereoisomer thereof.

3. The compound of claim 2, selected from the group consisting of
5-phenylethynyl-pyridine-2-carboxylic acid tert-butyl-methyl-amide;
5-(3-fluoro-phenylethynyl)-pyridine-2-carboxylic acid tert-butyl-methyl-amide;
5-(4-fluoro-phenylethynyl)-pyridine-2-carboxylic acid tert-butyl-methyl-amide;
5-(2,5-difluoro-phenylethynyl)-pyridine-2-carboxylic acid tert-butyl-methyl-amide;
5-pyridin-3-ylethynyl-pyridine-2-carboxylic acid tert-butyl-methyl-amide;
5-(5-chloro-pyridin-3-ylethynyl)-pyridine-2-carboxylic acid tert-butyl-methyl-amide;
5-(5-fluoro-pyridin-3-ylethynyl)-pyridine-2-carboxylic acid tert-butyl-methyl-amide;
5-(4-fluoro-phenylethynyl)-pyrimidine-2-carboxylic acid tert-butyl-methyl-amide;
5-(3-fluoro-phenylethynyl)-pyrimidine-2-carboxylic acid tert-butyl-methyl-amide; and
5-(2,5-difluoro-phenylethynyl)-pyrimidine-2-carboxylic acid tert-butyl-methyl-amide;
or a pharmaceutically acceptable acid addition salt, racemic mixture, corresponding enantiomer, optical isomer, or stereoisomer thereof.

4. The compound of claim 2, selected from the group consisting of
5-(5-chloro-pyridin-3-ylethynyl)-pyrimidine-2-carboxylic acid tert-butyl-methyl-amide;
5-(3-fluoro-phenylethynyl)-3-methyl-pyridine-2-carboxylic acid tert-butyl-methyl-amide;
5-(4-fluoro-phenylethynyl)-3-methyl-pyridine-2-carboxylic acid tert-butyl-methyl-amide;
5-(2,5-difluoro-phenylethynyl)-3-methyl-pyridine-2-carboxylic acid tert-butyl-methyl-amide;
5-(5-chloro-pyridin-3-ylethynyl)-3-methyl-pyridine-2-carboxylic acid tert-butyl-methyl-amide;
3-fluoro-5-(3-fluoro-phenylethynyl)-pyridine-2-carboxylic acid tert-butyl-methyl-amide;
3-fluoro-5-(4-fluoro-phenylethynyl)-pyridine-2-carboxylic acid tert-butyl-methyl-amide;
5-(2,5-difluoro-phenylethynyl)-3-fluoro-pyridine-2-carboxylic acid tert-butyl-methyl-amide;
5-(5-chloro-pyridin-3-ylethynyl)-3-fluoro-pyridine-2-carboxylic acid tert-butyl-methyl-amide;
3-chloro-5-phenylethynyl-pyridine-2-carboxylic acid tert-butyl-methyl-amide; and
3-cyano-5-phenylethynyl-pyridine-2-carboxylic acid tert-butyl-methyl-amide;
or a pharmaceutically acceptable acid addition salt, racemic mixture, corresponding enantiomer, optical isomer, or stereoisomer thereof.

5. The compound of claim 1, wherein R¹ is phenyl substituted by halogen.

6. A compound selected from the group consisting of
5-phenylethynyl-pyridine-2-carboxylic acid tert-butylamide;
5-phenylethynyl-pyridine-2-carboxylic acid tert-butyl-methyl-amide;
5-(3-fluoro-phenylethynyl)-pyridine-2-carboxylic acid tert-butyl-methyl-amide;
5-(4-fluoro-phenylethynyl)-pyridine-2-carboxylic acid tert-butyl-methyl-amide;
5-(2,5-difluoro-phenylethynyl)-pyridine-2-carboxylic acid tert-butyl-methyl-amide;
5-(4-fluoro-phenylethynyl)-pyrimidine-2-carboxylic acid tert-butylamide;
5-(3-fluoro-phenylethynyl)-pyrimidine-2-carboxylic acid tert-butylamide;
5-(4-fluoro-phenylethynyl)-pyrimidine-2-carboxylic acid tert-butyl-methyl-amide;
5-(3-fluoro-phenylethynyl)-pyrimidine-2-carboxylic acid tert-butyl-methyl-amide; and
5-m-tolylethynyl-pyrimidine-2-carboxylic acid tert-butylamide;
or a pharmaceutically acceptable acid addition salt, racemic mixture, corresponding enantiomer, optical isomer, or stereoisomer thereof.

7. The compound of claim 1, selected from the group consisting of
5-(3-chloro-phenylethynyl)-pyrimidine-2-carboxylic acid tert-butylamide;
5-(2,5-difluoro-phenylethynyl)-pyrimidine-2-carboxylic acid tert-butyl-methyl-amide;
5-(3-fluoro-phenylethynyl)-3-methyl-pyridine-2-carboxylic acid tert-butyl-methyl-amide;
5-(4-fluoro-phenylethynyl)-3-methyl-pyridine-2-carboxylic acid tert-butyl-methyl-amide;
5-(2,5-difluoro-phenylethynyl)-3-methyl-pyridine-2-carboxylic acid tert-butyl-methyl-amide;
3-fluoro-5-(3-fluoro-phenylethynyl)-pyridine-2-carboxylic acid tert-butyl-methyl-amide;
3-fluoro-5-(4-fluoro-phenylethynyl)-pyridine-2-carboxylic acid tert-butyl-methyl-amide;
5-(2,5-difluoro-phenylethynyl)-3-fluoro-pyridine-2-carboxylic acid tert-butyl-methyl-amide; and
5-(3-fluoro-phenylethynyl)-pyridine-2-carboxylic acid oxetan-3-ylamide;
or a pharmaceutically acceptable acid addition salt, racemic mixture, corresponding enantiomer, optical isomer, or stereoisomer thereof.

8. The compound of claim 1, selected from the group consisting of
5-(3-fluoro-phenylethynyl)-pyridine-2-carboxylic acid methyl-(3-methyl-oxetan-3-yl)-amide;
5-(4-fluoro-phenylethynyl)-pyridine-2-carboxylic acid methyl-(3-methyl-oxetan-3-yl)-amide;
5-(2,5-difluoro-phenylethynyl)-pyridine-2-carboxylic acid methyl-(3-methyl-oxetan-3-yl)-amide;
5-(3,4-difluoro-phenylethynyl)-pyridine-2-carboxylic acid methyl-(3-methyl-oxetan-3-yl)-amide; and
(2,2-dimethyl-morpholin-4-yl)-[5-(3-fluoro-phenylethynyl)-pyridin-2-yl]-methanone;
or a pharmaceutically acceptable acid addition salt, racemic mixture, corresponding enantiomer, optical isomer, or stereoisomer thereof.

9. A compound selected from the group consisting of [5-(2,5-difluoro-phenylethynyl)-pyridin-2-yl]-(2,2-dimethyl-morpholin-4-yl)-methanone;
[5-(3-fluoro-phenylethynyl)-pyridin-2-yl]-(4-hydroxy-4-methyl-piperidin-1-yl)-methanone;
(RS)-(4-hydroxy-2,2-dimethyl-piperidin-1-yl)-(5-phenylethynyl-pyridin-2-yl)-methanone;
(RS)-(4-hydroxy-3,3-dimethyl-piperidin-1-yl)-(5-phenylethynyl-pyridin-2-yl)-methanone;
(RS)-[5-(4-fluoro-phenylethynyl)-pyridin-2-yl]-(4-hydroxy-3,3-dimethyl-piperidin-1-yl)-methanone;
(RS)-[5-(3-fluoro-phenylethynyl)-pyridin-2-yl]-(4-hydroxy-3,3-dimethyl-piperidin-1-yl)-methanone;
3-chloro-5-phenylethynyl-pyridine-2-carboxylic acid tert-butyl-methyl-amide; and
(3,3-difluoro-azetidin-1-yl)-(5-phenylethynyl-pyrimidin-2-yl)-methanone;
or a pharmaceutically acceptable acid addition salt, racemic mixture, corresponding enantiomer, optical isomer, or stereoisomer thereof.

10. A compound selected from the group consisting of
(3,3-dimethyl-piperidin-1-yl)-(5-phenylethynyl-pyrimidin-2-yl)-methanone;
(RS)-(4-hydroxy-2,2-dimethyl-piperidin-1-yl)-(5-phenylethynyl-pyrimidin-2-yl)-methanone;
(RS)-(4-hydroxy-3,3-dimethyl-piperidin-1-yl)-(5-phenylethynyl-pyrimidin-2-yl)-methanone;
(RS)-[5-(3-fluoro-phenylethynyl)-pyrimidin-2-yl]-(4-hydroxy-3,3-dimethyl-piperidin-1-yl)-methanone;
3-fluoro-5-phenylethynyl-pyridine-2-carboxylic acid methyl-(3-methyl-oxetan-3-yl)-amide;
(RS)-3-fluoro-5-phenylethynyl-pyridine-2-carboxylic acid methyl-(2,2,2-trifluoro-1-methyl-ethyl)-amide;
3-cyano-5-phenylethynyl-pyridine-2-carboxylic acid tert-butyl-methyl-amide;
5-(3-chloro-phenylethynyl)-pyridine-2-carboxylic acid methyl-(2,2,2-trifluoro-1,1-dimethyl-ethyl)-amide;
(RS)-5-(3-chloro-phenylethynyl)-pyridine-2-carboxylic acid (2,2,2-trifluoro-1-methyl-ethyl)-amide; and
(RS)-5-(3-chloro-phenylethynyl)-pyridine-2-carboxylic acid methyl-(2,2,2-trifluoro-1-methyl-ethyl)-amide;
or a pharmaceutically acceptable acid addition salt, racemic mixture, corresponding enantiomer, optical isomer, or stereoisomer thereof.

11. The compound of claim 1, wherein $R^1$ is pyridinyl, optionally substituted by halogen.

12. The compound of claim 1, selected from the group consisting of 5-pyridin-3-ylethynyl-pyridine-2-carboxylic acid tert-butyl-methyl-amide;
5-(5-chloro-pyridin-3-ylethynyl)-pyridine-2-carboxylic acid tert-butyl-methyl-amide;
5-(5-fluoro-pyridin-3-ylethynyl)-pyridine-2-carboxylic acid tert-butyl-methyl-amide;
5-(5-chloro-pyridin-3-ylethynyl)-pyrimidine-2-carboxylic acid tert-butyl-methyl-amide;
5-(5-chloro-pyridin-3-ylethynyl)-3-methyl-pyridine-2-carboxylic acid tert-butyl-methyl-amide;
5-(5-chloro-pyridin-3-ylethynyl)-3-fluoro-pyridine-2-carboxylic acid tert-butyl-methyl-amide;
5-(2-chloro-pyridin-4-ylethynyl)-pyridine-2-carboxylic acid (2,2,2-trifluoro-1,1-dimethyl-ethyl)-amide;
5-(5-chloro-pyridin-3-ylethynyl)-pyridine-2-carboxylic acid methyl-(2,2,2-trifluoro-1,1-dimethyl-ethyl)-amide;
(RS)-5-(2-chloro-pyridin-4-ylethynyl)-pyridine-2-carboxylic acid (2,2,2-trifluoro-1-methyl-ethyl)-amide;
5-(2-chloro-pyridin-4-ylethynyl)-pyrimidine-2-carboxylic acid (2,2,2-trifluoro-1,1-dimethyl-ethyl)-amide;
(R) or (S)-5-(2-chloro-pyridin-4-ylethynyl)-pyridine-2-carboxylic acid (2,2,2-trifluoro-1-methyl-ethyl)-amide; and
(S) or (R)-5-(2-chloro-pyridin-4-ylethynyl)-pyridine-2-carboxylic acid (2,2,2-trifluoro-1-methyl-ethyl)-amide;
or a pharmaceutically acceptable acid addition salt, racemic mixture, corresponding enantiomer, optical isomer, or stereoisomer thereof.

13. A pharmaceutical composition comprising a therapeutically effective amount of a compound of formula I

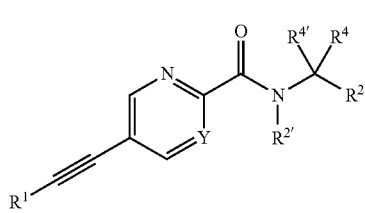

wherein
Y is N or C—$R^3$;
$R^3$ is hydrogen, methyl, halogen or nitrile;
$R^1$ is selected from the group consisting of pyridinyl, optionally substituted by halogen, lower alkyl or lower alkoxy, and phenyl substituted by halogen, lower alkyl or lower alkoxy;

$R^2/R^{2'}$ are each independently hydrogen, lower alkyl or lower alkyl substituted by halogen,
  or $R^2$ and $R^{2'}$ together with the N-atom to which they are attached form a morpholine ring, a piperidine ring or an azetidine ring, each of which is unsubstituted or substituted one or more substituents selected from lower alkoxy, halogen, hydroxy and methyl;
$R^4/R^{4'}$ are each independently hydrogen or lower alkyl,
  or $R^4$ and $R^{4'}$ together form tetrahydrofuran- or an oxetane-ring;
or a pharmaceutically acceptable acid addition salt, racemic mixture, corresponding enantiomer, optical isomer, or stereoisomer thereof and a pharmaceutically acceptable carrier.

14. The compound of claim 3 wherein said compound is 5-(2,5-difluoro-phenylethynyl)-pyridine-2-carboxylic acid tert-butyl-methyl-amide or a pharmaceutically acceptable acid addition salt, racemic mixture, corresponding enantiomer, optical isomer, or stereoisomer thereof.

* * * * *